(12) United States Patent  
He et al.

(10) Patent No.: US 9,396,642 B2
(45) Date of Patent: Jul. 19, 2016

(54) CONTROL USING CONNECTED BIOMETRIC DEVICES

(71) Applicant: Quanttus, Inc., Cambridge, MA (US)

(72) Inventors: David Da He, Cambridge, MA (US); Richard Robehr Bijjani, Cambridge, MA (US); Shahid Azim, Cambridge, MA (US); Bogart Vargas, Cambridge, MA (US)

(73) Assignee: Quanttus, Inc., Cambridge, MA (US)

( * ) Notice: Subject to any disclaimer, the term of this patent is extended or adjusted under 35 U.S.C. 154(b) by 0 days.

(21) Appl. No.: 14/522,157

(22) Filed: Oct. 23, 2014

(65) Prior Publication Data

US 2015/0112452 A1 Apr. 23, 2015

Related U.S. Application Data

(60) Provisional application No. 61/894,884, filed on Oct. 23, 2013, provisional application No. 62/002,531, filed on May 23, 2014.

(51) Int. Cl.
G05B 15/02 (2006.01)
H05B 37/02 (2006.01)
(Continued)

(52) U.S. Cl.
CPC .......... *G08B 21/0453* (2013.01); *A61B 5/0022* (2013.01); *A61B 5/0205* (2013.01); *A61B 5/029* (2013.01); *A61B 5/02028* (2013.01); *A61B 5/02055* (2013.01); *A61B 5/0285* (2013.01); *A61B 5/02108* (2013.01); *A61B 5/02125* (2013.01); *A61B 5/02416* (2013.01); *A61B 5/02427* (2013.01); *A61B 5/08* (2013.01); *A61B 5/11* (2013.01); *A61B 5/1102* (2013.01); *A61B 5/113* (2013.01); *A61B 5/1118* (2013.01); *A61B 5/14542* (2013.01); *A61B 5/16* (2013.01); *A61B 5/165* (2013.01); *A61B 5/486* (2013.01); *A61B 5/4809* (2013.01); *A61B 5/4815* (2013.01); *A61B 5/4818* (2013.01); *A61B 5/4833* (2013.01); *A61B 5/6801* (2013.01);
(Continued)

(58) Field of Classification Search
CPC ....... G08B 21/06; A61B 5/0285; A61B 5/117
See application file for complete search history.

(56) References Cited

U.S. PATENT DOCUMENTS 4,854,699 A 8/1989 Edgar, Jr.
5,515,858 A 5/1996 Myllymaki
(Continued)

FOREIGN PATENT DOCUMENTS

CA 2826866 8/2012
EP 267884 5/1988
(Continued)

OTHER PUBLICATIONS

Drugs.com (Drug Dosage, http://www.drugs.com/dosage/ Jan. 27, 2010), 2 pages.
(Continued)

Primary Examiner — Ramesh Patel
(74) Attorney, Agent, or Firm — Fish & Richardson P.C.

(57) ABSTRACT

The technology described in this document is embodied in a method that includes processing data in a first dataset that represents time-varying information about at least one pulse pressure wave propagating through blood in a subject acquired at a location of the subject. The method also includes providing information related to the data to a remote device.

30 Claims, 56 Drawing Sheets

(51) Int. Cl.
*A61B 5/0464* (2006.01)
*A61B 5/11* (2006.01)
*A61B 5/0205* (2006.01)
*A61B 5/02* (2006.01)
*G08B 21/04* (2006.01)
*A61B 5/00* (2006.01)
*A61B 5/021* (2006.01)
*A61B 5/16* (2006.01)
*A61B 5/113* (2006.01)
*A61B 5/029* (2006.01)
*A61B 5/145* (2006.01)
*G06F 3/0481* (2013.01)
*H04W 8/08* (2009.01)
*A61B 5/0285* (2006.01)
*G08B 21/06* (2006.01)
*G06F 21/00* (2013.01)
*G06F 21/32* (2013.01)
*A61B 5/024* (2006.01)
*A61B 5/053* (2006.01)
*A61B 5/08* (2006.01)
*H04L 29/08* (2006.01)
*A61B 5/117* (2016.01)

(52) U.S. Cl.
CPC ............ *A61B 5/681* (2013.01); *A61B 5/6824* (2013.01); *A61B 5/6898* (2013.01); *A61B 5/7275* (2013.01); *A61B 5/7278* (2013.01); *A61B 5/7282* (2013.01); *A61B 5/742* (2013.01); *A61B 5/746* (2013.01); *G05B 15/02* (2013.01); *G06F 3/0481* (2013.01); *G06F 21/00* (2013.01); *G06F 21/32* (2013.01); *G08B 21/06* (2013.01); *H04W 8/08* (2013.01); *H05B 37/0227* (2013.01); *H05B 37/0272* (2013.01); *A61B 5/02007* (2013.01); *A61B 5/02405* (2013.01); *A61B 5/02438* (2013.01); *A61B 5/0464* (2013.01); *A61B 5/0531* (2013.01); *A61B 5/0816* (2013.01); *A61B 5/117* (2013.01); *H04L 67/12* (2013.01)

(56) References Cited

U.S. PATENT DOCUMENTS

| | | | |
|---|---|---|---|
| 5,613,495 A | 3/1997 | Mills et al. | |
| 5,622,178 A | 4/1997 | Gilham | |
| 5,692,501 A | 12/1997 | Minturn | |
| 5,818,788 A | 10/1998 | Sodini et al. | |
| 5,836,884 A | 11/1998 | Chio | |
| 6,008,703 A | 12/1999 | Perrott et al. | |
| 6,030,342 A | 2/2000 | Amano et al. | |
| 6,478,736 B1 | 11/2002 | Mault | |
| 6,480,733 B1 | 11/2002 | Turcott | |
| 6,540,686 B2 | 4/2003 | Heikkila et al. | |
| 6,600,471 B2 | 7/2003 | Lee et al. | |
| 6,605,038 B1 | 8/2003 | Teller et al. | |
| 6,791,462 B2 | 9/2004 | Choi | |
| 6,928,535 B2 | 8/2005 | Yamashita et al. | |
| 7,020,508 B2 | 3/2006 | Stivoric et al. | |
| 7,054,679 B2 | 5/2006 | Hirsh | |
| 7,153,262 B2 | 12/2006 | Stivoric et al. | |
| 7,218,966 B2 | 5/2007 | Haefner | |
| 7,261,690 B2 | 8/2007 | Teller et al. | |
| 7,285,090 B2 | 10/2007 | Stivoric et al. | |
| 7,319,425 B2 | 1/2008 | Fiorenza et al. | |
| 7,349,574 B1 | 3/2008 | Sodini et al. | |
| 7,534,206 B1 | 5/2009 | Lovitt et al. | |
| 7,539,532 B2 | 5/2009 | Tran | |
| 7,657,307 B2 | 2/2010 | Van Dam | |
| 7,689,437 B1 | 3/2010 | Teller et al. | |
| 7,846,104 B2 | 12/2010 | MacQuarrie et al. | |
| 7,946,959 B2 | 5/2011 | Shum et al. | |
| 8,036,851 B2 | 10/2011 | Vock et al. | |
| 8,073,707 B2 | 12/2011 | Teller et al. | |
| 8,108,036 B2 * | 1/2012 | Tran .................... | A61B 5/4076 600/509 |
| 8,172,761 B1 | 5/2012 | Rulkov et al. | |
| 8,224,429 B2 | 7/2012 | Prstojevich et al. | |
| 8,275,635 B2 | 9/2012 | Stivoric et al. | |
| 8,292,806 B2 | 10/2012 | Shimada et al. | |
| 8,323,188 B2 | 12/2012 | Tran | |
| 8,328,718 B2 | 12/2012 | Tran | |
| 8,369,936 B2 | 2/2013 | Farringdon et al. | |
| 8,449,471 B2 | 5/2013 | Tran | |
| 8,463,577 B2 | 6/2013 | Yuen et al. | |
| 8,500,636 B2 | 8/2013 | Tran | |
| 8,519,835 B2 | 8/2013 | Dunko | |
| 8,543,185 B2 | 9/2013 | Yuen et al. | |
| 8,543,351 B2 | 9/2013 | Yuen et al. | |
| 8,548,770 B2 | 10/2013 | Yuen et al. | |
| 8,568,330 B2 | 10/2013 | Mollicone et al. | |
| 8,583,402 B2 | 11/2013 | Yuen et al. | |
| 8,663,106 B2 | 3/2014 | Stivoric et al. | |
| 8,670,953 B2 | 3/2014 | Yuen et al. | |
| 8,684,900 B2 | 4/2014 | Tran | |
| 8,684,922 B2 | 4/2014 | Tran | |
| 8,694,136 B2 | 4/2014 | Ellis et al. | |
| 8,702,627 B2 | 4/2014 | Telfort et al. | |
| 8,715,206 B2 | 5/2014 | Telfort et al. | |
| 8,721,502 B2 | 5/2014 | Ellis et al. | |
| 8,725,276 B2 | 5/2014 | Ellis et al. | |
| 8,725,311 B1 | 5/2014 | Breed | |
| 8,764,651 B2 | 7/2014 | Tran | |
| 8,764,653 B2 | 7/2014 | Kaminska et al. | |
| 8,777,815 B2 | 7/2014 | Case, Jr. et al. | |
| 8,894,548 B2 | 11/2014 | Ellis et al. | |
| 8,903,671 B2 * | 12/2014 | Park .................... | G08B 21/18 702/104 |
| 2004/0129787 A1 | 7/2004 | Saito et al. | |
| 2005/0209512 A1 | 9/2005 | Heruth et al. | |
| 2006/0224051 A1 * | 10/2006 | Teller ................ | A61B 5/02055 600/300 |
| 2007/0010748 A1 * | 1/2007 | Rauch ................. | A61B 5/4023 600/481 |
| 2007/0032731 A1 | 2/2007 | Lovejoy et al. | |
| 2007/0197881 A1 * | 8/2007 | Wolf .................... | A61B 5/0002 600/300 |
| 2007/0232454 A1 | 10/2007 | Kagan et al. | |
| 2008/0076972 A1 | 3/2008 | Dorogusker et al. | |
| 2008/0139955 A1 | 6/2008 | Hansmann et al. | |
| 2008/0171943 A1 * | 7/2008 | Farringdon .......... | A61B 5/0428 600/509 |
| 2008/0177162 A1 | 7/2008 | Bae et al. | |
| 2008/0287821 A1 | 11/2008 | Jung et al. | |
| 2009/0273467 A1 | 11/2009 | Elixmann et al. | |
| 2010/0076276 A1 | 3/2010 | Gilland | |
| 2010/0249541 A1 | 9/2010 | Geva et al. | |
| 2010/0292589 A1 | 11/2010 | Goodman | |
| 2010/0324429 A1 | 12/2010 | Leschinsky | |
| 2010/0331631 A1 | 12/2010 | MacLaughlin | |
| 2011/0066042 A1 * | 3/2011 | Pandia .................. | A61B 5/029 600/484 |
| 2011/0124979 A1 | 5/2011 | Heneghan et al. | |
| 2011/0172504 A1 * | 7/2011 | Wegerich ............ | A61B 5/0205 600/301 |
| 2011/0190650 A1 * | 8/2011 | McNair ................ | A61B 5/00 600/518 |
| 2011/0224498 A1 | 9/2011 | Banet et al. | |
| 2011/0224500 A1 | 9/2011 | Banet | |
| 2012/0059237 A1 * | 3/2012 | Amir .................... | A61B 5/0285 600/365 |
| 2012/0075122 A1 | 3/2012 | Whitlow | |
| 2012/0191147 A1 * | 7/2012 | Rao ...................... | G06F 3/023 607/3 |
| 2012/0197353 A1 * | 8/2012 | Donnelly ............ | A61B 5/02055 607/62 |
| 2012/0203077 A1 | 8/2012 | He et al. | |
| 2012/0209126 A1 | 8/2012 | Amos et al. | |
| 2013/0095459 A1 | 4/2013 | Tran | |
| 2013/0116576 A1 * | 5/2013 | Morren .............. | A61B 5/02014 600/479 |

(56) References Cited

U.S. PATENT DOCUMENTS

| | | | |
|---|---|---|---|
| 2013/0131464 A1 | 5/2013 | Westbrook et al. | |
| 2013/0172691 A1 | 7/2013 | Tran | |
| 2013/0231574 A1 | 9/2013 | Tran | |
| 2013/0267789 A1 | 10/2013 | Stivoric et al. | |
| 2013/0276785 A1 | 10/2013 | Melker et al. | |
| 2013/0338460 A1* | 12/2013 | He | A61B 5/0205 600/324 |
| 2014/0073486 A1 | 3/2014 | Ahmed | |
| 2014/0085050 A1 | 3/2014 | Luna | |
| 2014/0088994 A1 | 3/2014 | Kroh | |
| 2014/0089672 A1 | 3/2014 | Luna | |
| 2014/0089673 A1 | 3/2014 | Luna | |
| 2014/0107493 A1* | 4/2014 | Yuen | H04W 4/027 600/473 |
| 2014/0235979 A1 | 8/2014 | Banet et al. | |
| 2014/0247153 A1* | 9/2014 | Proud | H02J 7/025 340/870.09 |
| 2014/0275883 A1* | 9/2014 | Haisley | A61B 5/14552 600/324 |
| 2015/0018637 A1* | 1/2015 | Chen | A61B 5/02125 600/301 |
| 2015/0057511 A1* | 2/2015 | Basu | A61B 5/02433 600/323 |
| 2015/0135310 A1 | 5/2015 | Lee | |

FOREIGN PATENT DOCUMENTS

| | | |
|---|---|---|
| EP | 0262779 | 4/1993 |
| EP | 1551282 | 4/2004 |
| EP | 1292217 | 11/2005 |
| EP | 2116183 | 2/2012 |
| EP | 1414340 | 7/2013 |
| EP | 1639939 | 7/2013 |
| GB | 2408105 | 5/2005 |
| WO | 2008/095318 | 8/2008 |
| WO | 2010/025166 | 3/2010 |
| WO | 2010/108287 | 9/2010 |
| WO | 2011/113070 | 9/2011 |
| WO | 2012/108895 | 8/2012 |
| WO | 2013/066642 | 5/2013 |
| WO | 2013093690 | 6/2013 |
| WO | 2013/122788 | 8/2013 |
| WO | 2013/125987 | 8/2013 |
| WO | 2013/192166 | 12/2013 |
| WO | WO 2014/022906 | 2/2014 |

OTHER PUBLICATIONS

Principles of Circulation (http://degacy.owensboro.kctcs.edu/GCaplan/anat2/notes/APIINotes5%20cardiac_equations.htm, May 15, 2011), 4 pages.

International Search Report and Written Opinion, issued in PCT/US2014/061987, mailed Mar. 26, 2015 (12 pages).

DC Rainmaker (http://www.dcrainmaker.com/2010/12/zeo-in-depth-product-review.html/ dated Dec. 20, 2010 (accessed Jul. 22, 2015.

Vernier (http://www.vernier.com/experiments/bio-a/10b/heart_rate_and_physicalfitness/) backdated to May 5, 2012 using the wayback machine (https://archive.org/web/).

He et al., "The Ear as a Location for Wearable Vital Signs Monitoring," $32^{nd}$ Annual International Conference of the IEEE EMBS, Aug. 31-Sep. 4, 2010 (4 pages).

Robinson, "Healbe offers more bunk "science" to back up miracle claims. It's time for Indiegogo to stop this," http://pando.com/2014/04/01/healbe-offers-more-bunk-science-to-back-up-miracle-claims-its-time-for-indiegogo-to-stop-this/ PandoDaily, Apr. 1, 2014 (11 pages).

"Healbe GoBe: The Only Way to Automatically Measure Calorie Intake," http://www.indiegogo.com/projects/healbe-gobe-the-only-way-to-automatically-measure-c, Apr. 9, 2014 (31 pages).

"5 biometric alternatives to the password," http://www.cnn.com/2014/04/04/tech/innovation/5-biometrics-future/, Apr. 9, 2014 (5 pages).

Winokur et al., "A Wearable Vital Signs Monitor at the Ear for Continuous Heart Rate and Pulse Transit Time Measurements," Engineering in Medicine and Biology Society (EMBC), 2012 Annual International Conference of the IEEE (2012).

Asada et al., "Mobile monitoring with wearable photoplethysmographic biosensors," Engineering in Medicine and Biology Magazine, IEEE 22.3:28-40 (2003).

International Search Report and Written Opinion issued in PCT/US2016/016370, mailed May 19, 2016 (7 pages).

Iwagami Taisuke et al., "Brief and convenient method of estimation of pulse transis time using EGG R-wave," Journal of Life Support Engineering, 10:4 (1998).

\* cited by examiner

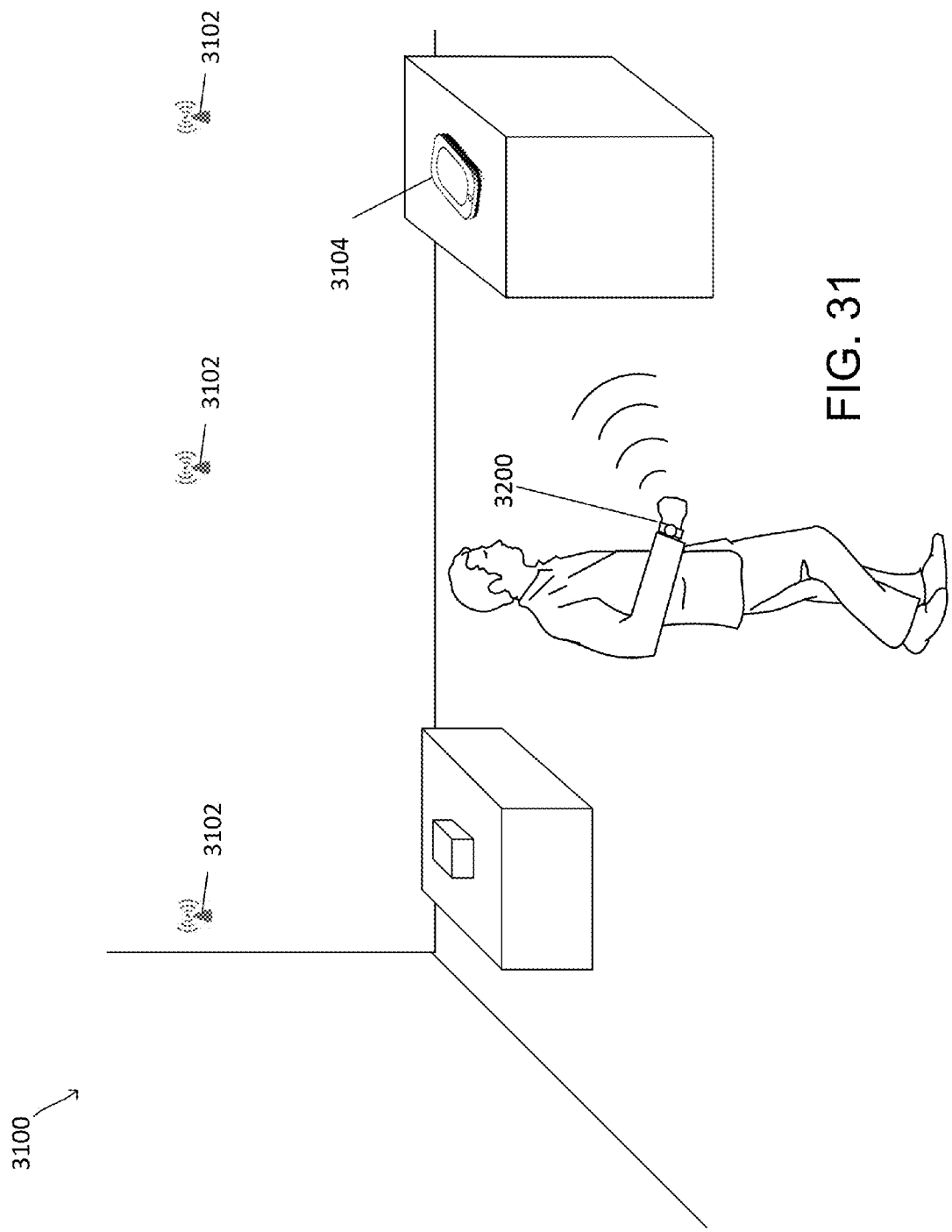

Stress

3900

You're very Zen! This week you kept your stress under control.

Largest stressor
Work Emails late at Night

Most effective destressors
Running for 20 min or more
Avoiding screens before bed
Sleep for at least 7.5 hrs

Stress & Exercise

▲ Stress                                          ▼ Lower Stress
Mon  Tues  Wed  Thurs  Fri  Sat  Today

Regular vigorous exercise works well to manage your stress levels.

ⓘ how to measure stress

FIG. 39A

Running Session

3925

6:30 am
6:52 am

This run one month ago

Olympic marathon runner doing the same level of exercise

Your running fitness is improving!
Your heart rate is lower and you recover much faster than when you started. Keep it up!

ⓘ how we assess stress

FIG. 39B

Cardiac Health

3950

Your heart indicates that your body is recovered and ready for normal activity Resting Heart Rate
68 bpm (-3)

66 68 67 70 75 71 68
Mon Tues Wed Thurs Fri Sat Today

Your resting heart rate is back down to its average level

Cardiac Power
5.6 watts

4.9            5.6
Jan 15         Today

As your heart gets stronger its power is increasing

Recover Rate
2.4 min

3min           2.4min
Jan 15         Today

A faster return to a resting Heart rate means you're Getting in better shape

ⓘ understanding cardiac health

FIG. 39C

CONTROL USING CONNECTED BIOMETRIC DEVICES

CROSS REFERENCE TO RELATED APPLICATIONS

This application claims priority to U.S. Provisional Application 61/894,884, filed on Oct. 23, 2013, and U.S. Provisional Application No. 62/002,531, filed on May 23, 2014, the entire content of which is incorporated herein by reference.

TECHNICAL FIELD

This document describes technology related to consumer biometric devices.

BACKGROUND

Various types of sensors can be used for sensing biometric parameters.

SUMMARY

In one aspect, a method includes obtaining, using a first sensor, a first data set representing time-varying information on at least one pulse pressure wave within vasculature at a first body part of a subject. The method also includes obtaining, using a second sensor, a second data set representing time-varying information about motion of the subject at the first body part of a subject. The method also includes identifying, using one or more processors, a first point in the first data set, the first point representing an arrival time of the pulse pressure wave at the first body part. The method also includes identifying, using the one or more processors, a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject.

In another aspect, one or more machine-readable storage devices stores instructions that are executable by one or more processing devices to perform operations including obtaining a first data set representing time-varying information on at least one pulse pressure wave within vasculature at a first body part of a subject. The operations also include obtaining a second data set representing time-varying information about motion of the subject at the first body part of a subject. The operations also include identifying a first point in the first data set. The first point represents an arrival time of the pulse pressure wave at the first body part. The operations also include identifying a second point in the second dataset. The second point represents an earlier time at which the pulse pressure wave traverses a second body part of the subject. The operations also include computing a pulse transit time (PTT) as a difference between the first and second points. The PTT represents a time taken by the pulse pressure wave to travel from the second body part to the first body part of the subject.

In another aspect, a biofeedback device configured to be worn by a subject includes a first sensor configured to obtain a first data set representing time-varying information on at least one pulse pressure wave within vasculature at a first body part of a subject. The device also includes a second sensor configured to obtain a second data set representing time-varying information about motion of the subject at the first body part of a subject. The device also includes memory. The device also includes one or more processors. The one or more processors are configured to receive the first and second data sets. The one or more processors are also configured to identify a first point in the first data set, the first point representing an arrival time of the pulse pressure wave at the first body part. The one or more processors are also configured to identify a second point in the second dataset, the second point representing an earlier time at which the pulse pressure wave traverses a second body part of the subject. The one or more processors are also configured to compute a pulse transit time (PTT) as a difference between the first and second points. The PTT represents a time taken by the pulse pressure wave to travel from the second body part to the first body part of the subject.

Implementations can include one or more of the following features.

In some implementations, the information about the at least one pulse pressure wave includes photoplethysmographic (PPG) data and the information about motion of the subject includes one or both of motioncardiogram (MoCG) data and gross motion data.

In some implementations, data including at least one of the first data set and the second data set is acquired continuously.

In some implementations, the data is acquired at a frequency of at least 16 Hz.

In some implementations, the data is acquired at a frequency of between 75 Hz and 85 Hz.

In some implementations, the data is acquired by a device worn by the subject.

In some implementations, the device is mobile and does not reduce a mobility of the subject.

In some implementations, the device processes the data.

In some implementations, the first body part is an arm of the subject.

In some implementations, the first body part is a wrist of the subject.

In some implementations, the first sensor includes an optical sensor and the second sensor includes an accelerometer or a gyroscope.

In some implementations, identifying the first point includes computing, by the one or more processors, a cross-correlation of a template segment with each of multiple segments of the first dataset. Identifying the first point also includes identifying, based on the computed cross-correlations, at least one candidate segment of the first dataset as including the first point. Identifying the first point also includes identifying, by the one or more processors, a first feature within the identified candidate segment as the first point.

In some implementations, identifying the second point includes determining a reference point in the second data set, the reference point corresponding to substantially the same point in time as the first point in the first data set. Identifying the second point also includes identifying one or more target features within a predetermined time range relative to the reference point. Identifying the second point also includes selecting a time point corresponding to one of the target features as the second point.

In some implementations, the target features includes at least one of a peak and a valley.

In some implementations, the method also includes computing a blood pressure of the subject as a function of the PTT.

In some implementations, the blood pressure includes a systolic pressure and a diastolic pressure.

In some implementations, a diastolic pressure is calculated as a linear function of the logarithm of the PTT.

In some implementations, a systolic pressure is calculated as a linear function of the diastolic pressure.

In some implementations, the pre-determined time range is associated with the systole portion of the subject's heartbeat.

In some implementations, the method also includes accepting user-input for initiating computation of the PTT.

In some implementations, the method also includes computing arterial stiffness as a function of the PTT.

In some implementations, the device also includes a mechanism that allows the device to be worn by the subject.

In some implementations, the mechanism does not reduce a mobility of the subject.

In some implementations, the one or more processors are also configured to compute a blood pressure of the subject as a function of the PTT.

In some implementations, the device also includes an input mechanism configured to accept user-input for initiating computation of the PTT.

In some implementations, the one or more processors are also configured to compute arterial stiffness as a function of the PTT.

In another aspect, a method includes processing data in a first dataset that represents time-varying information about at least one pulse pressure wave propagating through blood in a subject acquired at a location of the subject. The method also includes processing data in a second dataset that represents time-varying information about motion of the subject acquired at the location of the subject. The method also includes detecting arrhythmia of the subject based on the data.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include processing data in a second dataset that represents time-varying information about motion of the subject acquired at the location of the subject. The operations also include detecting arrhythmia of the subject based on the data.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to detect arrhythmia of the subject based on the data.

Implementations can include one or more of the following features.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the arrhythmia includes atrial fibrillation (AFIB).

In some implementations, the arrhythmia includes atrial flutter.

In some implementations, the method also includes identifying, based on gross motion data of the subject, one or more period of high activity of the subject.

In some implementations, the data that the arrhythmia detection is based on does not include data collected during the one or more periods of high activity.

In some implementations, the data that the arrhythmia detection is based on includes data collected during the one or more periods of high activity.

In some implementations, processing the data includes plotting R wave to R wave intervals (RR) versus next consecutive R wave to R wave intervals ($RR_{i+1}$).

In some implementations, processing the data includes determining whether a spread of plotted data points exceeds a predetermined spread value.

In some implementations, the method also includes determining that the subject experienced atrial fibrillation (AFIB) if the spread of the plotted data points exceeds the predetermined spread value.

In some implementations, processing the data includes determining whether multiple clusters of plotted data points are offset from a diagonal.

In some implementations, the method also includes determining that the subject experienced atrial flutter if there are multiple clusters of plotted data points offset from the diagonal.

In some implementations, processing the data includes determining one or more of heart rate, heart rate variability, and blood pressure of the subject.

In some implementations, determining the heart rate of the subject includes calculating a distance between two consecutive reference points in the first dataset, the distance representing a time that has elapsed between two consecutive heartbeats of the subject.

In some implementations, the reference points are local maxima or local minima.

In some implementations, the reference points are peaks or valleys.

In some implementations, determining the heart rate variability of the subject includes calculating distances between multiple pairs of consecutive reference points in the first dataset, each distance representing a time that has elapsed between two consecutive heartbeats of the subject.

In some implementations, atrial fibrillation is detected if the heart rate variability of the subject crosses a threshold.

In some implementations, determining the blood pressure of the subject includes identifying a first point in the first dataset, the first point representing an arrival time of the pulse pressure wave at a first body part of the subject. Determining the blood pressure of the subject also includes identifying a second point in the second dataset, the second point representing an earlier time at which the pulse pressure wave traverses a second body part of the subject. Determining the blood pressure of the subject also includes computing a pulse transit time (PTT) as a difference between the first and second points, the PTT representing a time taken by the pulse pressure wave to travel from the second body part to the first body part of the subject, wherein the PTT is related to an elasticity of one or more blood vessels of the subject. Determining the blood pressure of the subject also includes determining the blood pressure of the subject based on the elasticity of the one or more blood vessels.

In some implementations, the first body part is the location of the subject at which the data in the first data set is acquired, and the second body part is the heart of the subject.

In some implementations, processing the data includes plotting R wave to R wave intervals ($RR_i$) versus next consecutive R wave to R wave intervals ($RR_{i+1}$).

In some implementations, processing the data includes determining whether a spread of plotted data points exceeds a predetermined spread value.

In some implementations, the processor is also configured to determine that the subject experienced atrial fibrillation (AFIB) if the spread of the plotted data points exceeds the predetermined spread value.

In some implementations, processing the data includes determining whether multiple clusters of plotted data points are offset from a diagonal.

In some implementations, the processor is also configured to determine that the subject experienced atrial flutter if there are multiple clusters of plotted data points offset from the diagonal.

In another aspect, a method includes processing data that represents time-varying information about at least one pulse pressure wave propagating through blood in each of one or more subjects acquired at a location of each of the subjects. The method also includes processing data that represents time-varying information about motion of the one or more subjects acquired at the location of each of the subjects. The method also includes determining, based on the data, a quality of care provided to the one or more subjects by a care facility that cares for the one or more subjects.

In another aspect, one or more machine-readable storage devices stores instructions that are executable by one or more processing devices to perform operations including processing data that represents time-varying information about at least one pulse pressure wave propagating through blood in each of one or more subjects acquired at a location of each of the subjects. The operations also include processing data that represents time-varying information about motion of the one or more subjects acquired at the location of each of the subjects. The operations also include determining, based on the data, a quality of care provided to the one or more subjects by a care facility that cares for the one or more subjects.

In another aspect, a biofeedback device configured to be worn by one or more subjects includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to determine, based on the data, a quality of care provided to one or more subjects by a care facility that cares for the one or more subjects.

Implementations can include one or more of the following features.

In some implementations, the information about at least one pulse pressure wave propagating through blood in the subjects includes photoplethysmographic (PPG) data and the information about motion of the subjects includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at single locations of each of the subjects.

In some implementations, the data is acquired by devices worn by the subjects.

In some implementations, the devices are mobile and do not reduce mobility of the subjects.

In some implementations, the devices process the data.

In some implementations, the single location of each of the subjects is an arm of the subject.

In some implementations, the single location is a wrist of the subject.

In some implementations, determining a quality of care provided to the one or more subjects includes determining a level of physical activity experienced by each of the one or more subjects by comparing gross motion data of each subject to a threshold value.

In some implementations, the threshold is based on a metric defined by a health organization.

In some implementations, the level of physical activity includes an amount of time that each subject has exercised over a particular time period.

In some implementations, the level of physical activity includes an amount of time or a distance that each subject has walked over a particular time period.

In some implementations, the method also includes processing data that represents information about an amount of ultraviolet light that each of the one or more subjects has been exposed to over a particular time period.

In some implementations, the method also includes determining an amount of time that each of the one or more subjects has spent outside over the particular time period based on the information about the ultraviolet light.

In some implementations, the method also includes comparing the quality of care provided by the care facility to a quality of care provided by another care facility that cares for one or more other subjects.

In some implementations, the device also includes an ultraviolet light sensor configured to measure levels of ultraviolet light that each of the one or more subjects is exposed to over a particular time period.

In some implementations, the processor is also configured to process data that represents information about the levels of ultraviolet light that each of the one or more subjects is exposed to over the particular time period.

In some implementations, the processor is also configured to determine an amount of time that each of the one or more subjects has spent outside over the particular time period based on the information about the levels of ultraviolet light.

In some implementations, determining the quality of care provided to the one or more subjects includes determining a level of physical activity experienced by each of the one or more subjects by comparing gross motion data of each subject to a threshold value.

In another aspect, a method includes processing data in a first dataset that represents time-varying information about at least one pulse pressure wave propagating through blood in a subject acquired at a location of the subject. The data is acquired while the subject is in a situation associated with risk indicated by the data.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The data is acquired while the subject is in a situation associated with risk indicated by the data.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a processor configured to receive data from one or both of the light-emitting element and the optical sensor. The processor is also configured to process the data to determine whether the subject is in a situation associated with risk and to derive a measure of a level of risk associated with the subject.

Implementations can include one or more of the following features.

In some implementations, the method also includes processing data in a second dataset that represents time-varying information about motion of the subject acquired at the location of the subject.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the method also includes using the processed data to derive a measure of a level of risk associated with the subject.

In some implementations, the method also includes identifying a first point in the first dataset, the first point representing an arrival time of the pulse pressure wave at a first body part of the subject. The method also includes identifying a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject.

In some implementations, the first body part is the location of the subject at which the data in the first data set is acquired, and the second body part is the heart of the subject.

In some implementations, the method also includes determining a blood pressure of the subject based on the PTT.

In some implementations, the risk includes trauma to the subject and the data is indicative of the existence of the trauma.

In some implementations, the method also includes providing the processed data to a party that is responding to the trauma.

In some implementations, the processed data is transmitted from a device worn by the subject to a remote device.

In some implementations, the remote device is a server associated with an emergency service provider.

In some implementations, the processed data is provided to the party before the party has reached the subject.

In some implementations, the method also includes processing data that represents time-varying information about at least one pulse pressure wave propagating through blood in additional subjects acquired at a location of each of the subjects. The method also includes processing data that represents time-varying information about motion of the additional subjects acquired at the location of each of the subjects. The data is acquired while the additional subjects are in the situation associated with the risk, and the risk includes trauma.

In some implementations, the method also includes providing the processed data for the subject and the additional subjects to a party that is responding to the trauma, before the party has reached the subjects.

In some implementations, the processed data is transmitted from devices worn by the subjects to a remote device.

In some implementations, the remote device is a server associated with an emergency service provider.

In some implementations, the method also includes providing information to the party that enables the party to assess a level of risk associated with each of the subjects before the party has reached the subjects.

In some implementations, the method also includes providing the processed data to a medical facility to which the subject is taken for medical care.

In some implementations, the risk includes trauma.

In some implementations, providing the processed data to a medical facility includes providing the processed data to an urgent care division of the medical facility.

In some implementations, the information is provided to the urgent care division before the subject is treated by the urgent care division.

In some implementations, the method also includes processing data that represents time-varying information about at least one pulse pressure wave propagating through blood in additional subjects acquired at a location of each of the subjects. The method also includes processing data that represents time-varying information about motion of the additional subjects acquired at the location of each of the subjects. The data is acquired while the additional subjects are in the situation associated with the risk.

In some implementations, providing the processed data to a medical facility includes providing the processed data to an urgent care division of the medical facility.

In some implementations, the information is provided to the urgent care division before one or more of the subjects are treated by the urgent care division.

In some implementations, the subjects are treated in an order that is based on a severity of an injury.

In some implementations, relatively more severely injured subjects are treated before relatively less severely injured subjects.

In some implementations, the processed data is used to determine the subject's compliance with a particular standard of care throughout a progression of steps of the standard of care.

In some implementations, the processed data is used to determine whether the subject is receiving care that is appropriate according to a particular standard of care.

In some implementations, the data is processed after the subject is in the situation associated with risk.

In some implementations, the processing of the data occurs after the data has been acquired and with a short enough delay to enable an effect of the risk to be resolved.

In some implementations, the situation includes firefighting.

In some implementations, the situation includes a natural disaster or a sudden act of violence.

In some implementations, the risk includes one or more of heart failure, emotional stress, abnormal skin temperature, abnormal body temperature, hypertension, heart attack, stroke, arrhythmia, exhaustion, and anxiety.

In some implementations, the method also includes determining one or more of a blood pressure, a skin temperature, a body temperature, a heart rate, and a heart rate variability of the subject based on the datasets. The method also includes detecting emotional stress in the subject by determining whether one or more of the determined blood pressure, heart rate, and heart rate variability of the subject is a predetermined amount above a threshold.

In some implementations, the data indicates that the subject is about to experience an effect of one of the risks.

In some implementations, the risk includes overexposure of the subject to ultraviolet light.

In some implementations, the method also includes processing data that represents information about an amount of ultraviolet light that the subject has been exposed to.

In some implementations, the method also includes comparing the amount of ultraviolet light that the subject has been exposed to a threshold to determine whether the subject has been overexposed to ultraviolet light.

In some implementations, the method also includes alerting the subject if the subject has been overexposed to ultraviolet light.

In some implementations, the risk includes trauma to the subject and the data is indicative of the existence of the trauma.

In some implementations, the operations also include processing data in a second dataset that represents time-varying information about motion of the subject acquired at the location of the subject.

In some implementations, the device also includes a motion sensor configured to provide data that represents time-varying information about motion of the subject acquired by the motion sensor at the location of the subject. The processor is also configured to receive and process the data from the motion sensor.

In some implementations, the processor is also configured to cause the biofeedback device to provide the processed data to a party that is responding to the trauma.

In some implementations, the processor is also configured to cause the biofeedback device to provide the processed data to a remote device.

In some implementations, the remote device is a server associated with an emergency service provider.

In some implementations, the processor is also configured to cause the biofeedback device to provide the processed data to a medical facility to which the subject is taken for medical care.

In some implementation, the device also includes a transceiver configured to provide the processed data.

In some implementations, the processed data is used to determine the subject's compliance with a particular standard of care throughout a progression of steps of the standard of care.

In some implementations, the processed data is used to determine whether the subject is receiving care that is appropriate according to a particular standard of care.

In some implementations, the risk includes overexposure of the subject to ultraviolet light.

In some implementations, the device also includes an ultraviolet light sensor configured to measure an amount of ultraviolet light that the subject is exposed to.

In some implementations, the processor is also configured to process data that represents information about the amount of ultraviolet light that the subject is exposed to.

In some implementations, the processor is also configured to compare the amount of ultraviolet light that the subject is exposed to a threshold to determine whether the subject has been overexposed to ultraviolet light.

In some implementations, the device is also configured to alert the subject if the subject has been overexposed to ultraviolet light.

In another aspect, a method includes processing data in a first dataset that represents time-varying information about at least one pulse pressure wave propagating through blood in a subject acquired at a location of the subject. The method also includes providing information related to the data to a remote device.

In another aspect, a system includes a remote device and a biofeedback device configured to be worn by a subject. The biofeedback device includes a light source configured to emit light toward the skin of the subject. The biofeedback device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The biofeedback device also includes a processor configured to receive data from one or both of the light-emitting element and the optical sensor. The processor is also configured to provide information related to the data to a remote device.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include providing information related to the data to a remote device.

In another aspect, a biofeedback device configured to be worn by a subject includes a light source configured to emit light toward the skin of the subject. The biofeedback device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The biofeedback device also includes a processor configured to receive data from one or both of the light-emitting element and the optical sensor. The processor is also configured to provide information related to the data to a remote device.

Implementations can include one or more of the following features.

In some implementations, the method also includes processing data in a second dataset that represents time-varying information about motion of the subject acquired at the location of the subject.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the remote device is a server.

In some implementations, the method also includes determining, based on the data in the first and second datasets, that the subject is experiencing or has experienced a health-related problem.

In some implementations, the method also includes causing the remote device to alert one or both of a caregiver and the subject that the subject is experiencing or has experienced a health-related problem.

In some implementations, the method also includes causing the remote device to alert the subject that the subject is experiencing a health-related problem.

In some implementations, the remote device sends an alert to a device worn by the subject that acquires the data.

In some implementations, the remote device sends an alert to a mobile phone of the subject.

In some implementations, determining that the subject is experiencing or has experienced a health-related problem includes determining whether a blood pressure of the subject satisfies a threshold.

In some implementations, wherein the health-related problem is hypertension.

In some implementations, determining that the subject is experiencing or has experienced a health-related problem includes determining a rate of change of a blood pressure of the subject.

In some implementations, the medical event is a stroke, and the subject is determined to be having a stroke if the rate of change of the blood pressure of the subject is positive and above a threshold.

In some implementations, the medical event is abnormal heart function, and the subject is determined to be experiencing abnormal heart function if the rate of change of the blood pressure of the subject is negative and below a threshold.

In some implementations, the method also includes identifying a first point in the first dataset, the first point representing an arrival time of the pulse pressure wave at a first body part of the subject. The method also includes identifying a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject.

In some implementations, the blood pressure of the subject is determined based on the PTT.

In some implementations, the first body part is the location of the subject at which the data in the first data set is acquired, and the second body part is the heart of the subject.

In some implementations, determining that the subject is experiencing a health-related problem includes determining whether a heart rate of the subject satisfies a threshold.

In some implementations, the health-related problem is tachycardia.

In some implementations, determining the heart rate of the subject includes calculating a distance between two consecutive reference points in the first dataset, the distance representing a time that has elapsed between two consecutive heartbeats of the subject.

In some implementations, the reference points are local maxima or local minima.

In some implementations, the reference points are peaks or valleys in the first dataset.

In some implementations, determining that the subject is experiencing a health-related problem includes determining whether a heart rate variability of the subject satisfies a threshold.

In some implementations, the threshold is based on whether the subject experiences arrhythmia.

In some implementations, determining the heart rate variability of the subject includes calculating distances between multiple pairs of consecutive reference points in the first dataset, each distance representing a time that has elapsed between two consecutive heartbeats of the subject.

In some implementations, the reference points are local maxima or local minima.

In some implementations, the reference points are peaks or valleys.

In some implementations, determining that the subject has experienced a health-related problem includes determining whether the subject has sustained an impact of a magnitude that satisfies a threshold.

In some implementations, determining the magnitude of the impact includes analyzing gross motion data of the subject at the time of the impact.

In some implementations, the health-related problem is a concussion.

In some implementations, the method also includes determining, based on the data in the first and second datasets, that the subject is about to experience a health-related problem.

In some implementations, the method also includes causing the remote device to alert a caregiver that the subject is about to experience a health-related problem.

In some implementations, the method also includes causing the remote device to alert the subject that the subject is about to experience a health-related problem.

In some implementations, the remote device sends an alert to a device worn by the subject that acquires the data.

In some implementations, the remote device sends an alert to a mobile phone of the subject.

In some implementations, determining that the subject is about to experience a health-related problem includes determining whether a blood pressure of the subject satisfies a threshold.

In some implementations, the method also includes identifying a first point in the first dataset, the first point representing an arrival time of the pulse pressure wave at a first body part of the subject. The method also includes identifying a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject.

In some implementations, the blood pressure of the subject is determined based on the PTT.

In some implementations, the first body part is the location of the subject at which the data in the first data set is acquired, and the second body part is the heart of the subject.

In some implementations, determining that the subject is about to experience a health-related problem includes determining whether a heart rate of the subject satisfies a threshold.

In some implementations, determining the heart rate of the subject includes calculating a distance between two consecutive reference points in the first dataset, the distance representing a time that has elapsed between two consecutive heartbeats of the subject.

In some implementations, the reference points are local maxima or local minima.

In some implementations, the reference points are peaks or valleys in the first dataset.

In some implementations, determining that the subject is about to experience a health-related problem includes determining whether a heart rate variability of the subject satisfies a threshold.

In some implementations, determining the heart rate variability of the subject includes calculating distances between multiple pairs of consecutive reference points in the first dataset, each distance representing a time that has elapsed between two consecutive heartbeats of the subject.

In some implementations, the reference points are local maxima or local minima.

In some implementations, the reference points are peaks or valleys.

In some implementations, the method also includes providing location information related to the subject to the remote device.

In some implementations, the location information is provided by a location module of a device worn by the subject that acquires the data.

In some implementations, the location module is a GPS transponder.

In some implementations, the method also includes providing temperature information related to the subject to the remote device.

In some implementations, the remote device is a thermostat.

In some implementations, the subject is remote from a location that is temperature-controlled by the thermostat.

In some implementations, the thermostat is configured to adjust its temperature settings based on the temperature information related to the subject.

In some implementations, a time when the thermostat adjusts its temperature settings is based on the location information related to the subject.

In some implementations, the thermostat adjusts its temperature settings when the location information indicates that the subject is within a predefined distance from a location that is temperature-controlled by the thermostat.

In some implementations, the remote device is a light.

In some implementations, the subject is remote from a location that can be illuminated by the light.

In some implementations, the light is configured to adjust its lighting settings at a time that is based on the location information related to the subject.

In some implementations, the light adjusts its lighting settings when the location information indicates that the subject is within a predefined distance from a location that is lighting-controlled by the light.

In some implementations, the method also includes determining that the subject is interacting with a particular object based on a location of the subject.

In some implementations, the remote device is a server.

In some implementations, the particular object is an advertisement.

In some implementations, the particular object is a product display.

In some implementations, the particular object is a retail product.

In some implementations, the location of the subject is determined by a GPS module of a device worn by the subject that acquires the data.

In some implementations, the location of the subject is determined based on a strength of a wireless connection between a device worn by the subject that acquires the data and one or more proximity sensors.

In some implementations, a relatively higher strength of the wireless connection between the device and the proximity sensor indicates that the device is relatively closer to the proximity sensor.

In some implementations, the wireless connection is a Bluetooth connection.

In some implementations, the method also includes determining, based on the processed data, that the subject is experiencing one or more of an increase in heart rate, blood pressure, and respiratory rate while the subject is interacting with the particular object.

In some implementations, the method also includes inferring that the subject is interested in the particular object based on one or more of the heart rate, the blood pressure, and the respiratory rate of the subject while the subject is interacting with the particular object.

In some implementations, the remote device is an entertainment device.

In some implementations, the entertainment device is a television.

In some implementations, the entertainment device is an audio output device.

In some implementations, the entertainment device is a gaming device.

In some implementations, the processed data indicates whether the subject has exercised for a predetermined length of time, and the entertainment device can be turned on only if the subject has exercised for the predetermined length of time.

In some implementations, the entertainment device is configured to provide content personalized for the subject based on a state of the subject as determined from the processed data.

In some implementations, the state of the subject includes a level of interest in the content provided by the entertainment device.

In some implementations, a rise in one or more of a heart rate, a heart rate variability, an electrical skin impedance, a respiratory rate, and a blood pressure of the subject while the subject is experiencing the content indicates an increased level of interest in the content.

In some implementations, the heart rate, the heart rate variability, the electrical skin impedance, and the respiratory rate of the subject are determined from the processed data.

In some implementations, the method also includes processing data in a second dataset that represents time-varying information about motion of the subject acquired at the location of the subject. The blood pressure of the subject is determined from the processed data.

In some implementations, the entertainment device provides content designed to excite the subject if the heart rate variability of the subject is within a predefined range.

In some implementations, the entertainment device provides content designed to excite the subject if one or more of the heart rate, the electrical skin impedance, the respiratory rate, and the blood pressure of the subject is below a respective threshold.

In some implementations, the state of the subject includes a level of stress of the subject while the subject is experiencing the content.

In some implementations, a rise in one or more of a heart rate, a heart rate variability, an electrical skin impedance, a respiratory rate, and a blood pressure of the subject while the subject is experiencing the content indicates an increased level of interest in the content.

In some implementations, the heart rate, the heart rate variability, the electrical skin impedance, and the respiratory rate of the subject are determined from the processed data.

In some implementations, the method also includes processing data in a second dataset that represents time-varying information about motion of the subject acquired at the location of the subject, wherein the blood pressure of the subject is determined from the processed data.

In some implementations, the entertainment device provides content designed to calm the subject if the heart rate variability of the subject is within a predefined range.

In some implementations, the entertainment device provides content designed to calm the subject if one or more of the heart rate, the electrical skin impedance, the respiratory rate, and the blood pressure of the subject is above a respective threshold.

In some implementations, the entertainment device is a television and the content includes one or more of television shows, movies, and games.

In some implementations, the entertainment device is a gaming device that is configured to adjust game settings based on a state of the subject as determined from the processed data.

In some implementations, game settings include one or more of difficulty settings, sound settings, and situational settings.

In some implementations, the entertainment device is configured to turn off based on a state of the subject as determined from the processed data.

In some implementations, the method also includes causing the remote device to adjust a dating preference in a dating profile of the subject based on a state of the subject as determined from the processed data.

In some implementations, the method also includes processing data that represents time-varying information about at least one pulse pressure wave propagating through blood in one or more other subjects acquired at locations on the other subjects. The method also includes processing data that represents time-varying information about motion of the one or more other subjects acquired at the locations on the other subjects. The method also includes determining a compatibility between the subject and each of the other subjects based on states of the subjects as determined from the data.

In some implementations, the method also includes ranking the compatibilities between the subject and each of the other subjects.

In some implementations, the remote device is a device operated by the subject.

In some implementations, the method also includes determining, based on the data in the first and second datasets, that the subject is not adequately alert.

In some implementations, determining that the subject is not adequately alert is based on one or more of a heart rate, a respiratory rate, a blood pressure, and an activity level of the subject.

In some implementations, determining that the subject is not adequately alert includes determining, based on the processed data, whether one or more of the heart rate, the respiratory rate, the blood pressure, and the activity level of the subject is below a threshold.

In some implementations, the method also includes causing the device to activate an alarm if the subject is not adequately alert.

In some implementations, the method also includes causing the device to slow down if the subject is not adequately alert.

In some implementations, the device is a vehicle.

In some implementations, the data is acquired by the device and the device is wearable by the subject.

In some implementations, the method also includes causing an alarm of the wearable device to be activated if the subject is not adequately alert.

In some implementations, the biofeedback device also includes a motion sensor configured to provide data that represents time-varying information about motion of the subject acquired by the motion sensor at the location of the subject. The processor is also configured to receive data from the motion sensor.

In some implementations, the operations also include processing data in a second dataset that represents time-varying information about motion of the subject acquired at the location of the subject.

In some implementations, the biofeedback device also includes a motion sensor configured to provide data that represents time-varying information about motion of the subject acquired by the motion sensor at the location of the subject. The processor is also configured to receive data from the motion sensor.

In some implementations, the processor is also configured to determine, based on the received data, that the subject is experiencing or has experienced a health-related problem.

In some implementations, the processor is also configured to determine, based on the received data, that the subject is about to experience a health-related problem.

In some implementations, the processor is also configured to cause the remote device to alert a caregiver that the subject is experiencing, has experienced, or is about to experience a health-related problem.

In some implementations, the processor is also configured to cause the remote device to alert the subject that the subject is experiencing, has experienced, or is about to experience a health-related problem.

In some implementations, the remote device sends an alert to the biofeedback device.

In some implementations, the remote device sends an alert to a mobile phone of the subject.

In some implementations, the processor is also configured to provide location information related to the subject to the remote device.

In some implementation, the biofeedback device also includes a location module configured to provide the location information related to the subject to the remote device.

In some implementations, the location module is a GPS transponder.

In some implementations, the processor is also configured to provide temperature information related to the subject to the remote device.

In some implementations, the processor is also configured to determine that the subject is interacting with a particular object based on a location of the subject.

In some implementations, the remote device is a server.

In some implementations, the particular object is an advertisement.

In some implementations, the particular object is a product display.

In some implementations, the particular object is a retail product.

In some implementations, the location of the subject is determined by the GPS module of the biofeedback device.

In some implementations, the location of the subject is determined based on a strength of a wireless connection between the biofeedback device and one or more proximity sensors.

In some implementations, a relatively higher strength of the wireless connection between the biofeedback device and the proximity sensor indicates that the biofeedback device is relatively closer to the proximity sensor.

In some implementations, the wireless connection is a Bluetooth connection.

In some implementations, the remote device is a device operated by the subject.

In some implementations, the processor is also configured to determine, based on the received data, that the subject is not adequately alert.

In some implementations, the processor is also configured to cause the biofeedback device to activate an alarm if the subject is not adequately alert.

In some implementations, the processor is also configured to cause the device operated by the subject to slow down if the subject is not adequately alert.

In some implementations, the device is a vehicle.

In another aspect, a method includes deriving a score associated with a state of a subject, the state of the subject being one or more members selected from the group consisting of health, sleep, fitness, and stress. Deriving the score is based on data in a first dataset that represents time-varying information about at least one pulse pressure wave propagating through blood in the subject acquired at a location of the subject.

In another aspect, one or more machine-readable storage devices stores instructions that are executable by one or more processing devices to perform operations including deriving a score associated with a state of a subject. The state of the subject is one or more members selected from the group consisting of health, sleep, fitness, and stress. Deriving the score is based on data in a first dataset that represents time-varying information about at least one pulse pressure wave propagating through blood in the subject acquired at a location of the subject.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to derive a score associated with a state of the subject, the state of the subject being one or more members selected from the group consisting of health, sleep, fitness, and stress.

Implementations can include one or more of the following features.

In some implementations, deriving the score is also based on data in a second dataset that represents time-varying information about motion of the subject acquired at the location of the subject.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the score is a numerical value.

In some implementations, the numerical value is between 1 and 100.

In some implementations, the numerical value is between 1 and 10.

In some implementations, the data is acquired by a device that is worn by the subject and that displays the score.

In some implementations, the device worn by the subject derives the score.

In some implementations, the device worn by the subject provides the data to a remote device that derives the score.

In some implementations, the remote device is a server.

In some implementations, the remote device provides the score to the device worn by the subject.

In some implementations, the remote device provides the score to a mobile phone of the subject.

In some implementations, the score is provided to one or both of the subject and another party.

In some implementations, the state of the subject includes a sleep state, and the score includes a sleep score.

In some implementations, the sleep score is associated with a level of quality of the subject's sleep.

In some implementations, deriving the score includes identifying one or more potential sleep rest periods of the subject based on gross motion data of the subject.

In some implementations, deriving the score also includes calculating one or more of an average heart rate, a standard deviation of the average heart rate, and an average heart rate variability of the subject during each of the one or more potential sleep rest periods based on the information about at least one pulse pressure wave propagating through blood in the subject.

In some implementations, one or more of the potential sleep rest periods are identified as sleep rest periods by comparing one or more of the average heart rate, the standard deviation of the average heart rate, and the average heart rate variability of the subject during the respective potential sleep rest period to a threshold.

In some implementations, the sleep state of the subject is associated with one or more of sleep duration, sleep latency, and sleep staging.

In some implementations, deriving the score includes determining one or more of the sleep duration, the sleep latency, and the sleep staging of the subject.

In some implementations, the method also includes determining the sleep duration of the subject.

In some implementations, determining the sleep duration of the subject includes determining a total length of time during which the subject was asleep based on information related to one or more sleep rest periods of the subject.

In some implementations, the information related to the one or more sleep rest periods includes a time associated with a beginning of each sleep rest period, a time associated with an end of each sleep rest period, gross motion data of the subject during each sleep rest period, and heart rate data of the subject during each sleep rest period.

In some implementations, determining the sleep duration of the subject includes determining a percentage of time that the subject was asleep between a time when the subject started to try to fall asleep and a time when the subject awoke based on information related to one or more sleep rest periods of the subject and gross motion data of the subject before the subject fell asleep.

In some implementations, the method also includes determining the sleep latency of the subject.

In some implementations, determining the sleep latency of the subject includes determining a length of time that it takes for the subject to transition from a state of wakefulness to the sleep state based on information related to one or more sleep rest periods of the subject and gross motion data of the subject before the subject fell asleep.

In some implementations, the method also includes determining the sleep staging of the subject.

In some implementations, determining the sleep staging of the subject includes determining a deepness of the subject's sleep during a portion of each of one or more sleep rest periods of the subject based on information related to the one or more sleep rest periods.

In some implementations, the sleep staging of the subject is determined based on at least a heart rate and gross motion data of the subject during one or more of the portions of the sleep rest periods.

In some implementations, the data is acquired by a device that is worn by the subject.

In some implementations, the method also includes causing the device to calculate and display the sleep score when the subject is determined to have awoken.

In some implementations, the method also includes providing information to the subject that assists the subject in improving the sleep score.

In some implementations, the information includes a recommended sleep schedule.

In some implementations, the information is provided to a device that is worn by the subject that acquires the data.

In some implementations, the information is provided to a mobile phone of the subject.

In some implementations, the state of the subject includes a fitness state, and the score includes a fitness score.

In some implementations, the fitness score is associated with one or more of a degree of physical fitness, cardiac condition, coaching, dehydration, social interaction, adherence to a regimen, and coaching effectiveness of the subject.

In some implementations, deriving the score includes calculating a resting heart rate of the subject while the subject is inactive based on the information about at least one pulse pressure wave propagating through blood in the subject and gross motion data of the subject.

In some implementations, deriving the score also includes calculating a heart rate of the subject based on the information about at least one pulse pressure wave propagating through blood in the subject. Deriving the score also includes determining that the subject is in the fitness state based on the heart rate and the gross motion data of the subject.

In some implementations, deriving the score includes determining a length of time that it takes for the subject's heart rate to transition from the heart rate in the fitness state to the resting heart rate.

In some implementations, deriving the score includes determining a length of time that it takes for the subject's heart rate to transition from the resting heart rate to the heart rate in the fitness state.

In some implementations, the data is acquired by a device that is worn by the subject.

In some implementations, the method also includes causing the device to calculate and display the fitness score when the subject is determined to be in the fitness state.

In some implementations, the method also includes causing the device to calculate and display the fitness score when the subject is determined to have transitioned from the fitness state to a non-fitness state.

In some implementations, the method also includes providing information to the subject that assists the subject in improving the fitness score.

In some implementations, the information includes a recommended fitness routine.

In some implementations, the information is provided to a device that is worn by the subject that acquires the data.

In some implementations, the information is provided to a mobile phone of the subject.

In some implementations, the method also includes embedding a visual indication of one or more of the fitness score, a heart rate, a respiratory rate, and a blood pressure of the subject into a video showing the subject performing a fitness routine.

In some implementations, the visual indications are updated throughout the video according to the fitness score, the heart rate, the respiratory rate, and the blood pressure of the subject during the fitness routine.

In some implementations, the method also includes predicting an outcome of an athletic event that the subject is participating in based on one or more of the fitness score, a heart rate, a respiratory rate, and a blood pressure of the subject during the athletic event.

In some implementations, the method also includes comparing one or more of the fitness score, the heart rate, the respiratory rate, and the blood pressure of the subject to fitness scores, heart rates, respiratory rates, and blood pressures of other individuals who are participating in the athletic event.

In some implementations, the method also includes, while the subject is performing physical activity, comparing one or more of the fitness score, a heart rate, a respiratory rate, and a blood pressure of the subject to fitness scores, heart rates, respiratory rates, and blood pressures of one or more individuals who have previously performed the physical activity.

In some implementations, performing the physical activity includes performing an athletic event, and the one or more individuals are professional athletes who compete in the athletic event.

In some implementations, the state of the subject includes a stress state, and the score includes a stress score.

In some implementations, deriving the score includes calculating one or more of a heart rate, a heart rate variability, a blood pressure, an electrical skin impedance, and a respiratory rate of the subject based on the information about at least one pulse pressure wave propagating through blood in the subject and information about motion of the subject.

In some implementations, the stress state of the subject is associated with hypertension, and deriving the score includes determining whether the subject is experiencing hypertension by comparing a blood pressure of the subject to a threshold.

In some implementations, the stress state of the subject is associated with emotional stress, and deriving the score includes determining a level of emotional stress experienced by the subject by comparing one or more of a heart rate, a heart rate variability, a blood pressure, an electrical skin impedance, and a respiratory rate of the subject to a threshold.

In some implementations, determining the level of emotional stress experienced by the subject is based at least in part on audio data.

In some implementations, the audio data is captured by a microphone of a device that acquires the data in the first dataset.

In some implementations, the audio data includes one or both of environmental noise and a tonality of the subject's voice.

In some implementations, determining the level of emotional stress experienced by the subject includes analyzing the environmental noise to determine whether the subject is in an environment attributed to an increased emotional stress level.

In some implementations, determining the level of emotional stress experienced by the subject includes analyzing the tonality of the subject's voice to determine whether the subject is in a confrontational situation attributed to an increased emotional stress level.

In some implementations, the data is acquired by a device that is worn by the subject.

In some implementations, the method also includes causing the device to calculate and display the stress score when the subject is determined to be in the stress state.

In some implementations, the method also includes providing information to the subject that assists the subject in improving the stress score.

In some implementations, the information includes a recommended stress-reducing routine.

In some implementations, the information is provided to a device that is worn by the subject that acquires the data.

In some implementations, the information is provided to a mobile phone of the subject.

In some implementations, the state of the subject includes a sleep state, and the score includes a sleep score.

In some implementations, the sleep state of the subject is associated with one or more of sleep duration, sleep latency, and sleep staging, and deriving the score includes determining one or more of the sleep duration, the sleep latency, and the sleep staging of the subject.

In some implementations, the processor is also configured to determine the sleep duration of the subject.

In some implementations, determining the sleep duration of the subject includes determining a total length of time during which the subject was asleep based on information related to one or more sleep rest periods of the subject.

In some implementations, determining the sleep duration of the subject includes determining a percentage of time that the subject was asleep between a time when the subject started to try to fall asleep and a time when the subject awoke based on information related to one or more sleep rest periods of the subject and gross motion data of the subject before the subject fell asleep.

In some implementations, the processor is also configured to determine the sleep latency of the subject.

In some implementations, determining the sleep latency of the subject includes determining a length of time that it takes for the subject to transition from a state of wakefulness to the sleep state based on information related to one or more sleep rest periods of the subject and gross motion data of the subject before the subject fell asleep.

In some implementations, the processor is also configured to determine the sleep staging of the subject.

In some implementations, determining the sleep staging of the subject includes determining a deepness of the subject's sleep during a portion of each of one or more sleep rest periods of the subject based on information related to the one or more sleep rest periods.

In some implementations, the sleep staging of the subject is determined based on at least a heart rate and gross motion data of the subject during one or more of the portions of the sleep rest periods.

In some implementations, the biofeedback device also includes a display, and the processor is also configured to cause the display to display the sleep score.

In some implementations, the processor causes the display to display the sleep score when the subject is determined to have awoken.

In some implementations, the state of the subject includes a fitness state, and the score includes a fitness score.

In some implementations, the fitness score is associated with one or more of a degree of physical fitness, cardiac condition, coaching, dehydration, social interaction, adherence to a regimen, and coaching effectiveness of the subject.

In some implementations, deriving the score includes calculating a resting heart rate of the subject while the subject is inactive based on the information about at least one pulse pressure wave propagating through blood in the subject and gross motion data of the subject.

In some implementations, deriving the score also includes calculating a heart rate of the subject based on the information about at least one pulse pressure wave propagating through blood in the subject. Deriving the score also includes determining that the subject is in the fitness state based on the heart rate and the gross motion data of the subject.

In some implementations, deriving the score also includes determining a length of time that it takes for the subject's heart rate to transition from the heart rate in the fitness state to the resting heart rate.

In some implementations, deriving the score also includes determining a length of time that it takes for the subject's heart rate to transition from the resting heart rate to the heart rate in the fitness state.

In some implementations, the processor is also configured to cause the display to display the fitness score.

In some implementations, the processor causes the display to display the fitness score when the subject is determined to be in the fitness state.

In some implementations, the processor causes the display to display the fitness score when the subject is determined to have transitioned from the fitness state to a non-fitness state.

In some implementations, the processor is also configured to determine one or more of a heart rate, a respiratory rate, and a blood pressure of the subject based on data received from one or more of the light-emitting element, the optical sensor, and the motion sensor.

In some implementations, the device also includes a transceiver, and the processor is configured to cause the transceiver to provide one or more of the fitness score, the heart rate, the respiratory rate, and the blood pressure of the subject to a remote device.

In some implementations, the processor causes the transceiver to provide one or more of the fitness score, the heart rate, the respiratory rate, and the blood pressure of the subject to a video that shows the subject performing a fitness routine. A visual indication of one or more of the fitness score, the heart rate, the respiratory rate, and the blood pressure of the subject is embedded into the video.

In some implementations, the visual indications are updated throughout the video according to the fitness score, the heart rate, the respiratory rate, and the blood pressure of the subject during the fitness routine.

In some implementations, the processor is also configured to predict an outcome of an athletic event that the subject is participating in based on one or more of the fitness score, the heart rate, the respiratory rate, and the blood pressure of the subject during the athletic event.

In some implementations, the transceiver is configured to communicate with transceivers of other biofeedback devices.

In some implementations, the processor is also configured to compare one or more of the fitness score, the heart rate, the respiratory rate, and the blood pressure of the subject to fitness scores, heart rates, respiratory rates, and blood pressures of other individuals who are participating in the athletic event.

In some implementations, the processor is also configured to, while the subject is performing physical activity, compare one or more of the fitness score, the heart rate, the respiratory rate, and the blood pressure of the subject to fitness scores, heart rates, respiratory rates, and blood pressures of one or more individuals who have previously performed the physical activity.

In some implementations, performing the physical activity includes performing an athletic event, and the one or more individuals are professional athletes who compete in the athletic event.

In some implementations, the state of the subject includes a stress state, and the score includes a stress score.

In some implementations, the stress state of the subject is associated with emotional stress, and deriving the score includes determining a level of emotional stress experienced by the subject by comparing one or more of a heart rate, a heart rate variability, a blood pressure, an electrical skin impedance, and a respiratory rate of the subject to a threshold.

In some implementations, the biofeedback device also includes an audio input device.

In some implementations, determining the level of emotional stress experienced by the subject is based at least in part on audio data provided to the processor by the audio input device.

In some implementations, the audio data includes one or both of environmental noise and a tonality of the subject's voice.

In some implementations, determining the level of emotional stress experienced by the subject includes analyzing the environmental noise to determine whether the subject is in an environment attributed to an increased emotional stress level In some implementations, determining the level of emotional stress experienced by the subject includes analyzing the tonality of the subject's voice to determine whether the subject is in a confrontational situation attributed to an increased emotional stress level.

In some implementations, the processor is also configured to cause the display to display the stress score.

In some implementations, the processor causes the display to display the stress score when the subject is determined to be in the stress state.

In another aspect, a method includes processing data in a first dataset that represents time-varying information about at least one pulse pressure wave propagating through blood in a subject acquired at a location of the subject. The method also includes processing data in a second dataset that represents time-varying information about motion of the subject acquired at the location of the subject. The method also includes deriving information about a psychological state of the subject from the processed data.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include processing data in a second dataset that represents time-varying information about motion of the subject acquired at the location of the subject. The operations also include deriving information about a psychological state of the subject from the processed data.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to derive information about a psychological state of the subject from the processed data.

Implementations can include one or more of the following features.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the psychological state of the subject includes a state of stress.

In some implementations, the method also includes determining one or more of a blood pressure, a heart rate, and a heart rate variability of the subject based on the datasets. The method also includes deriving information about the state of stress of the subject based on one or more of the determined blood pressure, heart rate, and heart rate variability of the subject.

In some implementations, the method also includes correlating a level of stress of the subject to an amount of ultraviolet light that the subject has been exposed to.

In some implementations, deriving the information includes inferring a relationship between at least some of the processed data and one psychological state of the subject.

In some implementations, the method also includes inferring an existence of a second psychological state of the subject by comparing other processed data with the processed data related to the one psychological state.

In some implementations, the one psychological state includes a state of relatively lower stress.

In some implementations, the one psychological state includes a baseline state of the subject, and the relationship between at least some of the processed data and the one psychological state is inferred prior to the subject performing a polygraph test.

In some implementations, the psychological state includes a malicious intent.

In some implementations, the psychological state includes lying.

In some implementations, a device worn by the subject acquires the data.

In some implementations, deriving information about the psychological state of the subject includes determining a baseline state of the subject based on one or more of a blood pressure, a heart rate, a heart rate variability, a respiratory rate, and an electrical skin impedance.

In some implementations, the device is worn by the subject for an extended period of time to determine the baseline state of the subject.

In some implementations, the device is continuously worn by the subject for more than one day.

In some implementations, the processor is also configured to determine one or more of a blood pressure, a heart rate, and a heart rate variability of the subject based on the received data. The processor is also configured to derive information about a state of stress of the subject based on one or more of the determined blood pressure, heart rate, and heart rate variability of the subject.

In some implementations, the device also includes an ultraviolet light sensor configured to measure an amount of ultraviolet light that the subject is exposed to.

In some implementations, the processor is also configured to correlate a level of stress of the subject to an amount of ultraviolet light that the subject has been exposed to.

In another aspect, a method includes processing data in a dataset that represents time-varying information about at least one pulse pressure wave propagating through blood in a subject acquired at a location of the subject. The method also includes determining whether one or more segments of the dataset were captured from a subject other than an expected subject by analyzing morphological features of the segments.

In another aspect, a method includes processing data in a dataset that represents time-varying information about motion of a subject acquired at a location of the subject. The method also includes determining whether one or more segments of the dataset were captured from a subject other than an expected subject by analyzing morphological features of the segments.

In another aspect, a method includes processing data in a first dataset that represents time-varying information about at least one pulse pressure wave propagating through blood in a subject acquired at a location of the subject. The method also includes processing data in a second dataset that represents time-varying information about motion of the subject acquired at the location of the subject. The method also includes, based on the first and second datasets, determining at least two parameters of the subject, the parameters selected from the group consisting of blood pressure, respiratory rate, blood oxygen levels, heart rate, heart rate variability, stroke volume, cardiac output, MoCG morphology, and PPG morphology. The method also includes determining a biometric signature of the subject, the biometric signature represented by a multi-dimensional space that is defined by at least two axes, each axis corresponding to at least one of the determined parameters. The method also includes determining whether the biometric signature was captured from a subject who is an expected subject by analyzing features of the biometric signature.

In another aspect, one or more machine-readable storage devices stores instructions that are executable by one or more processing devices to perform operations including processing data in a dataset that represents time-varying information about at least one pulse pressure wave propagating through blood in a subject acquired at a location of the subject. The operations also include determining whether one or more segments of the dataset were captured from a subject other than an expected subject by analyzing morphological features of the segments.

In another aspect, one or more machine-readable storage devices stores instructions that are executable by one or more processing devices to perform operations including processing data in a dataset that represents time-varying information about motion of a subject acquired at a location of the subject. The operations also include determining whether one or more segments of the dataset were captured from a subject other than an expected subject by analyzing morphological features of the segments.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include processing data in a second dataset that represents time-varying information about motion of the subject acquired at the location of the subject. The operations also include determining at least two parameters of the subject based on the first and second datasets. The parameters are selected from the group consisting of blood pressure, respiratory rate, blood oxygen levels, heart rate, heart rate variability, stroke volume, cardiac output, MoCG morphology, and PPG morphology. The operations also include determining a biometric signature of the subject. The biometric signature is represented by a multi-dimensional space that is defined by at least two axes. Each axis corresponds to at least one of the determined parameters. The operations also include determining whether the biometric signature was captured from a subject who is an expected subject by analyzing features of the biometric signature.

In another aspect, a biofeedback device configured to be worn by a subject includes a light source configured to emit light toward the skin of the subject. The biofeedback device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The biofeedback device also includes a processor configured to receive data from one or both of the light-emitting element and the optical sensor. The processor is also configured to determine whether one or more segments of the data were captured from a subject other than an expected subject by analyzing morphological features of the segments.

Implementations can include one or more of the following features.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the determining includes analyzing other biometric data.

In some implementations, the other biometric data includes one or more of electrical skin impedance, respiratory rate, heart rate, heart rate variability, PPG morphology, and vocal sound frequency of the subject.

In some implementations, analyzing the other biometric data includes determining whether the subject is under distress.

In some implementations, the determining includes analyzing confidential information provided by the subject.

In some implementations, the confidential information includes one or more of a password, a personal identification number, and a predefined gesture.

In some implementations, the analyzing includes comparing morphological features of different segments of biometric data.

In some implementations, the method also includes taking an action when it is determined that one or more of the segments were captured from a subject other than the expected subject.

In some implementations, taking an action includes prompting the subject to provide confidential information to authenticate the subject as the expected subject.

In some implementations, the expected subject is a subject associated with a particular device that captures the data segments at a location on the expected subject.

In some implementations, the determining includes taking account of one or both of a changing level of activity and a changing heart rate of the subject.

In some implementations, the method also includes sending information to a device upon determining that the subject is the expected subject.

In some implementations, the device is a payment gateway, and the information includes a payment authorization.

In some implementations, the device is a lock, and the information causes a lock to unlock.

In some implementations, causing the lock to unlock is also based on a location of the subject.

In some implementations, the method also includes sending information to a device upon determining that the subject is under distress.

In some implementations, the subject is determined to be under distress if one or more of a heart rate, a blood pressure, and a respiratory rate of the subject surpasses a threshold.

In some implementations, the device is a payment gateway, and the information includes instructions for the payment gateway to prevent the subject from accessing the payment gateway.

In some implementations, the device is a lock, and the information includes instructions for the lock to remain locked.

In some implementations, the method also includes processing data in a second dataset that represents time-varying information about motion of the subject acquired at the location of the subject. The method also includes determining whether one or more segments of the datasets were captured from a subject other than an expected subject by analyzing morphological features of the segments.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the method also includes determining a pulse transit time (PTT) based on the datasets, the PTT representing a transit time of a pulse pressure wave within the subject.

In some implementations, the method also includes determining a blood pressure of the subject based on the datasets.

In some implementations, the determining includes analyzing other biometric data.

In some implementations, the other biometric data includes one or more of electrical skin impedance, respiratory rate, heart rate, heart rate variability, stroke volume, cardiac output, MoCG morphology, PPG morphology, and vocal sound frequency of the subject.

In some implementations, analyzing the other biometric data includes determining whether the subject is under distress.

In some implementations, the morphological features include differences in blood pressure at specific times during each of the data segments.

In some implementations, the specific times include times of peaks or valleys in blood pressure during the data segments.

In some implementations, the morphological features include differences in blood pressure at successive peaks of blood pressure, successive valleys of blood pressure, or successive peaks and valleys of blood pressure.

In some implementations, determining whether one or more segments of the data were captured from a subject other than an expected subject includes analyzing confidential information provided by the subject.

In some implementations, the confidential information includes one or more of a password, a personal identification number, and a predefined gesture.

In some implementations, the biofeedback device also includes a motion sensor configured to provide data that represents time-varying information about motion of the subject acquired by the motion sensor at the location of the subject. The processor is also configured to receive data from the motion sensor In some implementations, the processor is also configured to take an action when it is determined that one or more of the segments were captured from a subject other than the expected subject.

In some implementations, taking an action includes prompting the subject to provide confidential information to authenticate the subject as the expected subject.

In some implementations, the motion sensor is also configured to determine when a subject performs the predefined gesture.

In some implementations, the biofeedback device also includes a transceiver configured to send information to a device upon determining that the subject is the expected subject.

In some implementations, the device is a payment gateway, and the information includes a payment authorization.

In some implementations, the device is a lock, and the information causes a lock to unlock.

In some implementations, the biofeedback device also includes a location module, and causing the lock to unlock is also based on a location of the subject as determined by the location module.

In some implementations, the transceiver is also configured to send information to a device upon determining that the subject is under distress.

In some implementations, the device is a payment gateway, and the information includes instructions for the payment gateway to prevent the subject from accessing the payment gateway.

In some implementations, the device is a lock, and the information includes instructions for the lock to remain locked.

In another aspect, a method includes processing data in a first dataset that represents time-varying information about at least one pulse pressure wave propagating through blood in a subject acquired at a location of the subject. The method also includes providing, based on the data, information about a medication regimen of the subject.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include providing, based on the data, information about a medication regimen of the subject.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a processor configured to receive data from one or both of the light-emitting element and the optical sensor. The processor is also configured to provide, based on the data, information about a medication regimen of the subject.

Implementations can include one or more of the following features.

In some implementations, the method also includes processing data in a second dataset that represents time-varying information about motion of the subject acquired at the location of the subject.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the method also includes determining, based on the data, that the subject has potentially missed a dose of a medication. The method also includes providing a notification indicating that the subject has potentially missed the dose of the medication.

In some implementations, determining that the subject has potentially missed a dose of a medication includes determining that a blood pressure of the subject has crossed a threshold.

In some implementations, the method also includes identifying a first point in the first dataset, the first point representing an arrival time of the pulse pressure wave at a first body part of the subject. The method also includes identifying a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject. The blood pressure of the subject is determined based on the PTT.

In some implementations, the first body part is the location of the subject at which the data in the first data set is acquired, and the second body part is the heart of the subject.

In some implementations, determining that the subject has potentially missed a dose of a medication includes determining that a heart rate of the subject has crossed a threshold.

In some implementations, determining that the subject has potentially missed a dose of a medication includes determining that a respiratory rate of the subject has crossed a threshold.

In some implementations, the method also includes determining, based on the data, a reaction of the subject to a medication. The method also includes providing a recommended medication regimen of the medication based on the reaction of the subject to the medication.

In some implementations, the recommended medication regimen includes one or more recommended dosage timings. The recommended medication regimen also includes one or more recommended dosage amounts. Each of the recommended dosage amounts corresponds to one of the dosage timings.

In some implementations, determining a reaction of the subject to a medication includes determining a blood pressure of the subject.

In some implementations, the blood pressure of the subject is determined periodically.

In some implementations, the recommended dosage timings and amounts are determined so as to maintain a blood pressure of the subject within a defined range.

In some implementations, determining a reaction of the subject to a medication includes determining a heart rate of the subject.

In some implementations, the heart rate of the subject is determined periodically.

In some implementations, determining a reaction of the subject to a medication includes determining a regularity of a heart rate of the subject.

In some implementations, the recommended dosage timings and amounts are determined so as to maintain a heart rate of the subject within a defined range.

In some implementations, determining a reaction of the subject to a medication includes determining a cardiac output of the subject.

In some implementations, the recommended dosage timings and amounts are determined so as to maintain a cardiac output of the subject within a defined range.

In some implementations, determining a reaction of the subject to a medication includes determining a temperature of the subject.

In some implementations, the recommended dosage timings and amounts are determined so as to maintain the temperature of the subject within a defined range.

In some implementations, the recommended dosage timings and amounts are determined so as to maintain a heart rate of the subject within a defined range.

In some implementations, determining a reaction of the subject to a medication includes determining a respiratory rate of the subject.

In some implementations, the respiratory rate of the subject is determined periodically.

In some implementations, the recommended dosage timings and amounts are determined so as to maintain a respiratory rate of the subject within a defined range.

In some implementations, the biofeedback device also includes a motion sensor configured to provide data that represents time-varying information about motion of the subject acquired by the motion sensor at the location of the subject. The processor is also configured to receive data from the motion sensor.

In some implementations, the processor is also configured to determine, based on the data, that the subject has potentially missed a dose of a medication and provide a notification indicating that the subject has potentially missed the dose of the medication.

In some implementations, the processor is also configured to determine, based on the data, a reaction of the subject to a medication and provide a recommended medication regimen of the medication based on the reaction of the subject to the medication.

In some implementations, the recommended medication regimen includes one or more recommended dosage timings. The recommended medication regimen also includes one or more recommended dosage amounts, each of which corresponds to one of the dosage timings.

In some implementations, the operations also include processing data in a second dataset that represents time-varying information about motion of the subject acquired at the location of the subject In another aspect, a method includes processing data that represents time-varying information about at least one pulse pressure wave propagating through blood in each of two or more subjects acquired at a location of each of the subjects. The method also includes processing data that represents time-varying information about motion of the two or more subjects acquired at the location on each of the subject. The method also includes providing information to a user that reports relative states of the subjects.

In another aspect, one or more machine-readable storage devices stores instructions that are executable by one or more processing devices to perform operations including processing data that represents time-varying information about at least one pulse pressure wave propagating through blood in each of two or more subjects acquired at a location of each of the subjects. The operations also include processing data that represents time-varying information about motion of the two or more subjects acquired at the location on each of the subject. The operations also include providing information to a user that reports relative states of the subjects.

In another aspect, a biofeedback device configured to be worn by two or more subjects includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to provide information to a user that reports relative states of the subjects.

Implementations can include one or more of the following features.

In some implementations, the information about at least one pulse pressure wave propagating through blood in the subjects includes photoplethysmographic (PPG) data and the information about motion of the subjects includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at single locations of each of the subjects.

In some implementations, the data is acquired by devices worn by the subjects.

In some implementations, the devices are mobile and do not reduce mobility of the subjects.

In some implementations, the devices process the data.

In some implementations, the single location of each of the subjects is an arm of the subject.

In some implementations, the single location is a wrist of the subject.

In some implementations, the relative states of the subjects are determined based on one or more of respiratory rates, heart rates, and blood pressures of the subjects.

In some implementations, the relative states of the subjects are determined by comparing one or more of the respiratory rates, the heart rates, and the blood pressures of the subjects to respective threshold values.

In some implementations, devices worn by the subjects acquire the data, and the respiratory rates, the heart rates, and the blood pressures of the subjects are determined according to the data.

In some implementations, the method also includes managing the subjects based on the relative states.

In some implementations, the method also includes assigning tasks to the subjects based on the relative states of the subjects.

In some implementations, one or more of the subjects are put into an athletic contest according to the relative states of the subjects.

In some implementations, a subject is put into the athletic contest if one or more of the respiratory rate, the heart rate, and the blood pressure of the subject is above a respective threshold.

In some implementations, one or more of the subjects are assigned particular combat tasks according to the relative states of the subjects.

In some implementations, a subject is assigned a particular combat task if one or more of the respiratory rate, the heart rate, and the blood pressure of the subject is above a respective threshold.

In some implementations, the relative states include one or more of relative psychological states, relative physical states, and relative states of readiness.

In some implementations, the two or more subjects are managed based on the relative states.

In some implementations, the processor is also configured to assign tasks to the subjects based on the relative states of the subjects.

In some implementations, one or more of the subjects are put into an athletic contest according to the relative states of the subjects.

In some implementations, one or more of the subjects are assigned particular combat tasks according to the relative states of the subjects.

In another aspect, a method includes processing data in a first dataset that represents time-varying information about at least one pulse pressure wave propagating through blood in a subject acquired at a location of the subject while the subject is sleeping. The method also includes processing data in a second dataset that represents time-varying information about motion of the subject acquired at the location of the subject while the subject is sleeping. The method also includes determining, based on the data, information about a characteristic of the subject's sleep.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject while the subject is sleeping. The operations also include processing data in a second dataset that represents time-varying information about motion of the subject acquired at the location of the subject while the subject is sleeping. The operations also include determining, based on the data, information about a characteristic of the subject's sleep.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a motion sensor configured to provide data that represents time-varying information about motion of the subject acquired by the motion sensor at the location of the subject. The device also includes a processor configured to receive data from one or more of the light-emitting element, the optical sensor, and the motion sensor. The processor is also configured to determine, based on the data, information about a characteristic of the subject's sleep.

Implementations can include one or more of the following features.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the method also includes generating a reduced set of data by excluding data associated with non-sleep periods of the subject.

In some implementations, a period of time is identified as a non-sleep period based on gross motion data of the subject.

In some implementations, identifying the period of time as a non-sleep period includes determining that the gross motion data during the period of time is above a threshold.

In some implementations, identifying the period of time as a non-sleep period includes determining that the gross motion data during the period of time is substantially irregular.

In some implementations, a period of time is identified as a sleep period based on gross motion data of the subject.

In some implementations, identifying the period of time as a sleep period includes determining that the gross motion data during the period of time is below a threshold.

In some implementations, identifying the period of time as a sleep period includes determining that the gross motion data during the period of time is substantially flat.

In some implementations, the method also includes determining a start and an end of the sleep period.

In some implementations, determining the start of the sleep period includes identifying a time when the gross motion data falls below a threshold, and determining the end of the sleep period includes identifying a time when the gross motion data rises above a threshold.

In some implementations, the method also includes calculating a property of the sleep of the subject based on the data.

In some implementations, the property is associated with one or more of heart rate, heart rate variability, activity level, respiratory rate, and blood pressure of the subject.

In some implementations, one or more of the heart rate, the heart rate variability, the activity level, the respiratory rate, and the blood pressure of the subject are determined based on the processed data.

In some implementations, determining the heart rate of the subject includes calculating a distance between two consecutive reference points in the first dataset, the distance representing a time that has elapsed between two consecutive heartbeats of the subject.

In some implementations, the reference points are local maxima or local minima.

In some implementations, the reference points are peaks or valleys.

In some implementations, determining the heart rate variability of the subject includes calculating distances between multiple pairs of consecutive reference points in the first dataset, each distance representing a time that has elapsed between two consecutive heartbeats of the subject.

In some implementations, determining the blood pressure of the subject includes identifying a first point in the first dataset, the first point representing an arrival time of the pulse pressure wave at a first body part of the subject. Determining the blood pressure of the subject also includes identifying a second point in the second dataset, the second point representing an earlier time at which the pulse pressure wave traverses a second body part of the subject. Determining the blood pressure of the subject also includes computing a pulse transit time (PTT) as a difference between the first and second points, the PTT representing a time taken by the pulse pressure wave to travel from the second body part to the first body part of the subject, wherein the PTT is related to an internal pressure of one or more blood vessels of the subject. Determining the blood pressure of the subject also includes determining the blood pressure of the subject based on the internal pressure of the one or more blood vessels.

In some implementations, the first body part is the location of the subject at which the data in the first data set is acquired, and the second body part is the heart of the subject.

In some implementations, the characteristic of the subject's sleep is determined based on the property.

In some implementations, the characteristic includes sleep apnea.

In some implementations, determining that the subject is experiencing sleep apnea includes identifying a simple signal in a heart rate signal of the subject that is acquired during a sleep period of the subject.

In some implementations, determining that the subject is experiencing sleep apnea includes identifying recurring simple signals in the heart rate signal of the subject.

In some implementations, the simple signals recur at least every two minutes during the sleep period of the subject.

In some implementations, the characteristic includes a quality of the sleep, including one or more of a sleep duration, a sleep latency, a sleep staging, a number of disturbances, and a number of tosses and turns.

In some implementations, determining information about a characteristic of the subject's sleep includes determining the sleep duration of the subject.

In some implementations, determining the sleep duration of the subject includes determining a total length of time during which the subject was asleep based on information related to one or more sleep rest periods of the subject.

In some implementations, the information related to the one or more sleep rest periods includes a time associated with a beginning of each sleep rest period, a time associated with an end of each sleep rest period, gross motion data of the subject during each sleep rest period, and heart rate data of the subject during each sleep rest period.

In some implementations, determining information about a characteristic of the subject's sleep includes determining the sleep latency of the subject.

In some implementations, determining the sleep latency of the subject includes determining a length of time that it takes for the subject to transition from a state of wakefulness to the sleep state based on information related to one or more sleep rest periods of the subject and gross motion data of the subject before the subject fell asleep.

In some implementations, determining information about a characteristic of the subject's sleep includes determining the sleep staging of the subject.

In some implementations, determining the sleep staging of the subject includes determining a deepness of the subject's sleep during a portion of each of one or more sleep rest periods of the subject based on information related to the one or more sleep rest periods.

In some implementations, the sleep staging of the subject is determined based on at least a heart rate and gross motion data of the subject during one or more of the portions of the sleep rest periods.

In some implementations, the method also includes alerting the subject when the sleep duration exceeds a threshold while the subject is in a light sleep stage.

In some implementations, the characteristic includes a sleep disorder.

In some implementations, the characteristic includes a level of nocturnal dip of blood pressure.

In some implementations, the characteristic includes a sleep period.

In some implementations, the method also includes deriving a value representing an evaluation of a state of the subject based on the data.

In some implementations, the state of the subject includes a health-related state.

In some implementations, the state of the subject is associated with one or more of sleep quality, sleep duration, sleep latency, and sleep staging.

In some implementations, the value is provided to the subject or to another party.

In some implementations, the value is derived based on data related to motion of the subject.

In some implementations, the data is acquired by a device that is worn by the subject and that displays the value.

In some implementations, the device derives the value.

In some implementations, the device provides the data to a remote device that derives the value.

In some implementations, the method also includes processing data that represents information about an amount of ultraviolet light that the subject has been exposed to.

In some implementations, the method also includes correlating a characteristic of the subject's sleep to the amount of ultraviolet light that the subject has been exposed to.

In some implementations, the method also includes correlating a quality of the subject's sleep to the amount of ultraviolet light that the subject has been exposed to.

In some implementations, the method also includes correlating a duration of the subject's sleep to the amount of ultraviolet light that the subject has been exposed to.

In some implementations, the processor is also configured to identify a period of time as a non-sleep period based on gross motion data of the subject measured by the motion sensor.

In some implementations, identifying the period of time as a non-sleep period includes determining that the gross motion data during the period of time is above a threshold.

In some implementations, identifying the period of time as a non-sleep period includes determining that the gross motion data during the period of time is substantially irregular.

In some implementations, the processor is also configured to identify a period of time as a sleep period based on gross motion data of the subject measured by the motion sensor.

In some implementations, identifying the period of time as a sleep period includes determining that the gross motion data during the period of time is below a threshold.

In some implementations, identifying the period of time as a sleep period includes determining that the gross motion data during the period of time is substantially flat.

In some implementations, the processor is also configured to determine a start and an end of the sleep period.

In some implementations, determining the start of the sleep period includes identifying a time when the gross motion data falls below a threshold, and determining the end of the sleep period includes identifying a time when the gross motion data rises above a threshold.

In some implementations, the processor is also configured to calculate a property of the sleep of the subject based on the data.

In some implementations, the characteristic of the subject's sleep is determined based on the property, and the characteristic of the subject's sleep includes sleep apnea.

In some implementations, the processor is also configured to determine that the subject is experiencing sleep apnea. Determining that the subject is experiencing sleep apnea includes identifying a simple signal in a heart rate signal of the subject that is acquired during a sleep period of the subject.

In some implementations, determining that the subject is experiencing sleep apnea includes identifying recurring simple signals in the heart rate signal of the subject.

In some implementations, the simple signals recur at least every two minutes during the sleep period of the subject.

In some implementations, the characteristic includes a quality of the sleep, including one or more of latency to sleep, number of disturbances, and number of tosses and turns.

In another aspect, a method includes processing data in a first dataset that represents time-varying information about at least one pulse pressure wave propagating through blood in a subject acquired at a location of the subject. The data in the first and second datasets is acquired while the subject is in a situation that requires at least a predetermined amount of alertness of the subject.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The data is acquired while the subject is in a situation that requires at least a predetermined amount of alertness of the subject.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a processor configured to receive data from one or both of the light-emitting element and the optical sensor. The processor is also configured to process the data to derive a measure of alertness of the subject.

Implementations can include one or more of the following features.

In some implementations, the method also includes processing data in a second dataset that represents time-varying information about motion of the subject acquired at the location of the subject In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the situation includes one in which a likelihood of harm to one or more human lives is increased if the alertness of the subject is below the predetermined amount.

In some implementations, the situation is one in which a likelihood of damage to one or more properties is increased if the alertness of the subject is below the predetermined amount.

In some implementations, the situation is one in which a likelihood of economic damage is increased if the alertness of the subject is below the predetermined amount.

In some implementations, the situation is one or more of air traffic control, intelligence analysis, vehicle driving, machinery driving, security guarding, baggage screening, and aircraft piloting.

In some implementations, the method also includes using the processed data to derive a measure of alertness of the subject.

In some implementations, the measure of alertness of the subject is based on one or more of a heart rate, a respiratory rate, a blood pressure, and an activity level of the subject.

In some implementations, the method also includes activating an alarm on a device worn by the subject if the measure of alertness of the subject falls below a threshold.

In some implementations, the device worn by the subject acquires the data.

In some implementations, the device worn by the subject processes the data.

In some implementations, the method also includes causing a speed of a vehicle being operated by the subject to be decreased if the measure of alertness of the subject falls below a threshold.

In some implementations, the method also includes causing an alarm in a vehicle being operated by the subject to be activated if the measure of alertness of the subject falls below a threshold.

In some implementations, the method also includes causing a device being operated by the subject to be turned off if the measure of alertness of the subject falls below a threshold.

In some implementations, the method also includes causing an operation switch of a vehicle being operated by the subject to be turned off if the measure of alertness of the subject falls below a threshold.

In some implementations, the method also includes assigning a task to the subject based on the measure of alertness.

In some implementations, the subject is put into an athletic contest if the measure of alertness of the subject is above a threshold.

In some implementations, the subject is assigned a particular combat task if the measure of alertness of the subject is above a threshold.

In some implementations, the biofeedback device also includes a motion sensor configured to provide data that represents time-varying information about motion of the subject acquired by the motion sensor at the location of the subject. The processor is also configured to receive and process the data from the motion sensor.

In some implementations, the biofeedback device also includes a transceiver configured to provide one or both of the processed data and the measure of alertness.

In some implementations, the transceiver is also configured to cause a speed of a vehicle being operated by the subject to be decreased if the measure of alertness of the subject falls below a threshold.

In some implementations, the transceiver is also configured to cause an alarm in a vehicle being operated by the subject to be activated if the measure of alertness of the subject falls below a threshold.

In some implementations, the transceiver is also configured to cause a device being operated by the subject to be turned off if the measure of alertness of the subject falls below a threshold.

In some implementations, the transceiver is also configured to cause an operation switch of a vehicle being operated by the subject to be turned off if the measure of alertness of the subject falls below a threshold.

In some implementations, the processor is also configured to assign a task to the subject based on the measure of alertness.

In some implementations, the subject is put into an athletic contest if the measure of alertness of the subject is above a threshold.

In some implementations, the subject is assigned a particular combat task if the measure of alertness of the subject is above a threshold.

In some implementations, operations also include processing data in a second dataset that represents time-varying information about motion of the subject acquired at the location of the subject.

In another aspect, a method includes processing data in a first dataset that represents time-varying information about at least one pulse pressure wave propagating through blood in a subject acquired at a location of the subject. The method also includes predicting a medical event of the subject based on the processed data.

In another aspect, one or more machine-readable storage devices stores instructions that are executable by one or more processing devices to perform operations including processing data in a first dataset that represents time-varying information about at least one pulse pressure wave propagating through blood in a subject acquired at a location of the subject. The operations also include predicting a medical event of the subject based on the processed data.

In another aspect, a biofeedback device configured to be worn by a subject includes a light source configured to emit light toward the skin of the subject. The device also includes an optical sensor configured to receive the emitted light after the emitted light reflects off of the skin of the subject. The optical sensor is also configured to provide data that corresponds to a characteristic of the received light, the data representing time-varying information about at least one pulse pressure wave propagating through blood in the subject acquired by the optical sensor at a location of the subject. The device also includes a processor configured to receive data from one or both of the light-emitting element and the optical sensor. The processor is also configured to predict a medical event of the subject based on the data.

Implementations can include one or more of the following features.

In some implementations, the method also includes processing data in a second dataset that represents time-varying information about motion of the subject acquired at the location of the subject.

In some implementations, the information about at least one pulse pressure wave propagating through blood in the subject includes photoplethysmographic (PPG) data and the information about motion of the subject includes one or both of motioncardiogram (MoCG) data and gross motion data.

In some implementations, the data is acquired continuously.

In some implementations, the data is acquired at a frequency of at least 16 Hz.

In some implementations, the data is acquired at a frequency of between 75 Hz and 85 Hz.

In some implementations, the data is acquired at a single location of the subject.

In some implementations, the data is acquired by a device worn by the subject.

In some implementations, the device is mobile and does not reduce a mobility of the subject.

In some implementations, the device processes the data.

In some implementations, the single location is an arm of the subject.

In some implementations, the single location is a wrist of the subject.

In some implementations, the method also includes alerting a caregiver when a medical event of the subject is predicted.

In some implementations, processing the data includes determining one or more of heart rate, heart rate variability, blood pressure, blood pressure variability, body temperature, skin temperature, vocal tonality, electrical skin impedance, respiratory rate, blood oxygen level, stroke volume, cardiac output, MoCG morphology, and PPG morphology of the subject.

In some implementations, predicting the medical event of the subject includes determining whether a heart rate of the subject satisfies a threshold.

In some implementations, the medical event is tachycardia.

In some implementations, determining the heart rate of the subject includes calculating a distance between two consecutive reference points in the first dataset, the distance representing a time that has elapsed between two consecutive heartbeats of the subject.

In some implementations, the reference points are local maxima or local minima.

In some implementations, the reference points are peaks or valleys.

In some implementations, predicting the medical event of the subject includes determining whether a heart rate variability of the subject satisfies a threshold.

In some implementations, the threshold is based on whether the subject experiences arrhythmia.

In some implementations, determining the heart rate variability of the subject includes calculating distances between multiple pairs of consecutive reference points in the first dataset, each distance representing a time that has elapsed between two consecutive heartbeats of the subject.

In some implementations, the reference points are local maxima or local minima.

In some implementations, the reference points are peaks or valleys.

In some implementations, predicting the medical event of the subject includes determining whether a blood pressure of the subject satisfies a threshold.

In some implementations, the medical event is hypertension.

In some implementations, predicting the medical event of the subject includes determining a rate of change of a blood pressure of the subject.

In some implementations, the medical event is a stroke, and a stroke is predicted if the rate of change of the blood pressure of the subject is positive and above a threshold.

In some implementations, the medical event is abnormal heart function, and abnormal heart function is predicted if the rate of change of the blood pressure of the subject is negative and below a threshold.

In some implementations, the method also includes identifying a first point in the first dataset, the first point representing an arrival time of the pulse pressure wave at a first body part of the subject. The method also includes identifying a second point in the second dataset, the second point representing an earlier time at which the pulse pressure wave traverses a second body part of the subject. The method also includes computing a pulse transit time (PTT) as a difference between the first and second points, the PTT representing a time taken by the pulse pressure wave to travel from the second body part to the first body part of the subject.

In some implementations, the blood pressure of the subject is determined based on the PTT.

In some implementations, the first body part is the location of the subject at which the data in the first data set is acquired, and the second body part is the heart of the subject.

In some implementations, the device also includes a motion sensor configured to provide data that represents time-varying information about motion of the subject acquired by the motion sensor at the location of the subject. The processor is also configured to receive data from the motion sensor.

In some implementations, the device also includes a transceiver configured to alert a caregiver when a medical event of the subject is predicted.

In some implementations, the operations also include processing data in a second dataset that represents time-varying information about motion of the subject acquired at the location of the subject.

Aspects can include one or more of the following advantages.

Particular implementations may realize one, or more of the following advantages. Blood pressure and/or other biometric parameters may be measured based on continuously acquired data, without the need for cuffs, pressure points or electrodes. "Continuously" acquiring data, as used herein, means acquiring data at a sufficient frequency (e.g., a sufficient number of times per second) to allow for the derivation of the parameters described herein from that data. The data can, for example, be collected at a frequency ranging from 16 Hz to 256 Hz. In certain implementations, the data is acquired at a frequency of between 75 Hz and 85 Hz. Vital signs can be measured at one location, using a comfortable and unobtrusive device. By providing an ability to capture continuous measurements 24 hour a day, a new paradigm in monitoring health can be enabled, thereby allowing for recording transient medical events that may otherwise go undetected. The disclosed technology may be integrated with third party devices (for example, mobile devices) thereby allowing for using external sensors such as motion detectors and light sensors disposed in the third party devices.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 31 shows an example of the technology being used with a proximity system.

FIGS. 39A-39C show examples of user interfaces of an application that makes data collected by the device of FIGS. 1B and 1C available to a user.

DETAILED DESCRIPTION

This document describes technology for determining pulse transit time (PTT) of blood based on motion data such as motioncardiogram (MoCG) data (which is related to, and also referred to in this document as ballistocardiogram (BCG) data) and optical data such as photoplethysmographic (PPG) data. When determined using motion data of the body, PTT can also be referred to as motion pulse transit time (MPTT). In this document, the terms PTT and MPTT may be used interchangeably. This document also describes technology for performing various biometric measurements (e.g., blood pressure, respiratory rate, blood oxygen level, stroke volume, cardiac output, arterial stiffness, and temperature) based on the MoCG data and the PPG data. The MoCG is an example of a motion of the subject. For example, MoCG is a pulsatile motion signal of the body measurable, for example, by a motion sensor such as an accelerometer or a gyroscope. The pulsatile motion signal results from a mechanical motion of portions of the body that occurs in response to mechanical motion of the heart. For example, the pulsatile motion signal can result from mechanical motion of portions of the body that occurs in response to blood being pumped during a heartbeat. This motion is a mechanical reaction of the body to the internal pumping of blood and is externally measurable. The MoCG signal therefore corresponds to, but is delayed from, the heartbeat. The MoCG signal recorded at a given portion of the body therefore represents the motion of the blood due to a heartbeat, but is delayed from, the heart's electrical activation (e.g. when the ventricles are electrically depolarized).

PPG data is data optically obtained via a plethysmogram, a volumetric measurement of the vasculature. PPG data can be obtained using an optical device which illuminates the skin and measures changes in light absorption. With each cardiac cycle the heart pumps blood resulting in a pressure pulse wave within the vasculature. This causes time-varying changes in the volume of the vasculature. The changes can be detected, for example, by illuminating the skin with light from a light-emitting diode (LED) and then measuring the amount of light either transmitted or reflected to a detector such as a photodiode. Each cardiac cycle is therefore represented as a pattern of crests and troughs. The shape of the PPG waveform differs from subject to subject, and varies with the location and manner in which the waveform is recorded.

Figure 1A:
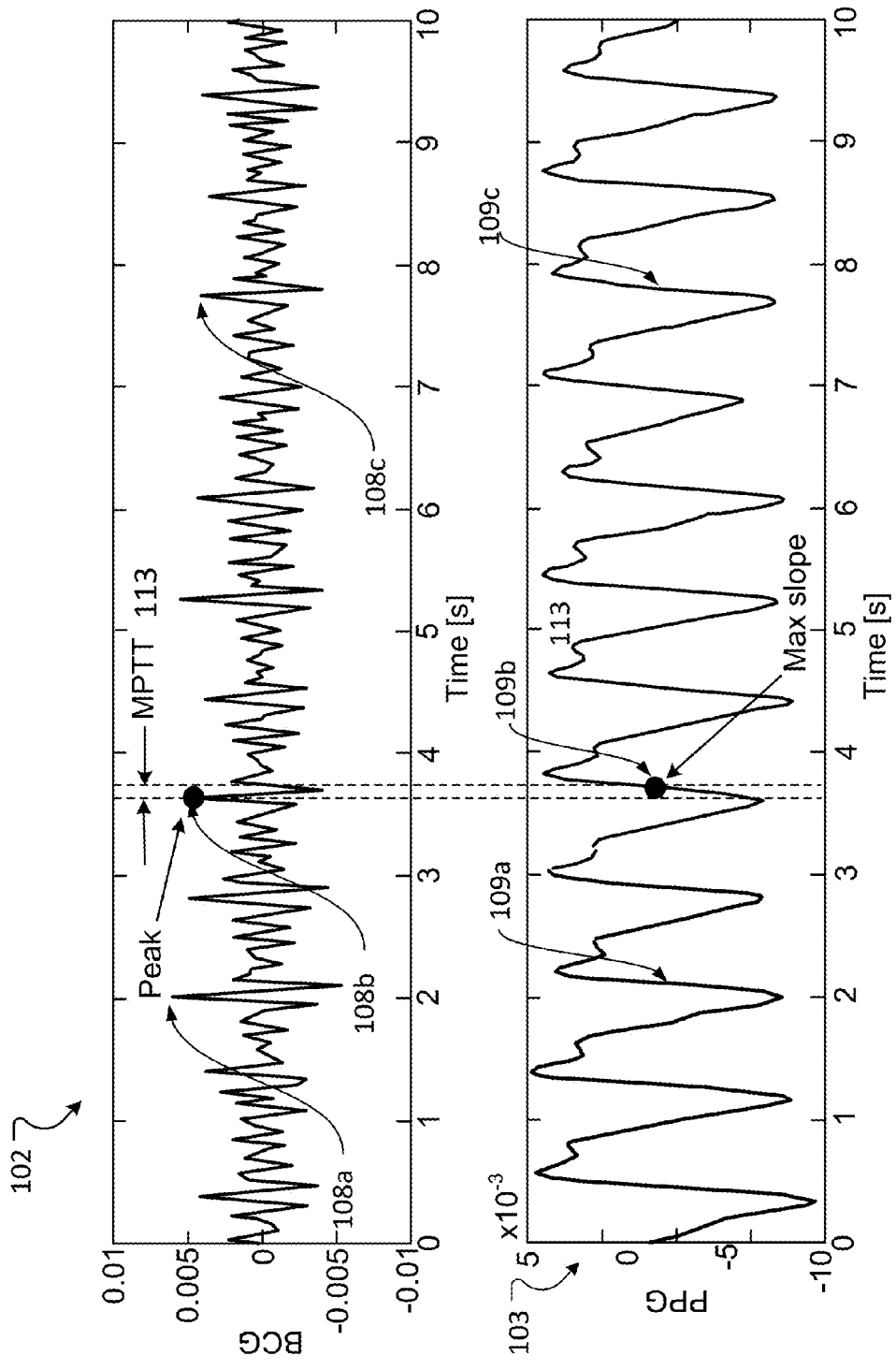
FIG. 1A illustrates pulse transit time (PTT) calculation using an example BCGB plot, and a photoplethysmogram (PPG) plot.

FIG. 1A illustrates pulse transit time (PTT) calculation using an example BCG plot 102, and a photoplethysmogram (PPG) plot 103. BCG plot 102 can be analyzed to determine points at which a pulse (or pressure wave) originates at a first location on the body. The BCG however, may be measured at a second location on the body. For example, the points (e.g., local maxima) 108a, 108b and 108c in the BCG plot 102 may represent time points at which corresponding pulses originate at or near the chest. These points are often referred to in this document as pulse origination points.

The time of arrival of the pulse at a second location (e.g., the wrist) can be determined from PPG data obtained at the second location. For example, the PPG data can be measured at the wrist using one or more optical sensors. Light from the optical sensors (i.e., the light sources such as LEDs of the optical sensors) is directed toward the skin of the subject, and the reflected light (which is modulated by blood volume changes underneath the skin) is measured using one or more photo-detectors (e.g., photodiodes). The output of the photo-detector may be amplified by an amplifier before being converted to a digital signal (for example, by an analog to digital converter (ADC)) that represents the PPG.

The plot 103 of FIG. 1A represents PPG data that can be used to determine the arrival time of the pulses at the wrist. For example, the maximum slope points 109a, 109b, and 109c (109 in general) represent the arrival times of the pulses that originated at the chest at time points represented by 108a, 108b, and 108c, respectively. These points may in general be referred to in this document as pulse arrival points 109. The plot 103 is synchronized with the BCG plot 102 such that the PTT (or MPTT) 113 between the chest and the wrist can be determined as a time difference between the originating point at the chest and the corresponding arrival point at the wrist. In the example shown in FIG. 1A, the time difference between 108b and 109b represents the PTT 113. Similarly, the time difference between 108a and 109a, or the time difference between 108c and 109c can be used in determining the PTT 113.

The technology described in this document allows for determination of PTT from MoCG (or BCG) and PPG data measured at substantially the same location on a human body (e.g., the wrist). This includes identifying, from the PPG data, a time point (e.g., the time points 109) at which a pulse wave arrives at the location, identifying, from the BCG data, a time point (e.g., the time points 108) at which the pulse originated at a different location on the body (e.g., the heart) from the MoCG data, and determining the PTT 113 as a difference between the two identified time points.

Figure 1B:
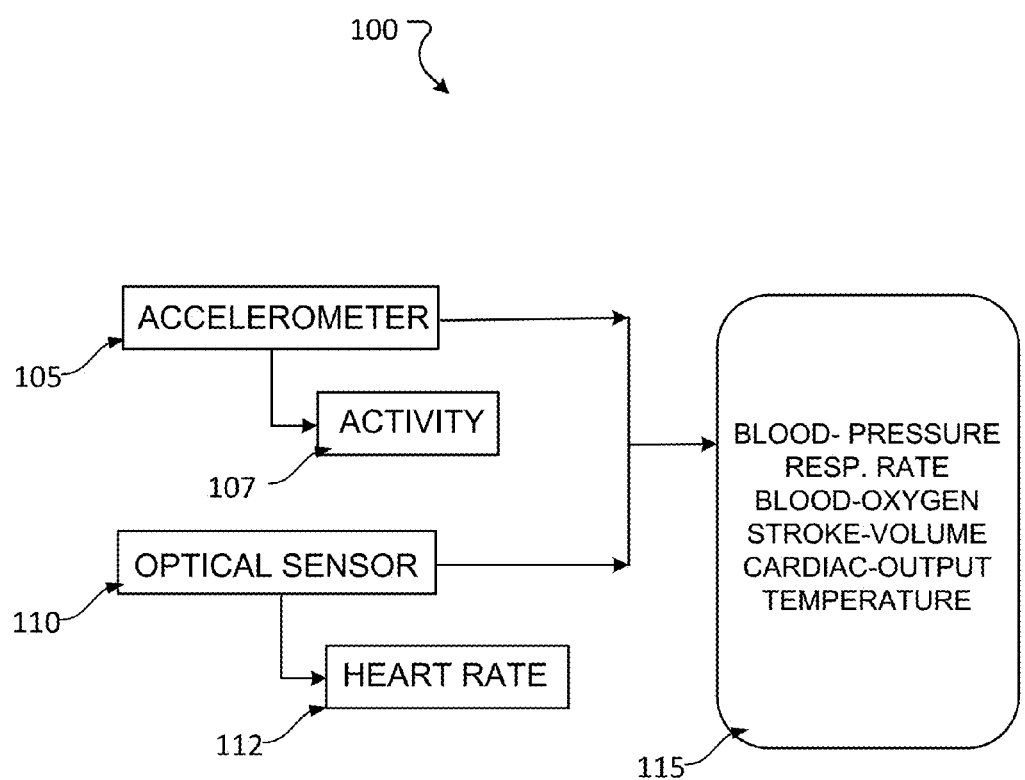
FIGS. 1B and 1C are example block diagrams of a device that performs biometric measurements based on MoCG and PPG data.
Figure 32A:
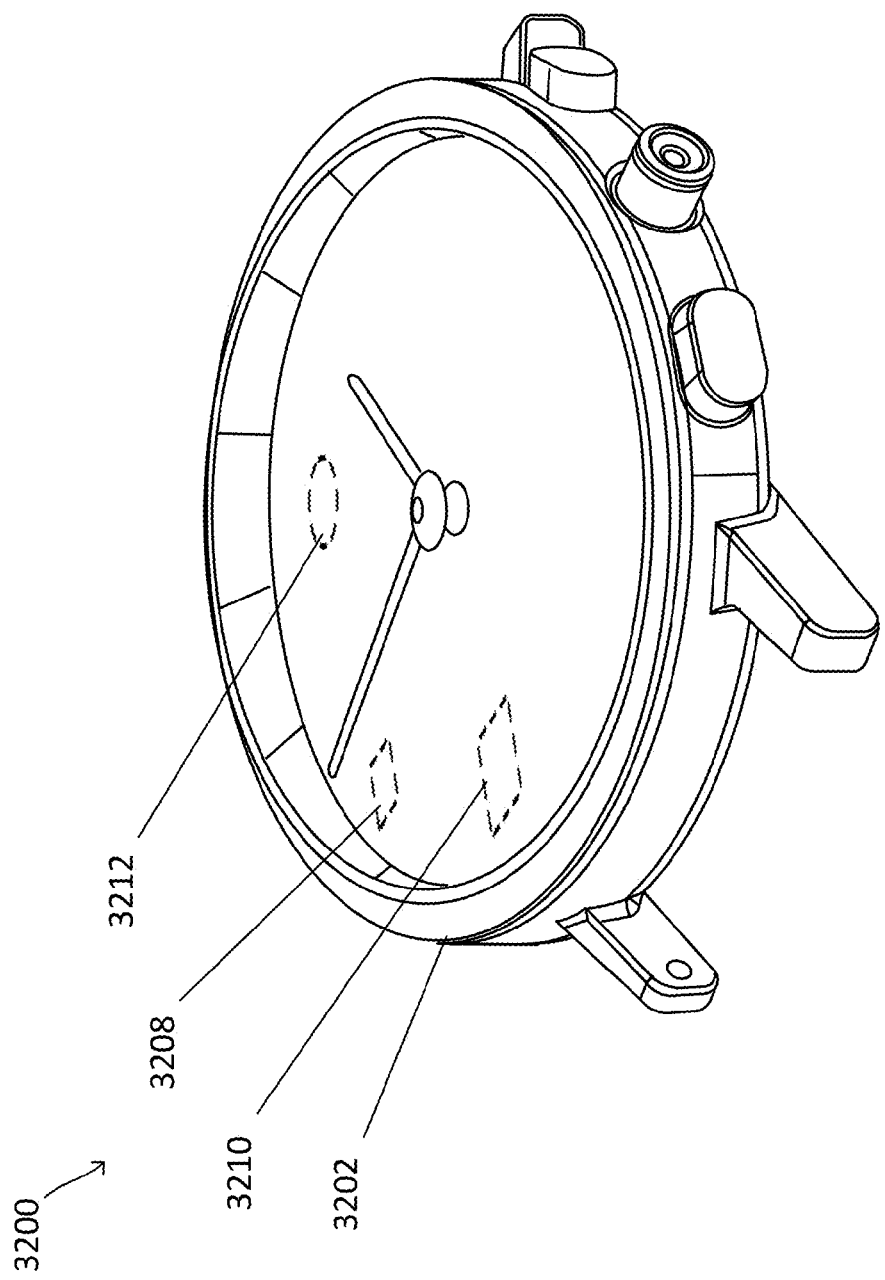
FIGS. 32A and 32B show an example implementation of the device of FIGS. 1B and 1C in the form of a wearable watch.
Figure 32B:
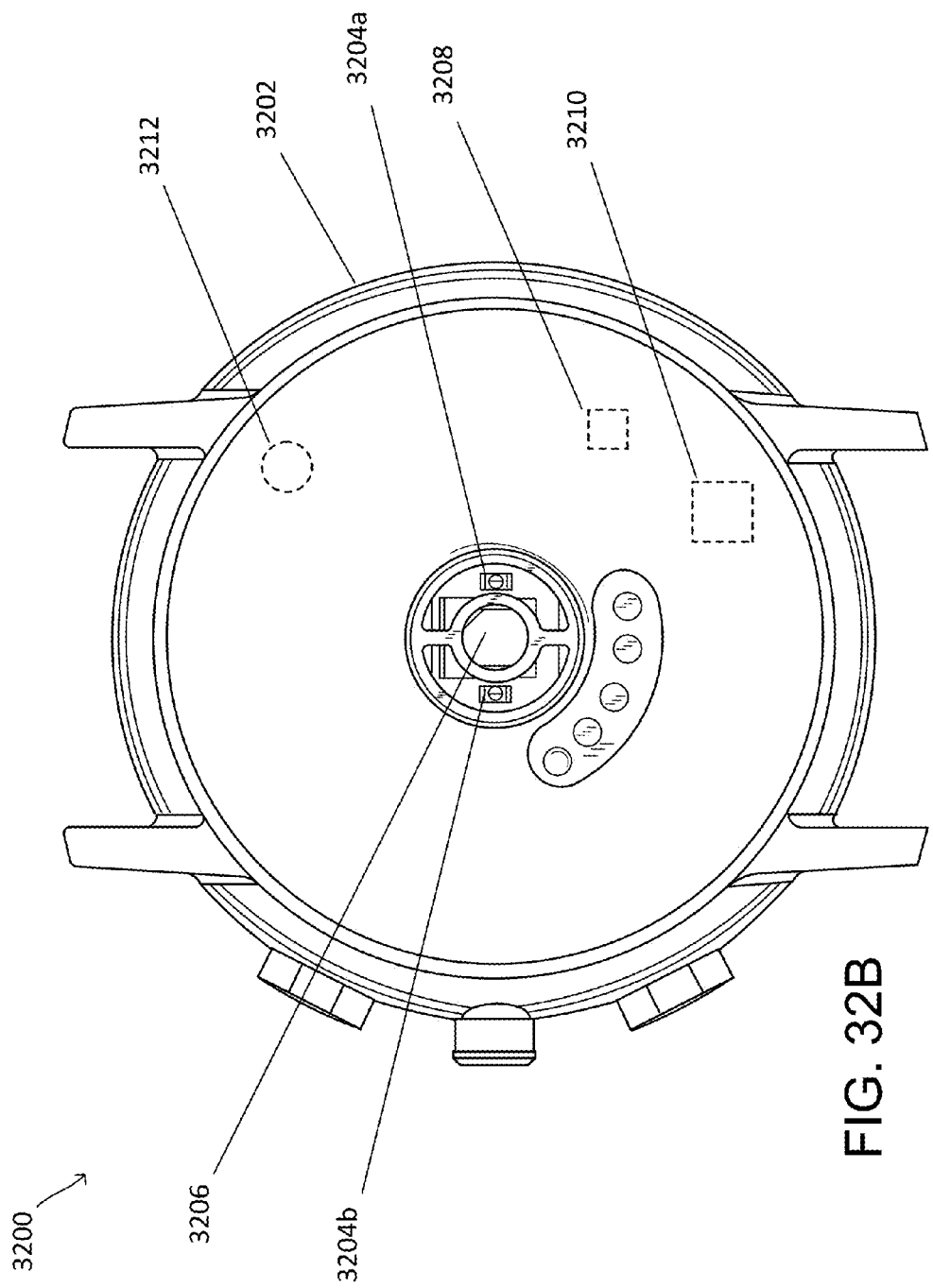

FIG. 1B is a block diagram of an example of a device 100 that performs biometric measurements based on MoCG and PPG data. The biometric measurements can be used for monitoring health related parameters, as well as in diagnosing conditions and predicting an onset of such conditions. In some implementations, the device 100 can be a wearable device that a subject can wear on the body. For example, the device 100 can be disposed in a wearable watch, bracelet, anklet, armband, chest-patch, or belt. An example implementation of the device in the form of a wearable watch 3200 is shown in FIGS. 32A and 32B. The watch 3200 includes a case 3202 that is configured to hold the internal components of the watch, including light sources 3204a, 3204b, an optical sensor 3206, a motion sensor 3208, a processor 3210, and an ultraviolet light sensor 3212.

In some implementations, the device may also be disposed as a part of a garment worn by the subject. The device 100 may also be disposed in a rug or mat (e.g., a bathroom mat or a shower mat). The device 100 may also be disposed in a separate device carried or worn by the subject. For example, the device 100 can be disposed internally or externally in a watch or mobile device used by the subject. In some implementations, the device 100 can include a transceiver that is configured to communicate wirelessly with another device to perform a biometric monitoring process. For example, data collected and/or computed by the device 100 may be transmitted to an application executing on a mobile device for additional analysis or storage. On the other hand, alerts and messages may be transmitted from a server or mobile device for display on the device 100. Devices similar to the device 100 are described in U.S. patent application Ser. Nos. 13/166,388 and 13/803,165, and 61/660,987, the contents of which are incorporated by reference herein. Various combinations of the operations described in this document may also be performed by a general purpose computing device that executes appropriate instructions encoded on a non-transitory computer readable storage device such as an optical disk, a hard disk, or a memory device.

The device 100 can be configured to make MoCG and PPG measurements either directly (such as when implemented as a part of an armband, wristband, chest patch, undergarment) or indirectly (such as when implemented as part of a mobile device) from a portion of the body proximate to the location of the device. The MoCG data can be measured using one or more motion sensors 105 such as an accelerometer or a gyroscope. In some implementations, the motion sensors 105 include multiple accelerometers (e.g., one for each of the x, y, and z axes) and/or multiple gyroscopes (e.g., one each for measuring tilt, rotation, and yaw). Even though FIG. 1B shows only motion sensors and optical sensors, other types of sensors such as electric impedance sensors (including electrical skin impedance sensors, such as Galvanic skin resistance sensors), hydration level sensors, skin reflection index sensors, and strain sensors can also be used in performing one or more of the measurements described in this document. In some implementations, one or more of the sensors may be located in an external device such as a mobile device. For example, motion sensors and a camera disposed in a mobile device may be used in place of the motion sensors 105 and optical sensor 110, respectively. In some implementations, the device 100 can include one or more sensors to measure or detect ambient conditions. Such sensors can include, for example, a microphone (e.g., to measure environmental noise), an altimeter, a humidity sensor, a GPS device (for determining geographical location), and an ultraviolet light sensor (e.g. to detect level of sun exposure).

In some implementations, the device 100 can be configured to warn the user (for example, by displaying a message) if a measured, derived, or inferred health parameter is outside an acceptable range for the parameter. Examples of such health parameters can include (without being limited to the following) measured parameters such as heart rate, respiratory rate, or arrhythmia, derived parameters such as blood pressure, stroke volume, or arterial stiffness, and inferred parameters such as mood, stress level, or sleep deprivation. In one example, the level of sun exposure (as measured by the ultraviolet light sensor) can be correlated to the mood or stress level of the user, and related suggestions and recommendations can be provided accordingly. For example, if sun exposure above a certain threshold level is known to decrease stress for a particular user, the user may be asked to increase sun exposure during a period when a stress level detected by the device 100 is high.

In some implementations, environmental sounds captured by the microphone can be used to contextualize or interpret vital signs data captured using the device 100. For example, a tonality (e.g., amplitude and/or frequency) of a user's voice can be analyzed to determine if the user is in a confrontational situation (e.g., at work or at home) that can be attributed to an unacceptable level of a particular health parameter (e.g., stress). In another example, environmental noise can be detected during a user's commute to determine, for example, if, and to what extent driving (or rush hour subway) affects the user's health parameters. In yet another example, if a user is detected to be having a disturbed sleep pattern, the data captured by the microphone can be used to determine and/or confirm if that is attributable to environmental noise (e.g., snoring, or an alarm clock going off). In another example, if an unacceptable condition (e.g., a user's increased stress level) coincides with construction activity (determined, for example, via pile driver sounds captured by the microphone), a determination may be made that the unacceptable condition is likely due to the sounds coming from the construction site.

Figure 1C:
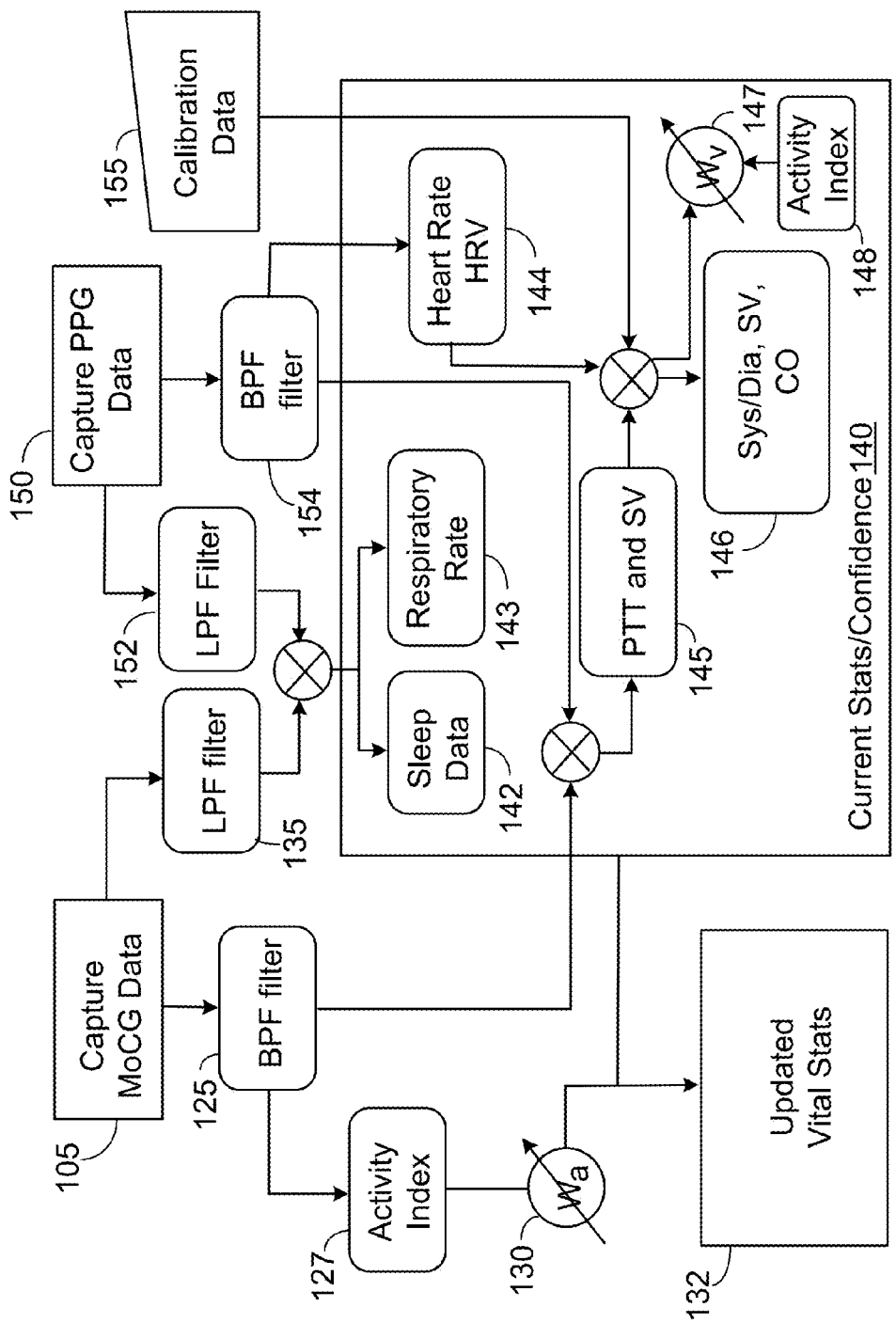
Figure 1D:
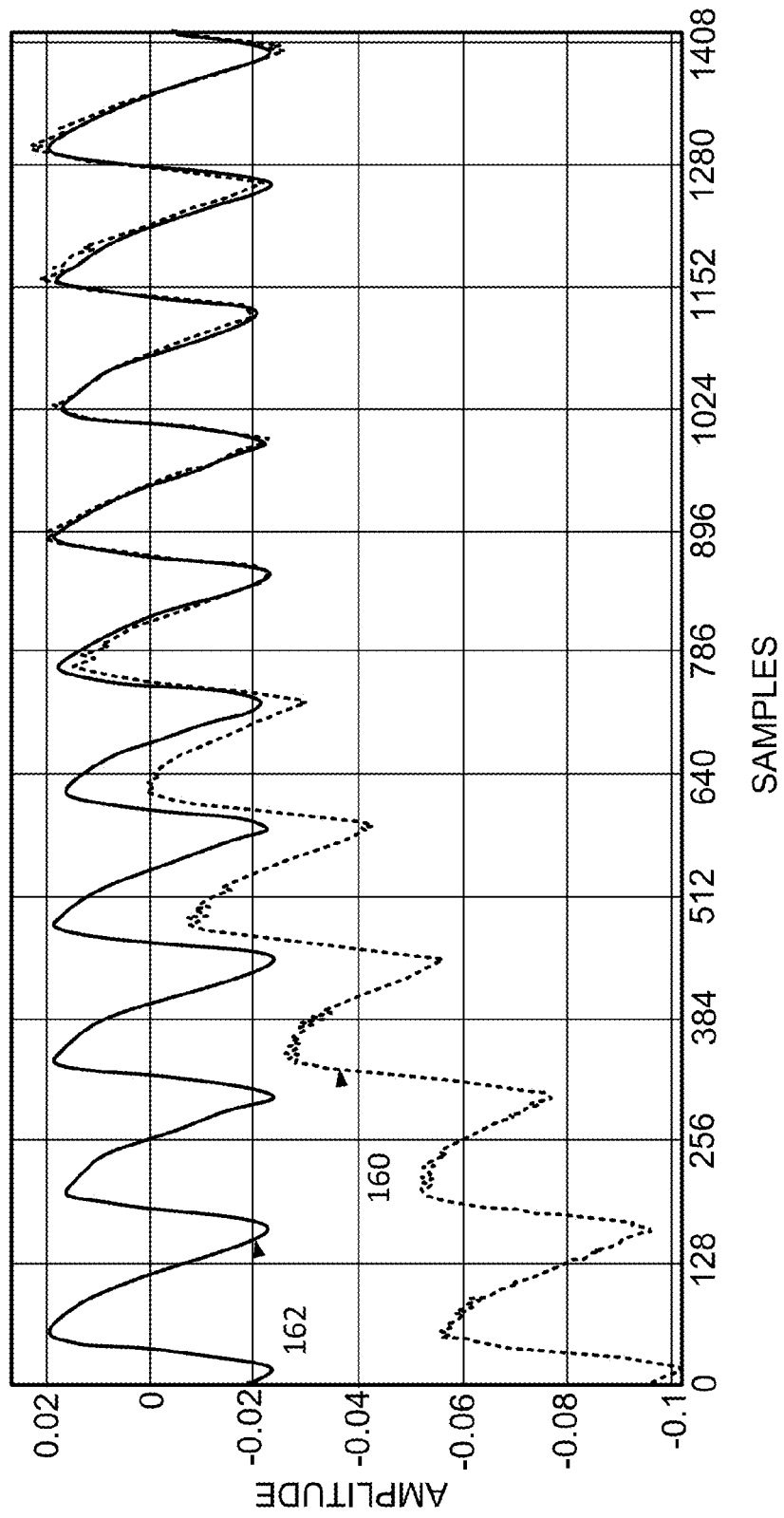
FIGS. 1D-1F are plots generated based on data collected using sensors of the device of FIGS. 1B and 1C.
Figure 1E:
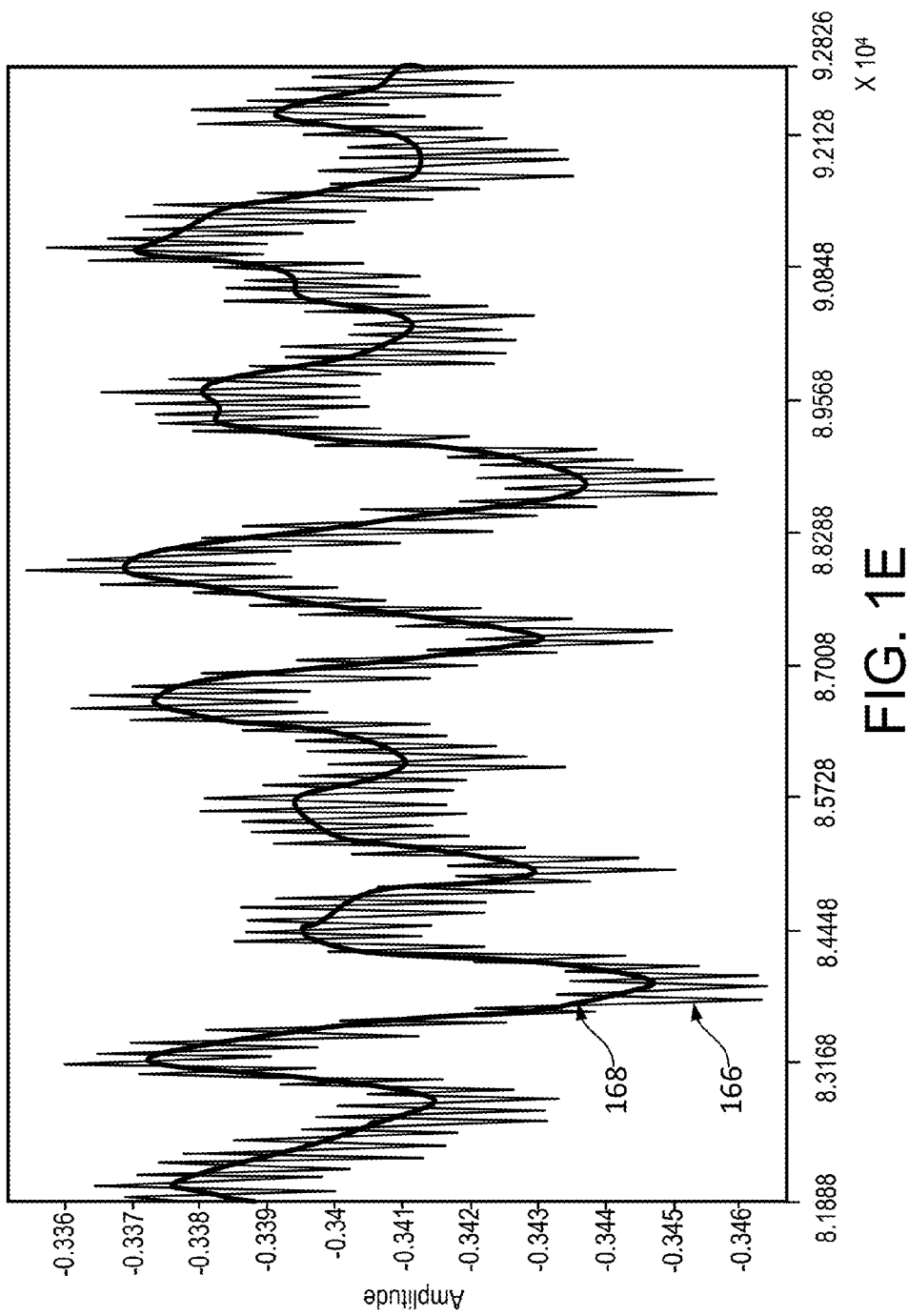
Figure 1F:
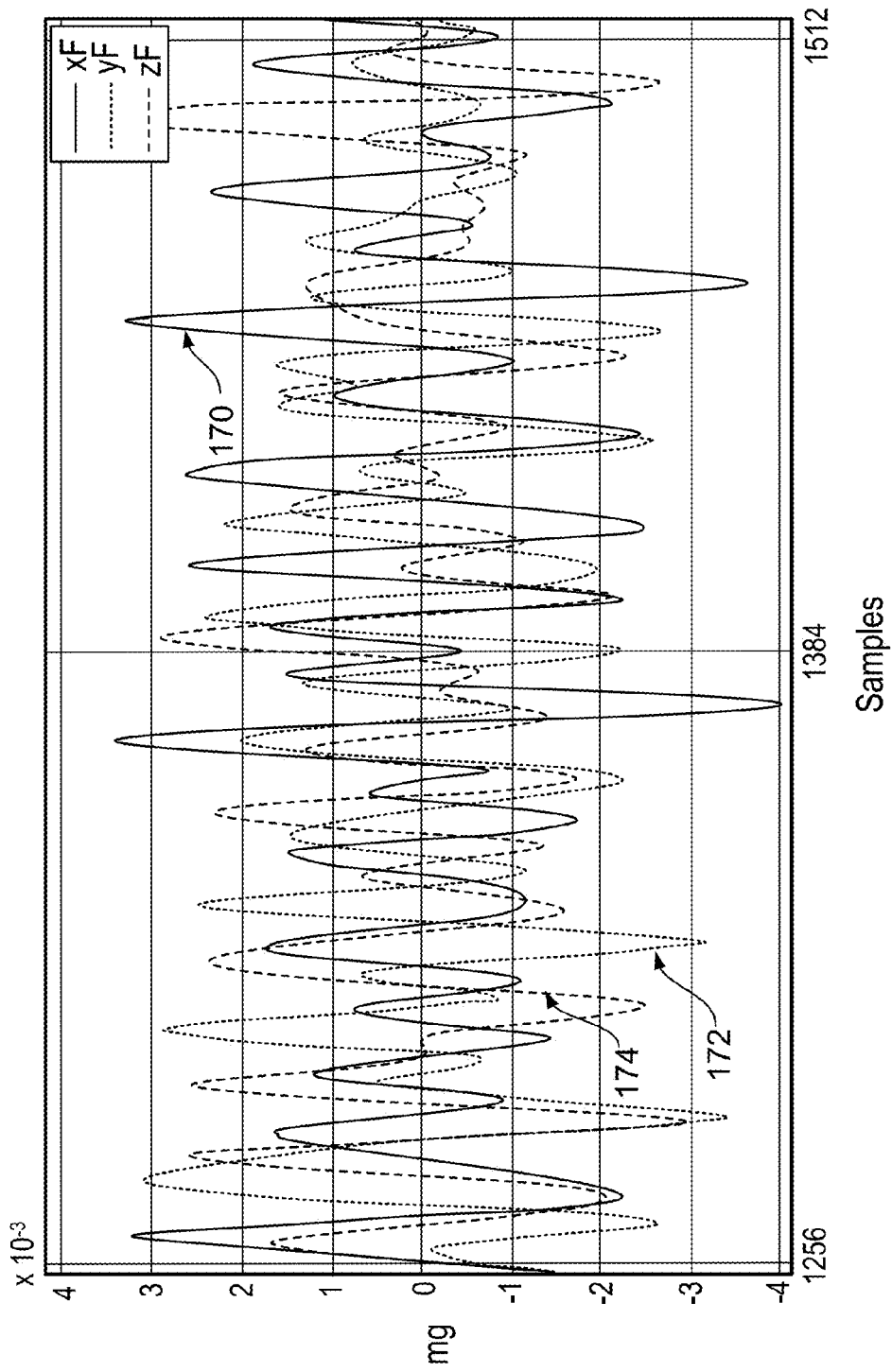

The data captured using the motion sensors 105 includes both MoCG data and motion data associated with an activity of the subject. The MoCG data can be filtered out from the combination using, for example, one or more band pass filters (BPF) 125 shown in FIG. 1C. In some implementations, a pass band of the BPF 125 can be designed to filter out constant components (e.g., acceleration due to gravity) and high frequency noise components. For example, in some cases, a pass band of 3-12 Hz may be used for the band pass filter 125. In other cases multiple band pass filters may be used concurrently. For example, a filter with a 3-12 Hz passband and another filter with a 10-30 Hz passband can be used simultaneously to measure different parameters measurable in the two different bands. In some implementations, the band pass filtered accelerometers can be combined to obtain an activity index 127, which in turn is used in calculating appropriate weights 130 for obtaining updated biometric measurements 132. For example, if the subject is sitting still, the activity index 127 can be less than a threshold value (e.g., 5) indicating, for example, that the band pass filtered accelerometer outputs can be used directly in determining the biometric measurements. In another example, if the subject is running, the activity index 127 can be higher (e.g., between 5 and 15), indicating that the band pass filtered accelerometer data may need to be adjusted (e.g., by applying a threshold) before being used in determining the biometric measurements. In some implementations, if the activity index is higher than an upper threshold value (e.g., 15), the band pass filtered accelerometer data may be discarded as being unreliable. In some implementations, weights 130 may be adjusted to reflect if and how the band pass filtered data from the accelerometer 105 is used. Examples of band pass filtered accelerometer data are illustrated in FIG. 1F, where plots 170, 172, and 174 represent outputs of accelerometers in the x, y, and z axes, respectively.

Figure 1G:
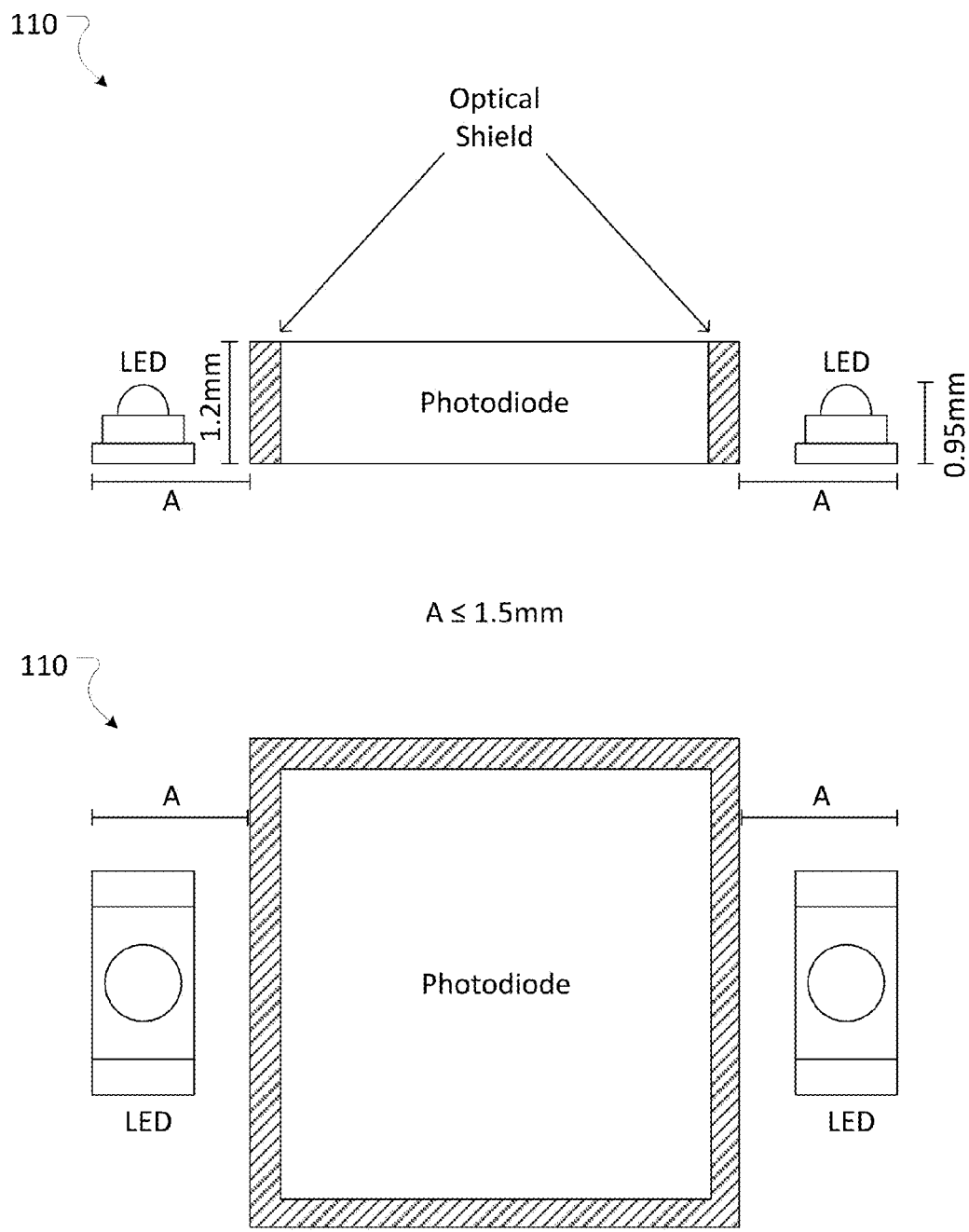
FIG. 1G illustrates side and top views of an example configuration of optical sensors that can be used in the device of FIGS. 1B and 1C.

In some implementations, the PPG data can be measured using one or more optical sensors 110. In some implementations, the optical sensors 110 can include one or more light emitting diodes (LEDs) whose output can be controlled, for example, by a microcontroller. Example configurations of the optical sensors 110 are depicted in FIG. 1G. In some implementations, the optical sensors include a 7.5 mm² photodiode with two green LEDs placed within 1.5 mm of either side. The photodiode has an opaque optical shield surrounding the sides. The LEDs can have a peak wavelength of 525 nm and a viewing angle of 60 degrees.

In operation, light from the optical sensors 110 (i.e., from the light sources such as LEDs of the optical sensors) is directed toward the skin of the subject, and the reflected light is modulated by blood flow underneath the skin. The optical sensors 110 also include one or more photo-detectors (e.g., photodiodes) that receive the reflected light and provide a resulting signal to the microcontroller. The resulting signal may be amplified by an amplifier before being converted to a digital signal (for example, by an analog to digital converter (ADC)) that is provided to the microcontroller. The PPG signal is synchronized with the heartbeat and can therefore be used to determine the heart rate (HR) 112 of a wearer of the device. This is shown in additional detail in FIG. 1C. In some implementations, the heart rate signal can be within a particular range of the spectrum (e.g., 0 to one half of the sampling frequency) of the PPG signal 150, and can be isolated using, for example, a band pass filter (BPF) 154. An example of this is shown in FIG. 1D, where the plot 160 represents raw PPG data, and the plot 162 represents the output of the BPF 154. The pass band of the filter used for the example depicted in FIG. 1C is 0.4-4 Hz. As seen from FIG. 1C, the low frequency portion of the raw data, as well as the high frequency variations are filtered out in the output plot 162.

In some implementations, it could be desirable to sample the optical PPG sensor at a low frequency to achieve power savings. However, a low sampling frequency can cause interference between the optical sensors and artificial light sources, which usually oscillate at the frequency of 60 Hz and 120 Hz in North America, and 50 Hz and 100 Hz worldwide. If the sampling rate is lower than the Nyquist rate corresponding to the maximum frequency (e.g., 120 Hz*2=240 Hz) then aliasing would occur. For example, if the PPG sensor is sampled at 121 Hz, then a 120 Hz interfering source will alias as 1 Hz, which is within the frequency of heart rate and could cause confusion. In some implementations, a frequency between 75-85 Hz is chosen such that reasonable power saving is achieved, and the optical interferers are aliased into non-biological optical signal frequency range (>10 Hz). For example, if 80 Hz is chosen, then the aliased interferers would be at frequencies such as 20 Hz, 30 Hz, and/or 40 Hz. An appropriate low pass filter (e.g., a filter with cut-off frequency of 10 Hz) could then be used to eliminate the interferers while preserving the PPG signal. If a finer time resolution is desired (e.g., corresponding to 256 Hz), the filtered PPG signal can be interpolated accordingly in time domain without signal loss.

In some implementations, the output of the BPF 154 can be used to determine a heart rate 144 of the subject, and can also be combined with the output of the BPF 125 to determine other biometric parameters such as pulse transit time (MPTT) and stroke volume (SV) 145, as well as other parameters 146, including, for example, systolic and diastolic blood pressure, stroke volume (SV), and cardiac output (CO).

In some implementations, calibration data 155 is used in computing one or more of the parameters 146. For example, the calibration data 155 can include user-specific calibration information (e.g., constants used in equations) that may be used in computing one or more of the parameters 146. In some implementations, the calibration data 155 can be computed based on user-provided data. For example, a user may be asked to provide biographical data such as age, height, and weight for use in computing the calibration data. In some implementations, the user can be asked to provide his/her last-known blood-pressure data to determine one or more constants or parameters included in the calibration data 155. In some cases, a medical professional may measure a user's blood pressure during set up of the device 100. In some implementations, calibration data 155 can be calculated based on a user action. For example, the user may be asked to hold the device 100 at or near chest level to equalize hydrostatic pressure effects and sense chest vibrations that are used in computing a calibration point. This way, a delay between a chest vibration and the time of arrival of a pulse wave at the wrist (if the device 100 is worn on the wrist) can be used to calibrate for blood pressure for a scenario where there is no height difference between the heart and the measuring point. In some implementations, the calibration data 155 can include information related to skin tone calibration where LED intensity and amplifier gain are adjusted until an optimal DC level is reached. If no user-specific calibration data is available, standard calibration values (for example parameters to get a standard 120/80 mmHg sys/dia measurements) may be included in the calibration data 155. In some implementations, the calibration factors may be adjusted retroactively once the user enters valid calibration data. Calibration data may also be imported from the user's medical records if, for example, the device is dispensed to the user by their medical professional.

Because the baseline of PPG is modulated by respiration, a signal representing respiratory rate is typically within the 0-1 Hz range of PPG, and can be obtained using low pass filtering. This is illustrated in FIG. 1C, where the PPG data 150 is passed through the low pass filter (LPF) 152 and optionally combined with the output of another LPF 135 (used for low pass filtering the MoCG data) to obtain biometric parameters such as sleep data 142 and respiratory rate 143. An example of determining the respiratory rate 143 from the PPG data 150 is illustrated in FIG. 1E. In this example, the plot 166 represents the raw PPG data, and the plot 168 shows the output of the LPF 152 representing the low frequency variations due to respiration.

In some implementations, other biometric parameters may also be computed. For example, by using multiple LEDs of different colors in the optical sensor 110, blood oxygenation ($SpO_2$) can be obtained using pulse oximetry theory. Computation of other biometric parameters is described below. Referring again to FIG. 1B, the device 100 can also include a computing device 115 that can be configured to compute the biometric parameters, including, for example, blood pressure, respiratory rate, blood oxygen, stroke volume, cardiac output, and temperature. In some implementations, an activity index 148 (which may be the activity index 127, also shown in FIG. 1C) can be used in determining a set of weights 147 used in calculating one or more of the biometric parameters 146.

Figure 2A:
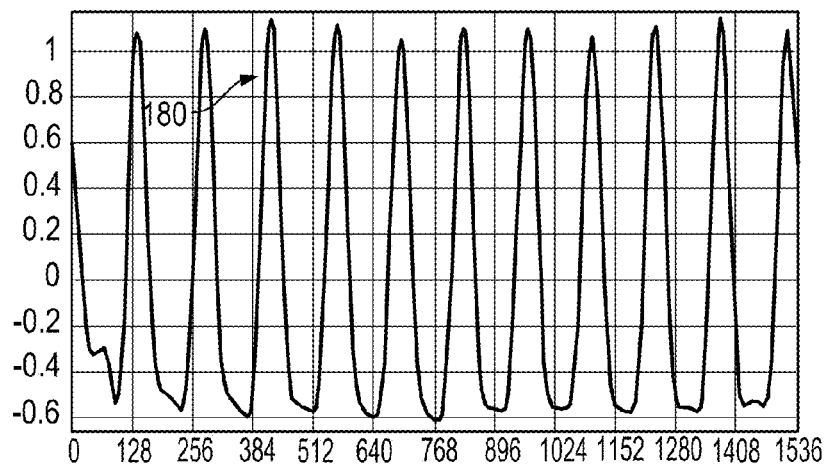
FIGS. 2A-2C, 3, and 4 illustrate plots generated based on data collected by the sensors of the device of FIGS. 1B and 1C.
Figure 2B:
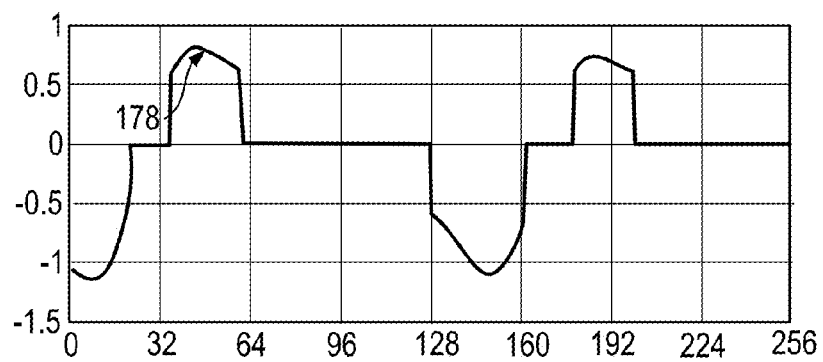

As seen from FIG. 1C, the heart rate information 144 is used in calculating one or more of the biometric parameters 146. In some implementations, the heart rate information 144 can be obtained from the PPG by detecting peaks and/or valleys in a graphical representation (e.g., the plot 162 shown in FIG. 1C) of the PPG data 150. This can include, for example, cross-correlating a portion of the PPG data (e.g., samples or data corresponding to a two second segment of the plot 162 of FIG. 1C) with similar segments to produce a plot 180 (shown in FIG. 2A) representing a series of cross-correlation products. In one example, two-second segments from the plot 162 are cross-correlated with adjacent (possibly with some partial overlap) two-second segments to produce the plot 180 of FIG. 2A. A particular cross correlation result (for example, one that produces the highest cross-correlation amplitude) can then be selected as a template. The plot 178 shown in FIG. 2B is an example of a template. In some implementations, the template can be adjusted to conform to a desired morphology, allowing for a beat to beat natural variation but discounting noise and non-heartbeat signals.

Figure 2C:
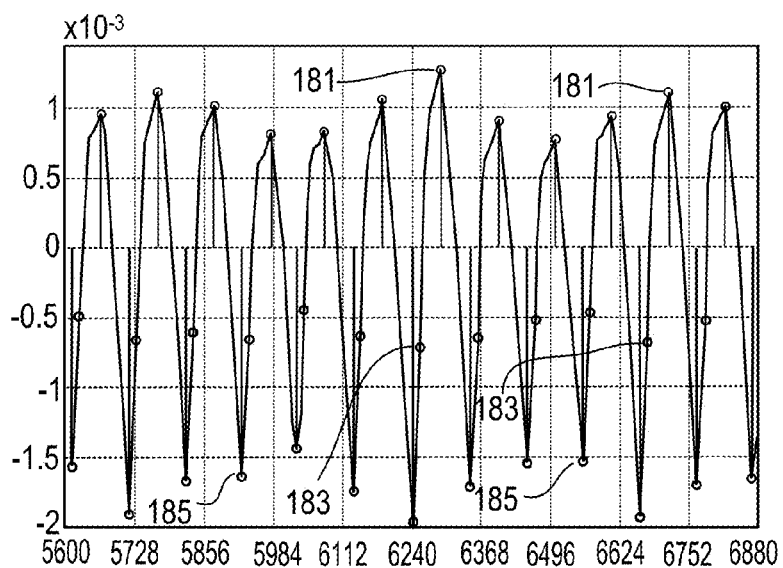

The selected template can then be correlated with segments from the plot 162 (shown in FIG. 1C) to identify locations of correlation peaks. This is illustrated in FIG. 2A, where the plot 180 represents a series of such peaks. The location of the correlation signal peaks can be used to direct a search for valleys, inflection points, and/or peaks within the band pass filtered PPG signal. The inflection point in this case is defined as the point of maximum slope. FIG. 2C illustrates an example of a PPG signal with identified peaks 181, inflection points 183 and valleys 185. For brevity, only a few of the peaks, inflection points, and valleys are marked using the reference numbers 181, 183, and 185, respectively. The distance between two consecutive valleys (or inflection points or peaks) represents a time difference between two consecutive heartbeats, and can be used to compute instantaneous heart rate. For example, if two valleys (or inflection points or peaks) are separated by 141 samples, and if the sampling rate is 128 Hz, the instantaneous heart-rate can be computed as 60*128/141=54.47 beats-per-minute (BPM). The instantaneous heart rate for each of the heartbeats can be plotted as shown in FIG. 3, and can be used for other purposes such as computing other parameters and diagnosing conditions such as arrhythmia.

In some implementations, confidence levels associated with a calculated instantaneous heart rate can be determined before being used in any subsequent analysis. For example, if a person suddenly stands up from a sitting position, the instantaneous heart rate during the transition may shoot up. In some implementations, the rate of such rapid increase can include meaningful information. However, in some implementations, the information obtained during this transition may not be reliable as an indicator of the person's health status. Determining confidence levels associated with the computed heart rates can allow for discarding such outliers in subsequent analyses. In some implementations, a given computed instantaneous heart rate can be compared, for example, to the average (or median) instantaneous heart rate over a predetermined time range (e.g., ±10 seconds) to determine whether the given instantaneous heart rate is reliable. If the given instantaneous heart rate differs (e.g., differs by more than a predetermined amount) from the average heart rate over the predetermined time range, the given instantaneous heart rate may be determined to be unreliable and therefore de-weighed in subsequent computations. This allows for selecting reliable data points at the expense of a short latency (10 seconds in the above example).

Figure 3:
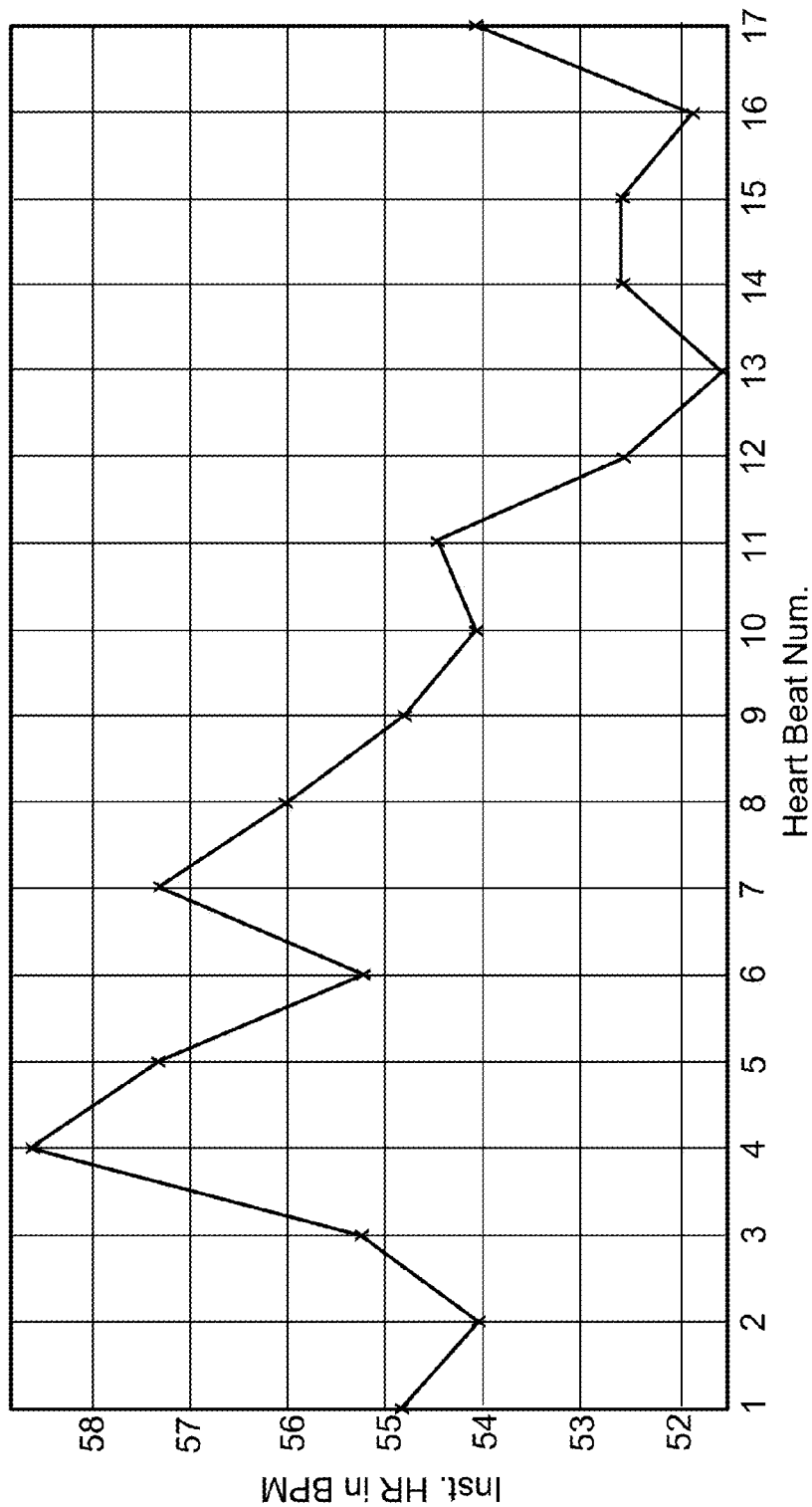
Figure 4:
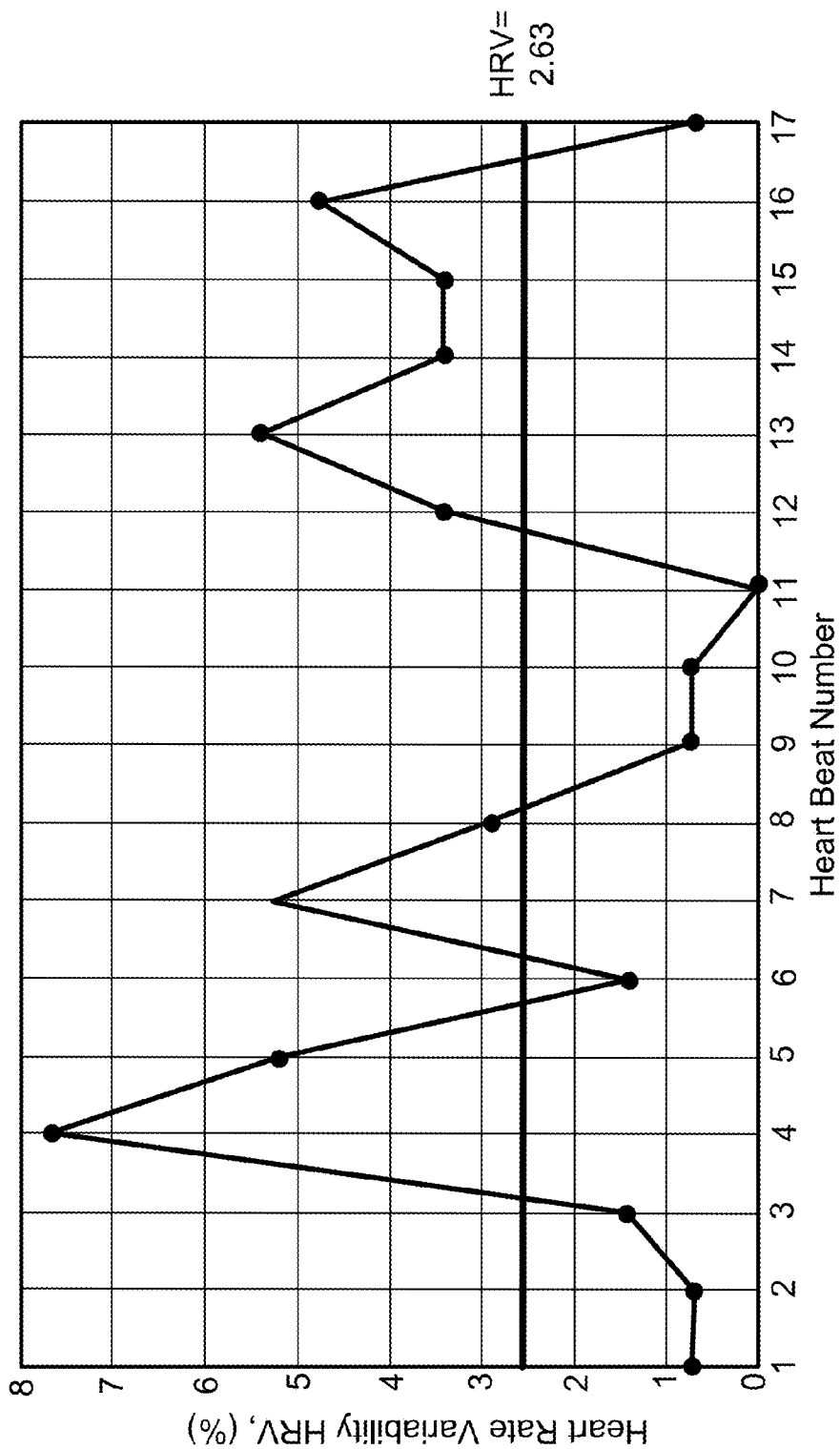

In some implementations, the instantaneous heart-rate data as shown in FIG. 3 can be used for computing instantaneous heart-rate variability (HRV). An example of HRV plotted against the corresponding heartbeats is shown in FIG. 4. As shown in FIG. 4, the HRV data can be used to calculate a mean HRV for a set of heartbeats. In some implementations, HRV data can be used in detecting conditions such as stress. For example, if the mean HRV is above a certain threshold, the subject may be determined to be under higher than usual stress. In the time domain, HRV can be calculated by computing a variance of individual RR intervals (distance between the 'R' points of two consecutive QRS complex curves representing heartbeats, or alternatively the distance between valleys as shown in FIG. 2C) from the average RR interval, over a period of time (e.g., 5 minutes). Alternatively, the HRV can also be calculated in the frequency domain by comparing the power spectrum at very low frequencies (e.g., 0.04-0.15 Hz) with the power spectrum at slightly higher frequencies (e.g., 0.18 to 0.4 Hz).

Figure 5A:
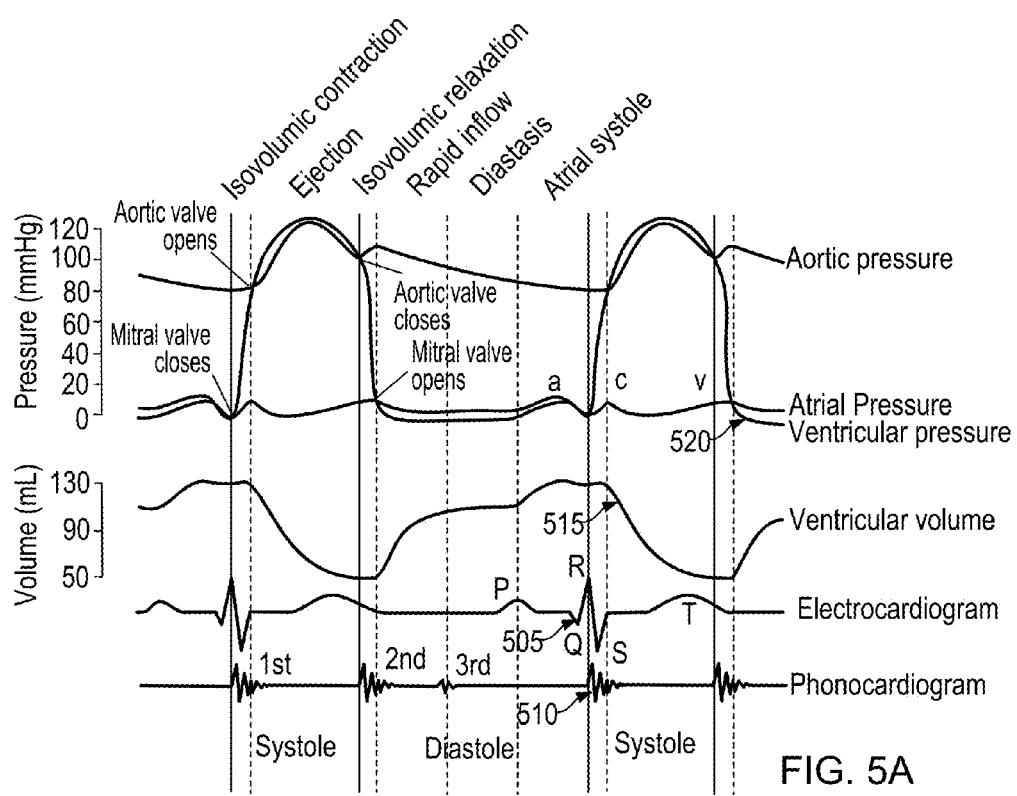
FIGS. 5A-5E illustrate examples of cardiac signals.

Cardiac waveform morphology (also referred to as cardiac morphology) can be defined as the shape of a plot representing cardiac activity. FIG. 5A represents a Wiggers diagram, which is a standard diagram used in cardiac physiology. Referring to FIG. 5A, the shape of an electro-cardiogram (ECG) QRS complex 505 represents a morphology associated with a heartbeat. Cardiac morphology depends on where and how cardiac activity is measured. For example, the morphology 510 of a phonocardiogram signal is different from that of the ECG morphology 505. In another example, the morphology associated with ventricular volume 515 is different from the morphology associated with ventricular pressure 520.

Figure 5B:
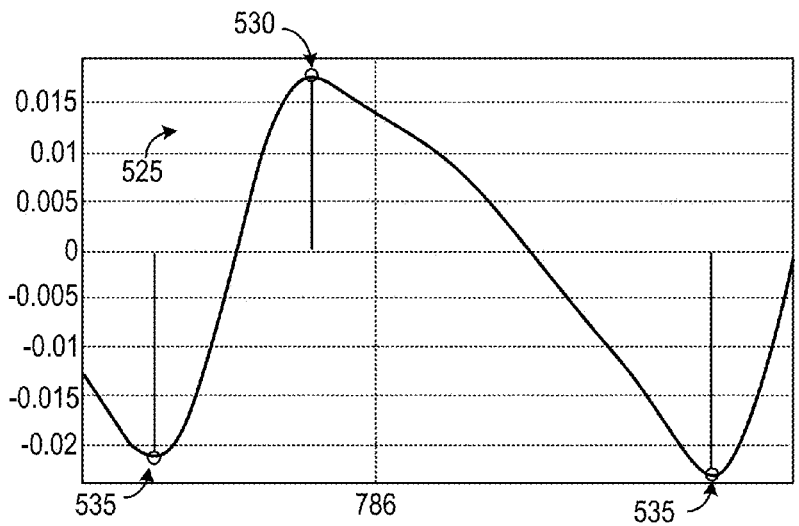

FIG. 5B shows an example of a cardiac signal illustrating the morphology 525 associated with a PPG signal. The morphology of a measured PPG signal can be checked to determine whether the measured PPG signal reliably represents heartbeats. In some implementations, the relative separations of the peaks and valleys of the PPG signal are analyzed to determine whether the PPG signal reliably represents heartbeats. For example, a segment of the PPG signal can be determined to represent heartbeats if the following threshold condition is satisfied:

$$0.25 < \text{Median(peak to valley distances)}/\text{Median(valley to valley distances)} < 0.4$$

The condition above uses the range [0.25, 0.4] as an example, and other values can also be used. For example, the range (or threshold) could be determined for an individual user by using, for example, a range considered to be normal for the particular user. The ratio from the above condition can vary within the range for various conditions of the subject. For example, the ratio can be at a low portion of the range during relaxation or sleep conditions, and at a high portion of the range during stressful events such as anger or fear. In some implementations, other morphology checks can also be performed. For example, one morphology check can involve verifying that at a resting position, the user's systolic amplitude is approximately half of the diastolic amplitude. In some implementations, segments that do not satisfy the morphology check conditions are discarded from being used in biometric parameter computations.

Figure 5C:
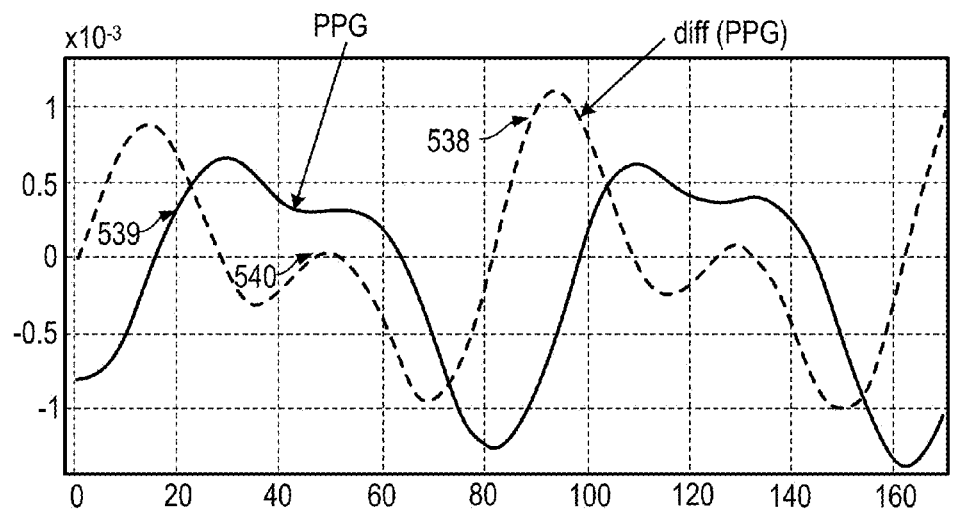
Figure 5D:
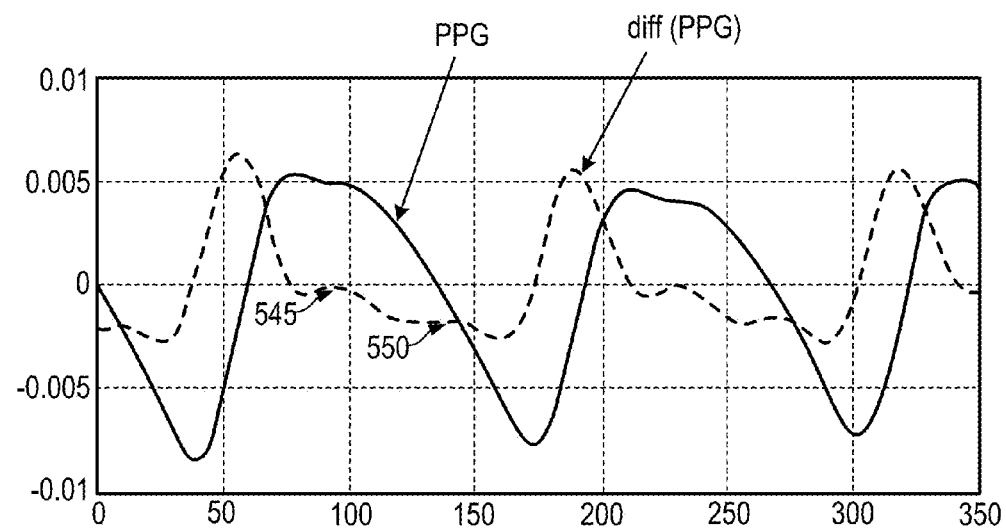
Figure 5E:
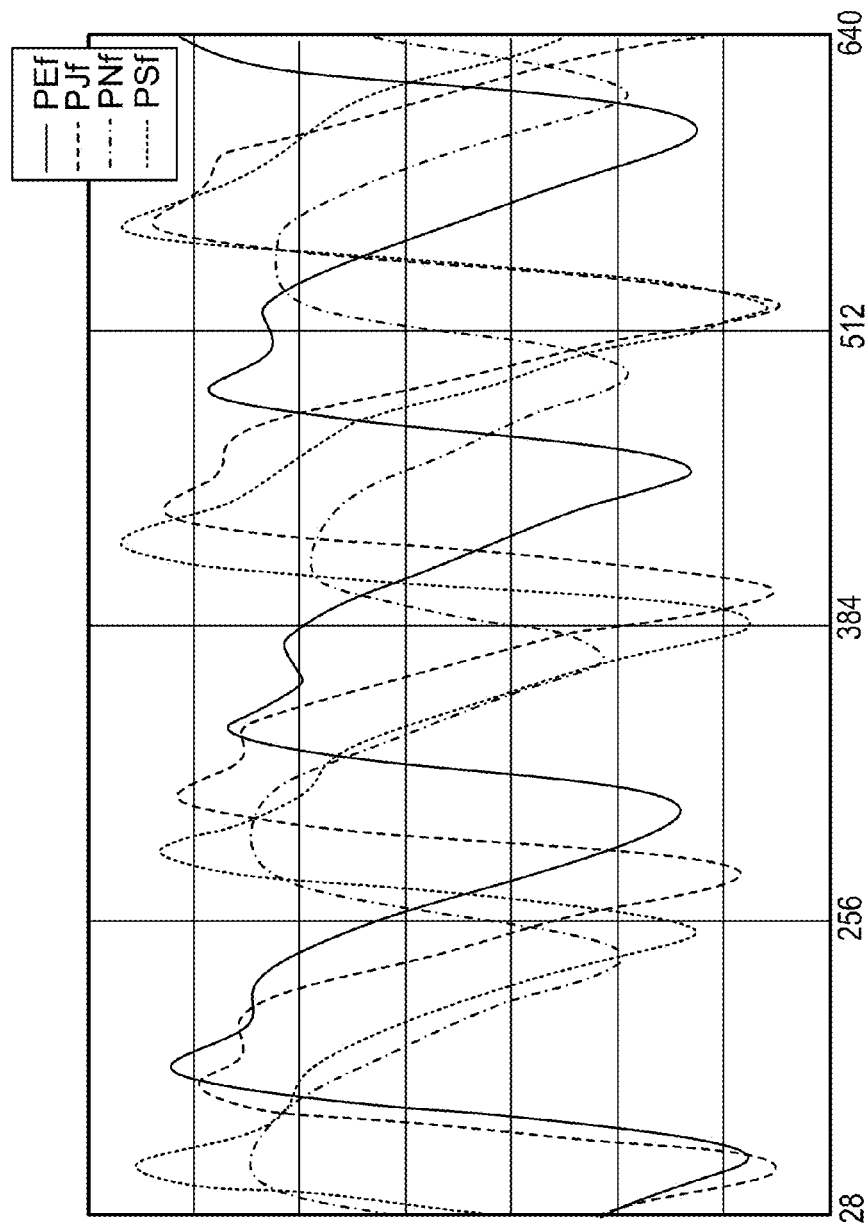

Cardiac morphology also typically varies from one person to another due to, for example, unique heart beat signatures, breathing patterns and the unique 'transmission line' reflection signatures that are caused by the lengths and stiffness of an individual's arteries. In A typical PPG signal the main peak represents the first systolic peak which is followed by the secondary peak (or bump) representing the early diastolic peak (or reflection). The time between the two peaks is also inversely proportional to arterial stiffness. This is easier to visualize from the first and/or the second derivatives of the PPG signal. FIGS. 5C and 5D show examples of cardiac signals illustrating morphology based on PPG signals. In the example of FIG. 5C, the derivative 538 of the PPG signal 539 shows a discernible second peak 540, whereas in the example of FIG. 5D, the corresponding second peak 545 is comparatively weaker. However, the example of FIG. 5D shows the presence of a third peak 550. Therefore, in some implementations, cardiac morphology can be used as a biometric identifier. For example, the device 100 described with reference to FIG. 1B can be configured to verify, based on a determined cardiac morphology, that the person wearing the device is the person for whom the device was assigned. In some implementations, the determined cardiac morphology may also be used to uniquely identify a wearer of the device 100. Such biometric identification can be used, for example, in security and accessibility applications. For example, the device 100 can be configured to transmit a cardiac morphology based signature to a receiver (e.g., on a mobile phone, or at secured access point) to gain access to a secure resource. In some implementations, when a same device is used by multiple individuals (e.g., different members of a family), the wearer of the device may be identified based on the identified cardiac morphology of the wearer. FIG. 5E shows examples of cardiac signals illustrating morphology for four different individuals, and illustrates how the cardiac morphology varies from one person to another.

Security Applications

In some implementations, multiple measured or derived parameters can be used as a biometric signature to uniquely identify a wearer. For example, a wearer can be identified based on a multi-dimensional space defined based on the measured or derived parameters. Because the parameters vary from one person to another, each person would be mapped to a different region within the multi-dimensional space. A simple two-dimensional example of such a space can be defined, for example, by using heart rate as one axis and PPG shape as the second axis. Because the PPG shape and heart rate varies from one person to another, each person can typically be mapped to a separate region on the two-dimensional plane, and can be identified based on a location of the region. Higher dimensional spaces can be used for robustly identifying individuals among a large population. Examples of parameters that can be used as axes for such spaces include cardiac morphology, heart rate, cardiac volume, PPG, or other parameters derived as a function of one or more of these parameters. In another example, cardiac morphology can be combined with another parameter such as the MoCG morphology to achieve increased accuracy and/or resolution for bio-authentication applications. Examples of such applications include access control, digital wallet authorization, digital passwords/signature and environmental control. In such cases, MoCG data can be used to provide a MPTT signature and/or a MoCG signature waveform that may be unique to a particular user.

In some implementations, the biometric signature based user identification can be used in electronic payment applications. In some implementations, the device 100 can be configured to communicate with a payment gateway using, for example, near field communication (NFC) or Bluetooth Low Energy (BLE) protocols. The payment gateway can be configured to identify the user based on a corresponding biometric signature to initiate the payment process. The payment gateway can communicate the identification information to a server that stores credit card or bank information of the corresponding user, for example, within a corresponding user account. Upon receiving identification of the user, the server may initiate communications with the payment gateway that result in the credit card being charged or the bank account being debited.

In some implementations, the biometric signature based user identification is disabled if the device determines that the wearer is under distress. The device can determine whether the wearer is under distress based on the wearer's vital signs (e.g., such as heart rate (HR), heart rate variability (HRV), blood pressure (BP), and respiratory rate). For example, if a wearer of the device is being forced to access a payment gateway, the device can detect the wearer's distress, as indicated by a sudden increase in HR, BP, and/or respiratory rate, and prevent him or her from accessing the payment gateway. Similarly, in some examples, if a wearer of the device is being forced to unlock a lock (e.g., a lock on a door of the wearer's home), the device can detect the wearer's distress, as indicated by a sudden increase in HR, BP, and/or respiratory rate, and prevent him or her from unlocking the lock.

In some implementations, the wearer's vital signs do not produce a match of the wearer's biometric signature when the wearer is under distress. For example, when the wearer is under distress, the multi-dimensional space defined based on the measured or derived parameters takes on a modified for that does not match the wearer's biometric signature. As such, a wearer under distress is unable to be identified by the biometric signature.

In some cases, a wearer may exhibit signs that are synonymous with distress when the wearer is not in fact in distress. For example, if the wearer is involved in a non-dangerous and exciting event, such as buying an extremely expensive item, the wearer may experience an increase in HR, BP, and/or respiratory rate that may mistakenly be interpreted by the device as signs of distress. Thus, in some implementations, the wearer is provided with an opportunity to authenticate himself or herself in the event that the device detects false signs of distress or fails to identify the biometric signature of the wearer. The wearer can authenticate himself or herself using confidential information such as a password or a personal identification number that is communicated to the device or a server in communication with the device. In some implementations, the wearer can authenticate himself or herself by performing a private, predefined gesture. The one or more motion sensors of the device can be configured to determine whether the authenticating gesture matches the predefined gesture.

Figure 6A:
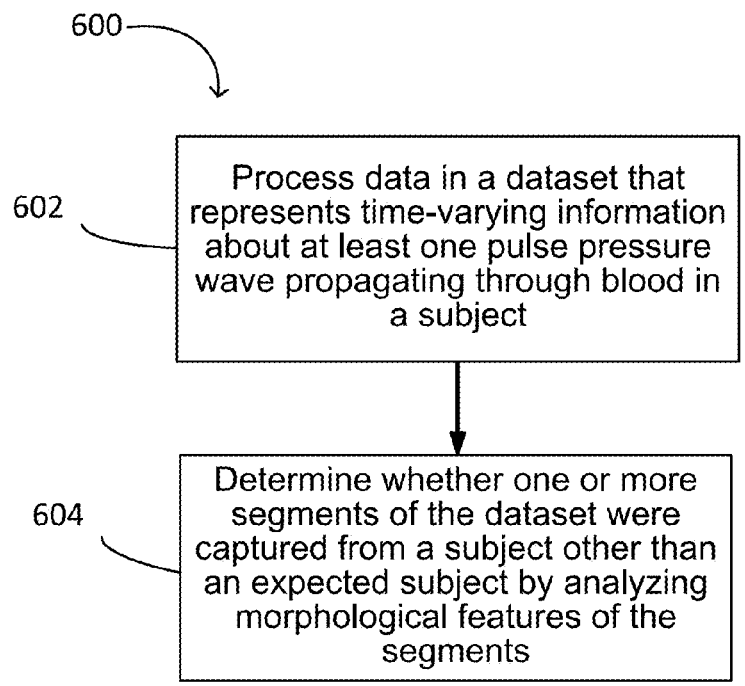
FIGS. 6A-6C are flowcharts depicting example processes for biometric authentication.

An example process 600 of bio-authenticating a subject is shown in FIG. 6A. A machine, such as a processor, that receives information from the optical sensors 110 of the device 100 can perform one or more steps of the process 600. In some implementations, the machine can include the computing device 115 described above with reference to FIG. 1B. In the process 600, initially, data in a dataset that represents time-varying information about at least one pulse pressure wave propagating through blood in a subject can be processed (602). The data can be acquired at a location of the subject (e.g., the arm or the wrist of the subject). A determination can then be made of whether one or more segments of the dataset were captured from a subject other than an expected subject (604). The determination can be made by analyzing morphological features of the segments.

Figure 6B:
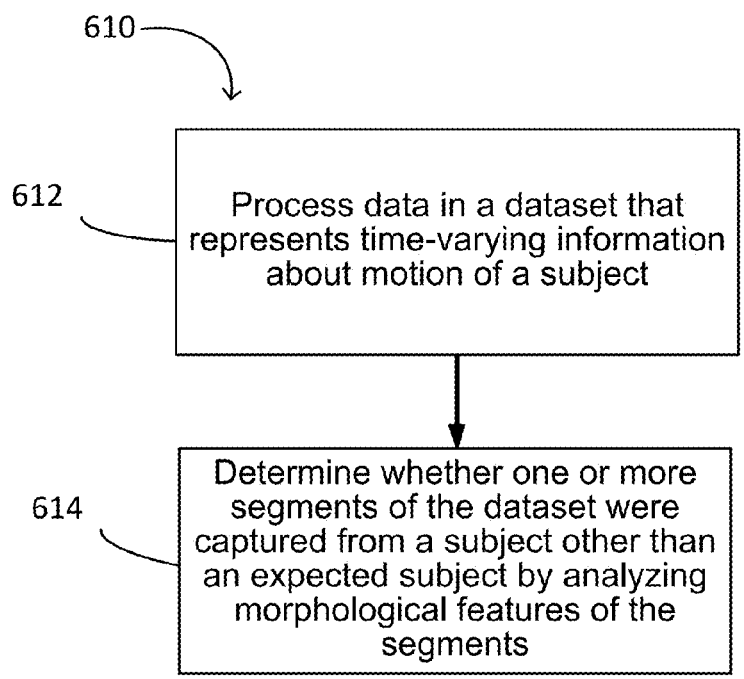

Another example process 610610 of bio-authenticating a subject using information about motion of the subject is shown in FIG. 6B. A machine, such as a processor, that receives information from the motion sensor 105 of the device 100 can perform one or more steps of the process 610610. In some implementations, the machine can include the computing device 115 described above with reference to FIG. 1B. In the process 610, initially, data in a dataset that represents time-varying information about motion of a subject can be processed 612). The data can be acquired at a location of the subject (e.g., the arm or the wrist of the subject). A determination can then be made of whether one or more segments of the dataset were captured from a subject other than an expected subject 614). The determination can be made by analyzing morphological features of the segments.

Figure 6C:
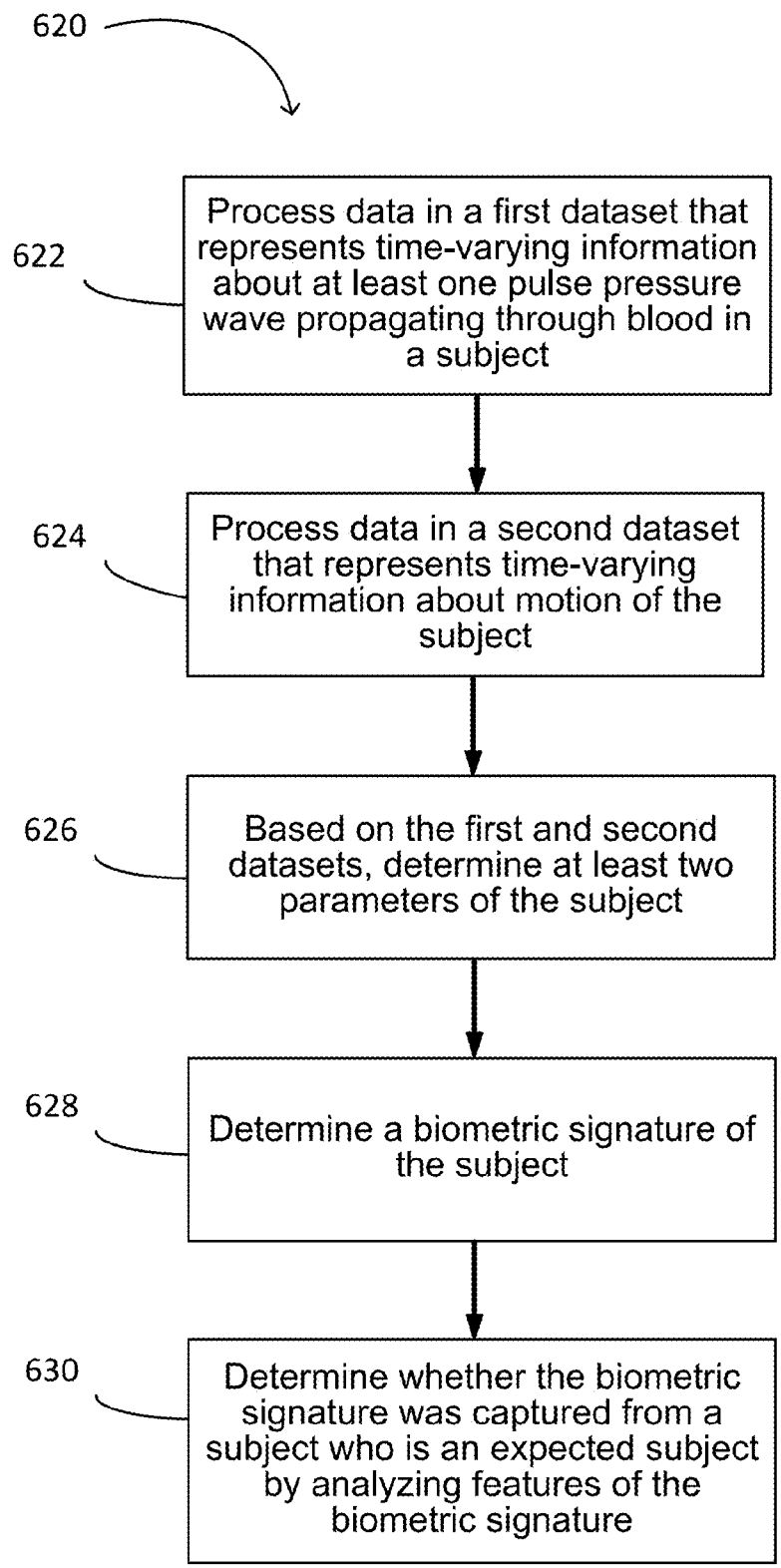

Another example process 620 of bio-authenticating a subject is shown in FIG. 6C. A machine, such as a processor, that receives information from the motion sensor 105 and the optical sensors 110 of the device 100 can perform one or more steps of the process 620. In some implementations, the machine can include the computing device 115 described above with reference to FIG. 1B. The machine may also use the calculated MPTT to further generate additional biometric measurements, the processes for which are discussed below. In the process 620, initially, data in a first dataset that represents time-varying information about at least one pulse pressure wave propagating through blood in a subject can be processed (622). Data in a second dataset that represents time-varying information about motion of the subject can also be processed (624). The data can be acquired at a location of the subject (e.g., the arm or the wrist of the subject). Based on the first and second datasets, at least two parameters of the subject can be determined (626). The parameters can include one or more of blood pressure, respiratory rate, blood oxygen levels, heart rate, heart rate variability, stroke volume, cardiac output, MoCG morphology, and PPG morphology. A biometric signature of the subject can then be determined (628). In some implementations, the (628). The biometric signature can be represented in a multi-dimensional space. Each axis can correspond to at least one of the determined parameters. A determination can then be made of whether the biometric signature was captured from a subject who is an expected subject (630). The determination can be made by analyzing features of the biometric signature.

In some implementations, the biometric signature based user identification can be used in providing rewards and/or discounts to a user. For example, if the identified user is determined to be adhering to a particular exercise regimen, reward points or incentives such as discounts on particular products can be credited to the corresponding user account. Therefore, a user can be motivated to keep adhering to particular good practices to keep getting such rewards or discounts.

Motion Pulse Transit Time (MPTT) Calculation

Figure 7A:
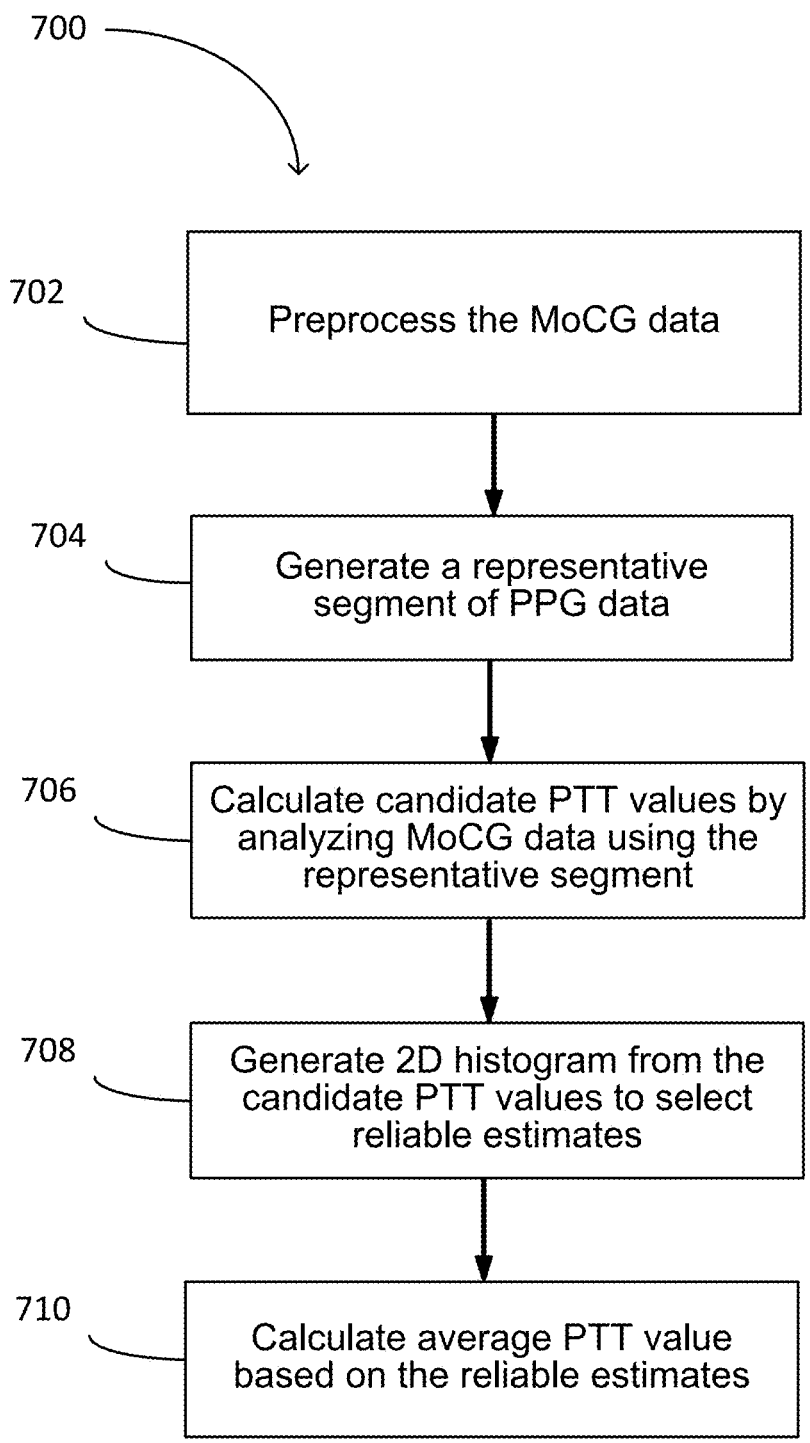
FIG. 7A is a flowchart depicting an example of a process for calculating motion pulse transit time (MPTT).

The information collected from the motion sensors 105 and the optical sensors 110 of FIG. 1B is used to calculate the MPTT, which can be used to further calculate the biometric parameters, such as blood pressure, stroke volume, etc. An example process 700 for the MPTT calculation is shown in FIG. 7A. A machine, such as a processor, that receives the information from the motion sensors 105 and the optical sensors 110 can perform one or more steps of the process 700700. The machine may further provide the calculated results to, for example, the wearer, another person who is interested and authorized to receive the information, or another machine for further data processing or data storage. In some implementations, the machine can include the computing device 115 described above with reference to FIG. 1B. The machine may also use the calculated MPTT to further generate additional biometric measurements, the processes for which are discussed below.

Figure 8:
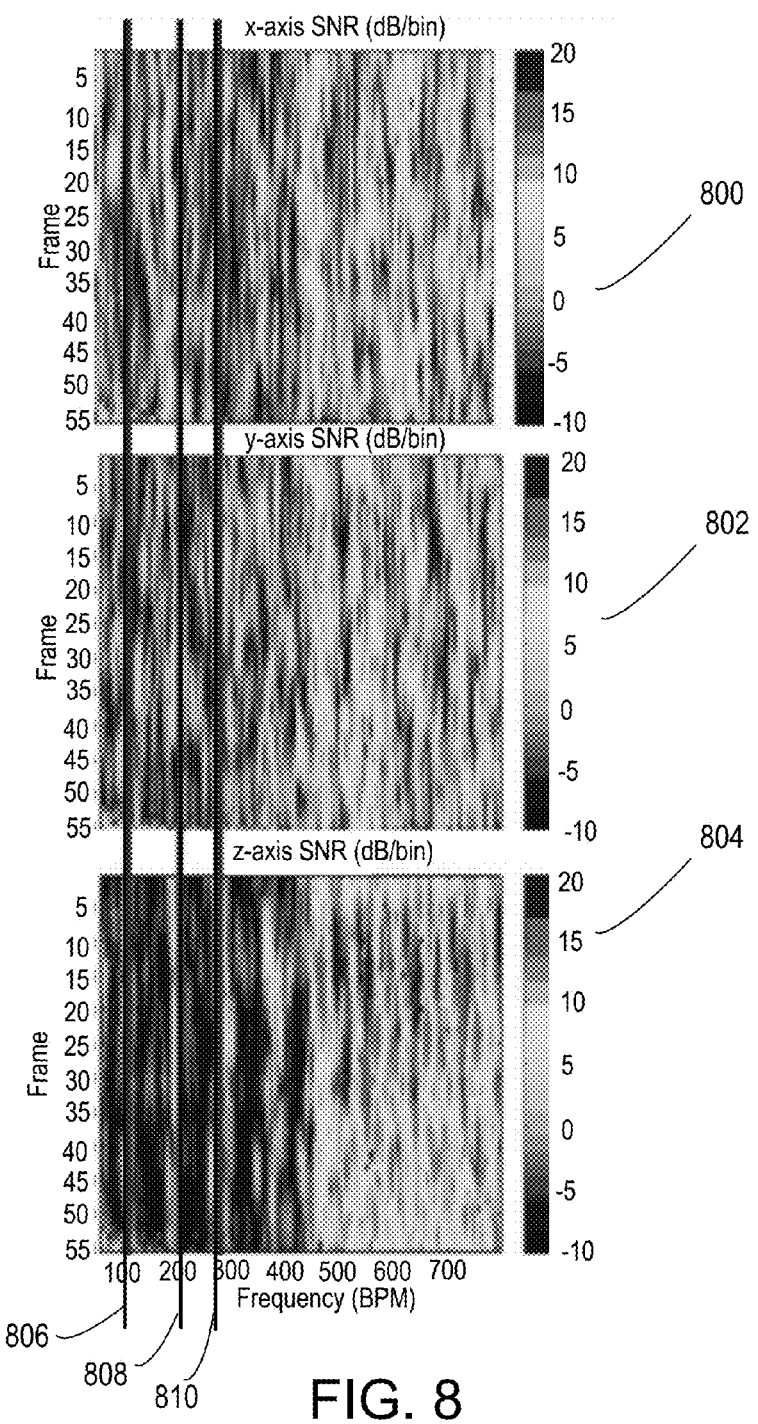
FIG. 8 shows examples of heat maps that relate to data collected from the motion sensors of the device of FIGS. 1B and 1C, and are used in determining weights for data corresponding to accelerometers oriented along different axes.

In the process 700, initially, the MoCG data for use in the MPTT calculation can be preprocessed (702). During any time period, the motion sensor or sensors (e.g., the accelerometers) collect three sets of MoCG data along three orthogonal axes, x, y, and z, or along polar coordinates. The three sets may be combined by selecting a weight, $w_x$, $w_y$, $w_z$ for each set and summing the weighted sets. An example of the weight selection is shown in FIG. 8, which illustrates two dimensional heat-map diagrams 800, 802, and 804 produced from power spectra of MoCG ensembles collected over time. In each of the diagrams 800, 802, 804, the horizontal axis represents the frequency and the vertical axis represents frames of MoCG data collected over time. Therefore each row in the diagrams represents the power spectrum of a corresponding frame of MoCG data. The colors represent the values of the energy level. The weights $w_x$, $w_y$, $w_z$ can be assigned, using respective diagrams, based on the ratio of energy inside the heart rate range to the energy outside the heart rate range. If the power spectra is consistent across the different frames and/or is a harmonic of the already calculated heart rate (as illustrated in the diagram 804), the corresponding axis (the z axis in this example) is assigned a higher weight than the other axes. The lines 806, 808, and 810 in FIG. 8 represent the first, second, and third harmonic, respectively of the measured heart rate in this time segment. In the example shown in FIG. 8, the assigned weights are $w_x$=0.03, $w_y$=0.15, and $w_z=0.95$. The MoCG data for the MPTT calculation is then calculated as the weighted sum of the three sets of MoCG data for the three axes. Alternatively, a single axis can be selected (e.g., the axis with the highest weight) while ignoring the others. For example, only the z axis can be selected for the example shown in FIG. 8. In some implementations, axis selection can be performed by independently analyzing each axis and then combining the axes based on agreement of the candidate MPTT values. This may be done, for example, to avoid the calculation of a power spectrum signal without sacrificing on the accuracy.

Figure 9:
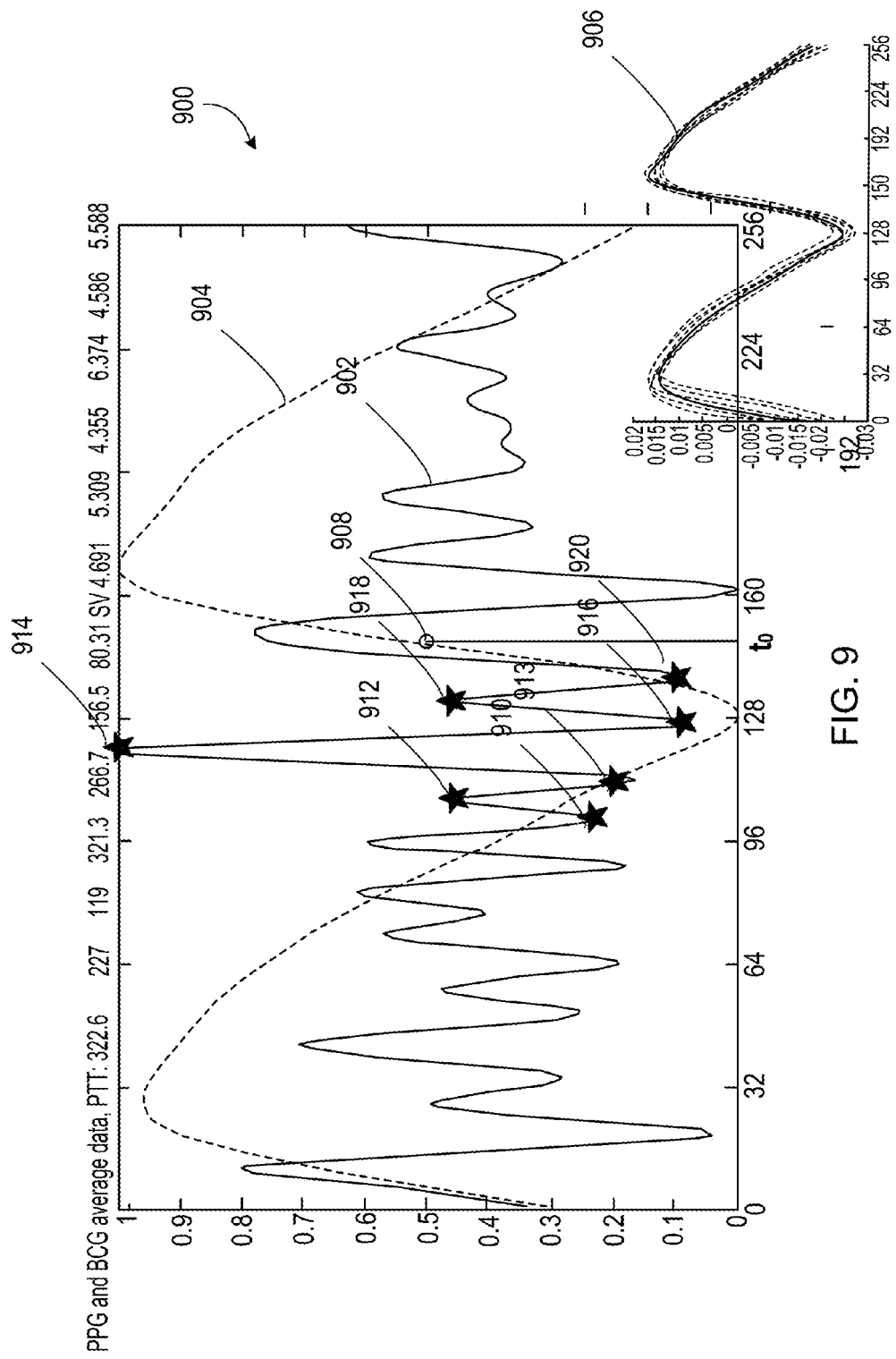
FIGS. 9, 10A-10C, 11A, and 11B illustrate plots used in calculating MPTT.

Referring again to FIG. 7A, a representative segment of the PPG data is generated (704704) for calculating the PPT. In some implementations, the representative PPG segment is generated by averaging across multiple PPG segments of the same length. FIG. 9 shows an example of the representative segment 904 of the PPG data used in determining the MPTT. The representative segment 904 in this example is calculated by averaging across multiple segments 906 of equal duration. The MoCG data is then analyzed using the representative segment (706) to calculate candidate MPTT values. The representative segment can be calculated, for example, by averaging across multiple segments of equal duration arranged on the same time grid as a representative PPG signal. A short segment of the MoCG data 902 (of equal duration to the representative segment 904) and the representative segment 904 are aligned in time, for example, by aligning inflection points (or valleys or peaks). The length of the segment 904 and the corresponding MoCG data can be in the order of several seconds. In the example shown in FIG. 9, the length of the segment 904 is 2 seconds. However segments of other lengths (e.g. 1.5 seconds-5 second) can also be used. In some implementations, the representative segment is generated from data collected when a user is stationary, so that the data does not include a significant amount of unwanted noise.

In some implementations, the MPTT is measured as the difference between a time point $t_0$ when a mid-systole portion 908 of the representative PPG segment 904 is measured, and a second time point representing the portion of MoCG data corresponding to the mid-systole. Because the MoCG data represents the motion due to an actual heartbeat, and the PPG data represents a pulse wave arrival recorded at a distance from the heart, the second time point generally occurs before $t_0$. Since a human body is not a rigid body, as defined by the laws of mechanics, the MoCG pulse arrives at the location where the device is located in a somewhat delayed (but constant per individual) fashion. The portion of MoCG data corresponding to the mid-systole is typically manifested as a peak or valley in the MoCG data, and the MPTT can be determined by identifying the correct peak or valley corresponding to the mid-systole. While mid-systole is used as a reference point in this example, other portions of the cardiac morphology can also be used as the reference point. Based on a priori knowledge of typical MPTT, a predetermined time range relative to $t_0$ is searched and the peaks and valleys detected within the predetermined time range are flagged as potential candidates for being the correct peak or valley corresponding to the mid-systole. Therefore, the difference between the time point corresponding to each such valley or peak and the time to represents a hypothetical MPTT. The correct MPTT value is determined based on the hypothetical MPTTs, as described using the example below.

The predetermined time range can be chosen to be, for example, between 10 to 400 ms, or another duration longer than an actual expected range. Within the predetermined time range, seven peaks and valleys 910, 912, 913, 914, 916, 918, 920, corresponding to time points $t_1, t_2, t_3, t_4, t_5, t_6, t_7$, respectively, are identified on the MoCG plot 902. Accordingly, seven hypothetical MPTTs are determined as, $h_1=t_0-t_1$, $h_2=t_0-t_2$, $h_3=t_0-t_3$, $h_4=t_0-t_4$, $h_5=t_0-t_5$, $h_6=t_0-t_6$, and $h_7=t_0-t_7$.

Figure 10A:
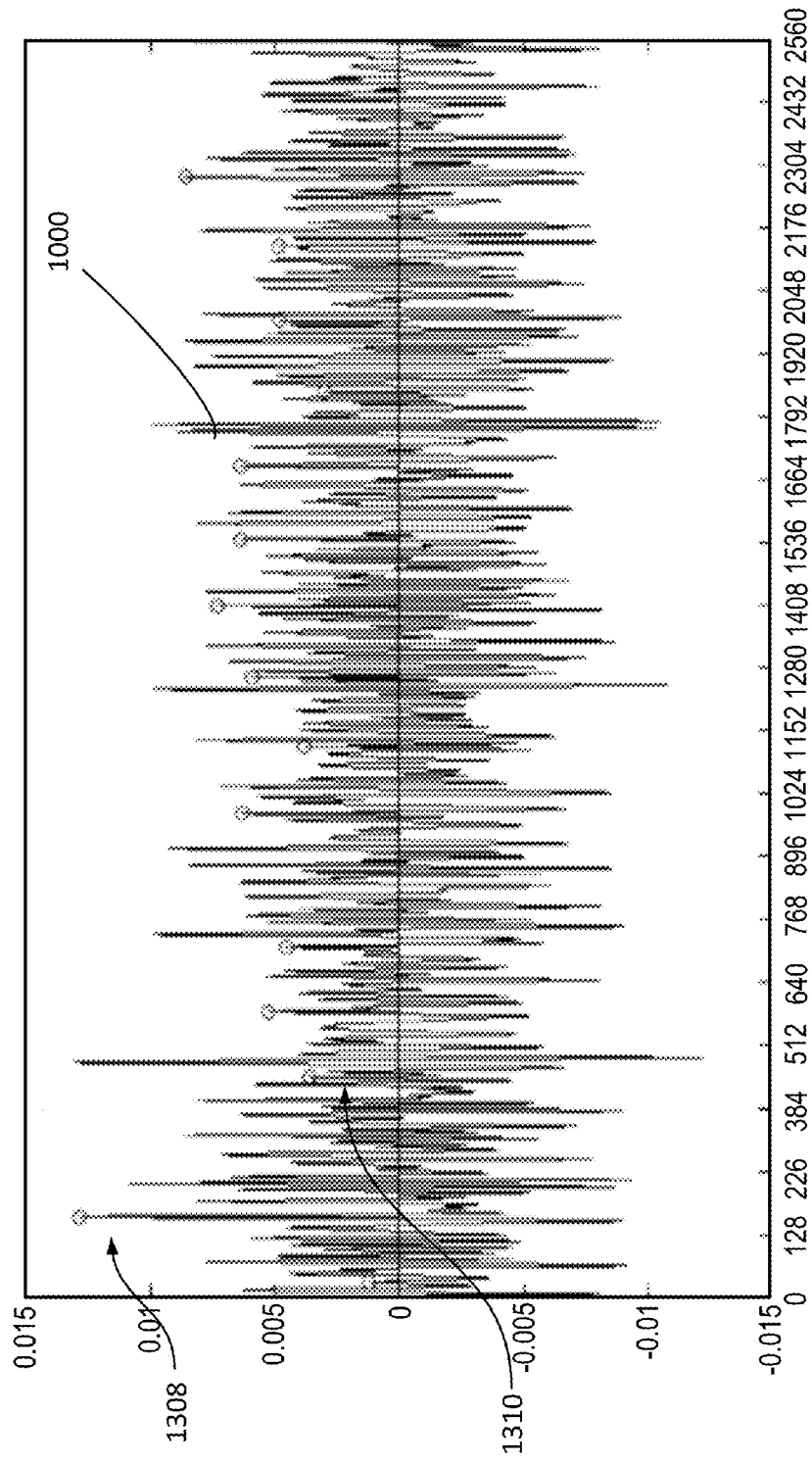

Next, for a given hypothetical MPTT (e.g., $h_1$), a longer segment 1000 of the MoCG data (e.g., of 20 second duration, as shown in FIG. 10A) is aligned with the corresponding PPG data, and the time points corresponding to mid-systoles in the PPG pulses are identified as reference points. The MoCG data is checked at each time point preceding the reference points by $h_1$ (and possibly within a small time range around such time points) for the presence of a peak or valley. If a peak or valley is detected, it is flagged, and the total number of flagged peaks and valleys for the entire segment of MoCG data are recorded. FIG. 10A illustrates a 20 second segment of MoCG data, along with flagged peaks and valleys corresponding to one particular hypothetical MPTT. In the example of FIG. 10A, the flagged peaks and valleys are identified by markers (e.g., circles) 1008, 1010.

Figure 10B:
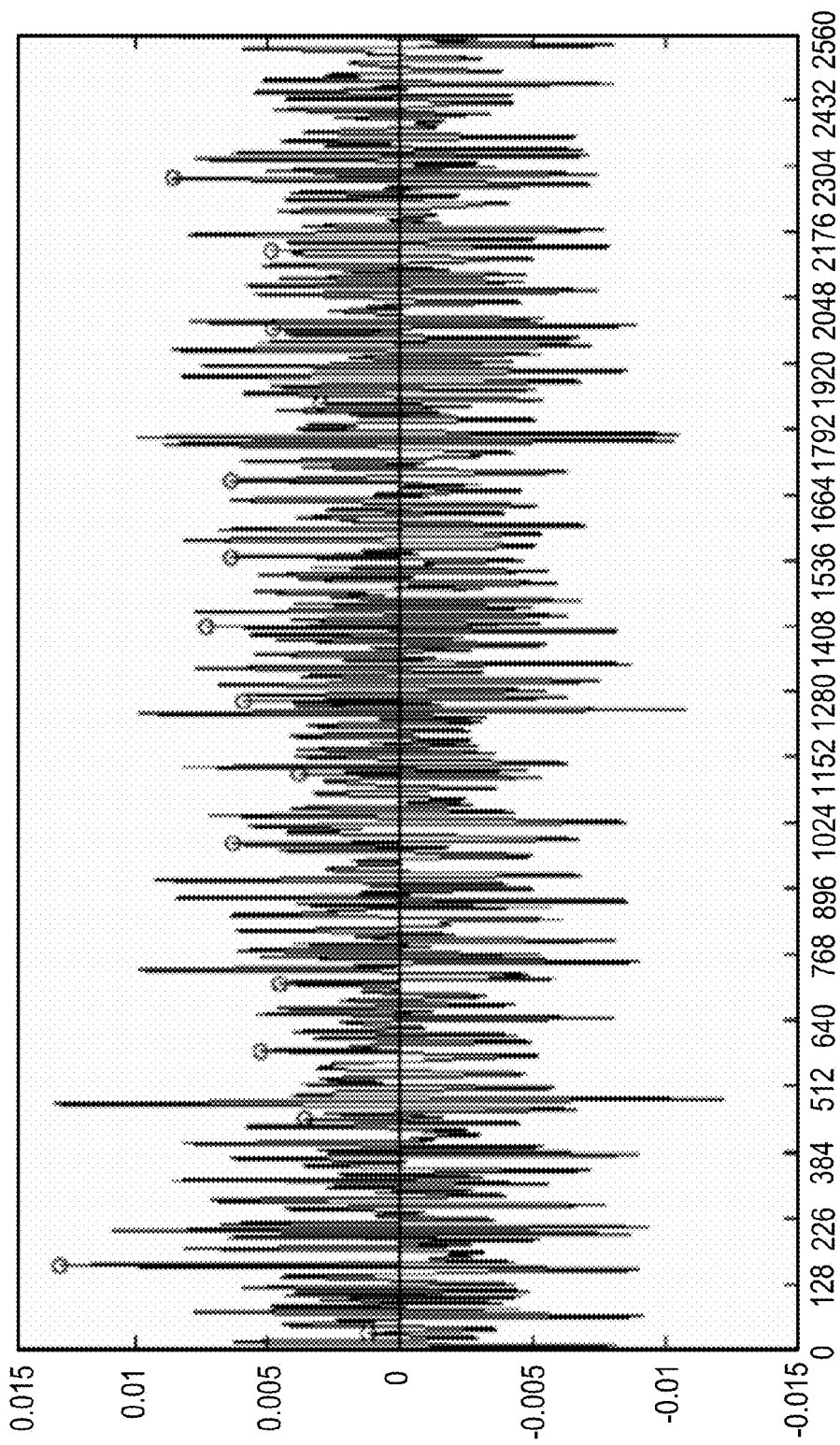
Figure 10C:
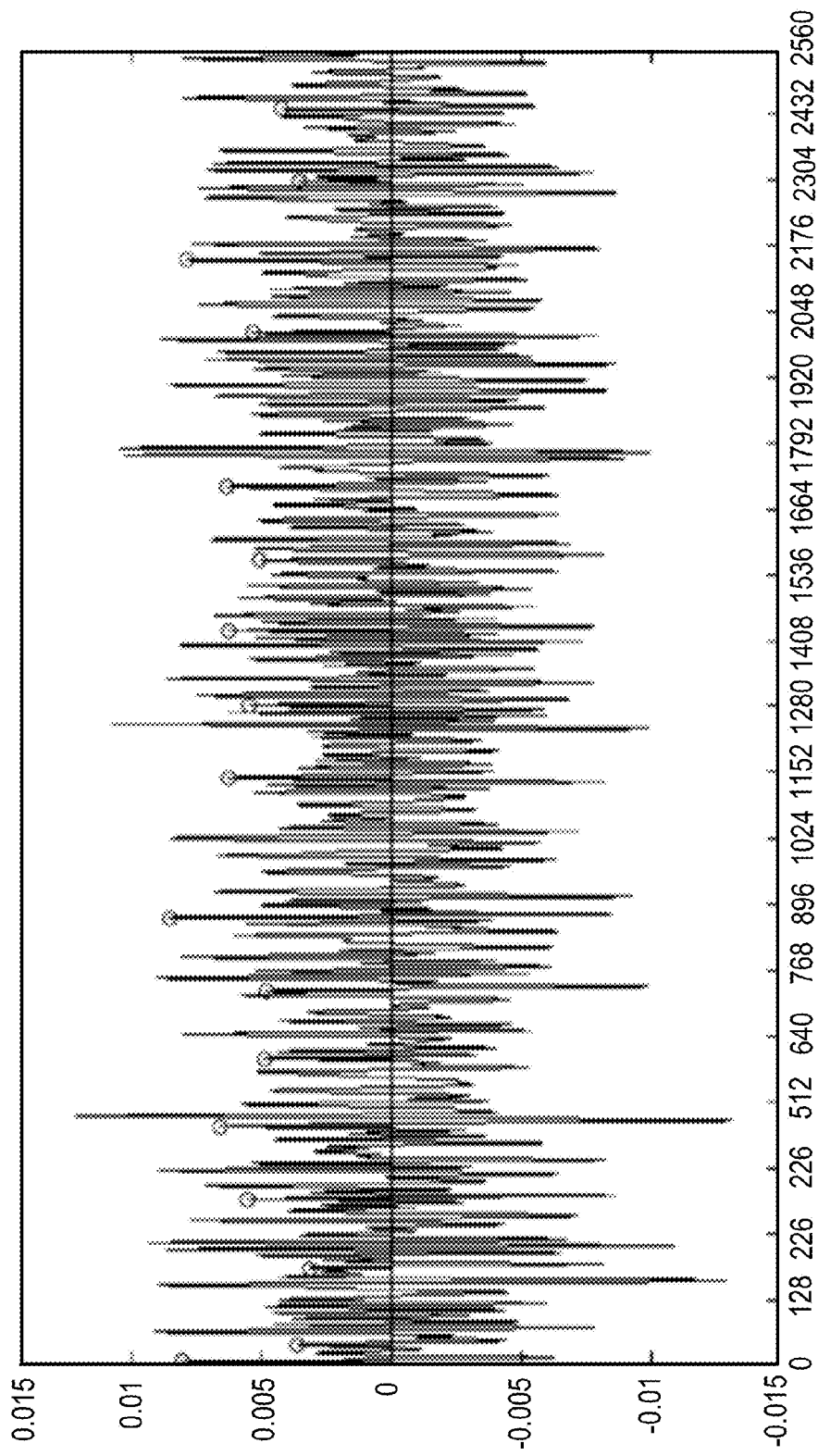

The above process is repeated for each of the hypothetical MPTTs and the total number of peaks or valleys are recorded for each case. The plots corresponding to two other hypotheses are illustrated in FIGS. 10B and 10C. In some implementations, one of the hypothetical MPTTs is chosen as the true MPTT value, based on the recorded number of peaks or valleys. For example, the hypothetical MPTT that yields the maximum number of peaks or valleys can be chosen as the true MPTT value. In some implementations, the hypothetical MPTTs can be combined together as a weighted sum to obtain the true MPTT value. The weights can be assigned based on, for example, a ratio of the number of flagged peaks (or valleys) to the total number of reference points, and a consistency of the flagged peaks (or valleys) defined as a signal-to-noise ratio:

$SNR$=mean(amplitudes of flagged peaks)/standard deviation(amplitudes of flagged peaks)

A weight for a given hypothetical MPTT can then be determined as:

Weight=((Number of flagged peaks)/(total reference points))$^2$*log ($SNR$)

Figure 11A:
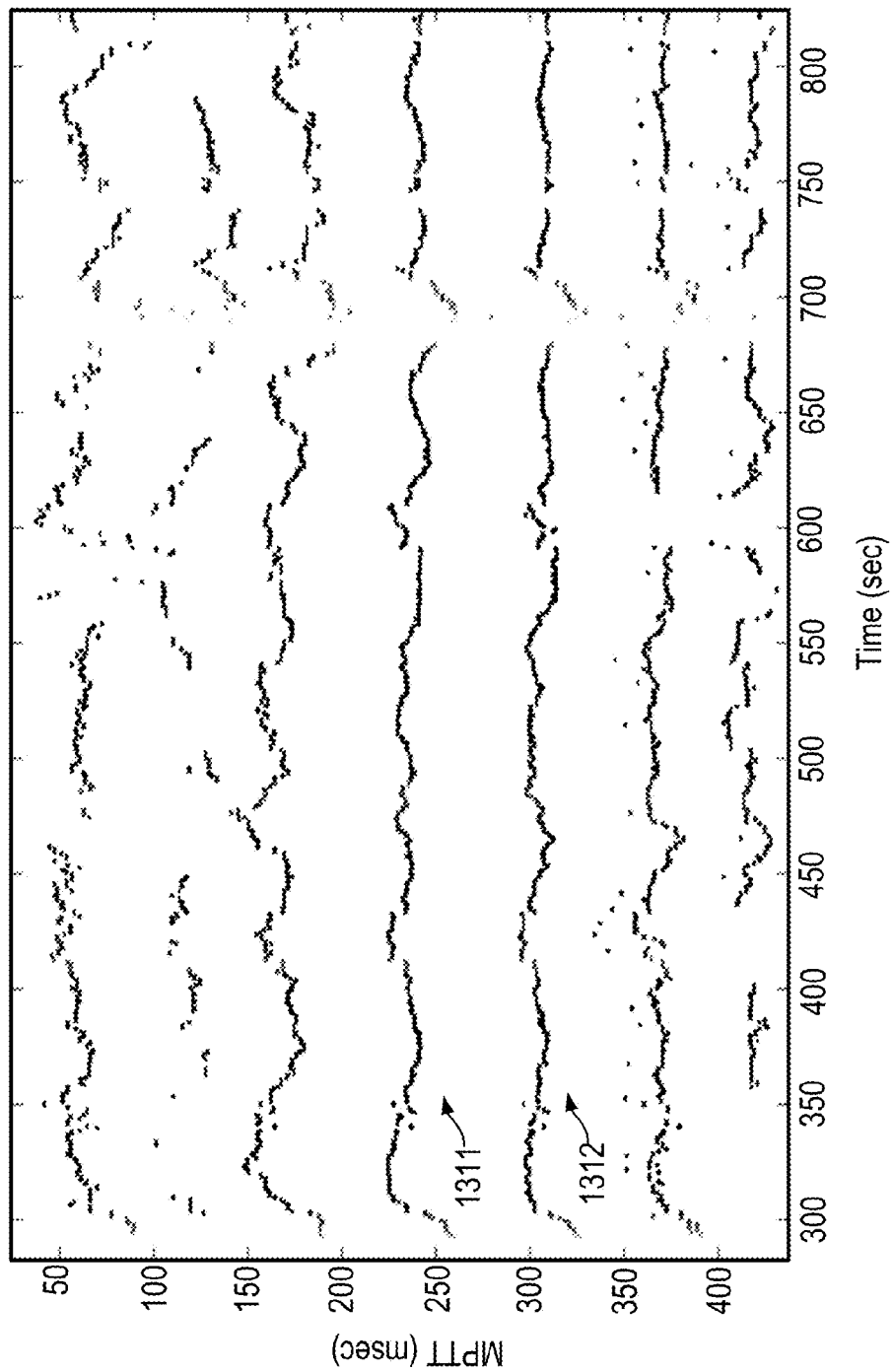

Next, a 2D histogram or is generated (708) from the MPTT values calculated during a predetermined time range. For example, the predetermined time range can be the duration for which a user wears the device 100. An example of such a histogram is shown in FIG. 11A, where the y axis represents a calculated MPTT value (averaged over 60 seconds), the y axis represents time, and the darkness of each point represents calculated confidence measure associated with the calculated MPTT. The different horizontal sets represent candidate MPTT values for different time ranges. A representative set can be selected from the candidate sets based on, for example, a priori knowledge about the expected MPTT, and/or confidence measures associated with the points in the set. For example, from FIG. 11A, the sets 1111 or 1112 can be selected as the best representative sets for the MPTT, based on the confidence levels associated with the points (as represented by the darkness of the points), as well as a priori knowledge that the MPTT is expected to be within a 250-350 ms range. Therefore, more consistent (and hence reliable) estimates of MPTT values can be identified from the histograms, and the average MPTT value over the predetermined time range can be calculated (710), for example, as an average of the consistent MPTT values. Inconsistent MPTT values can be discarded from being included in computing the average MPTT. Other parameters such as average SV can also be calculated using similar plots. Before generating such plots, individual estimates of SV (in ml/heartbeat) can be calculated from the amplitude of the MoCG signal based on the fact that SV varies directly with the average amplitude of the MoCG.

Figure 11B:
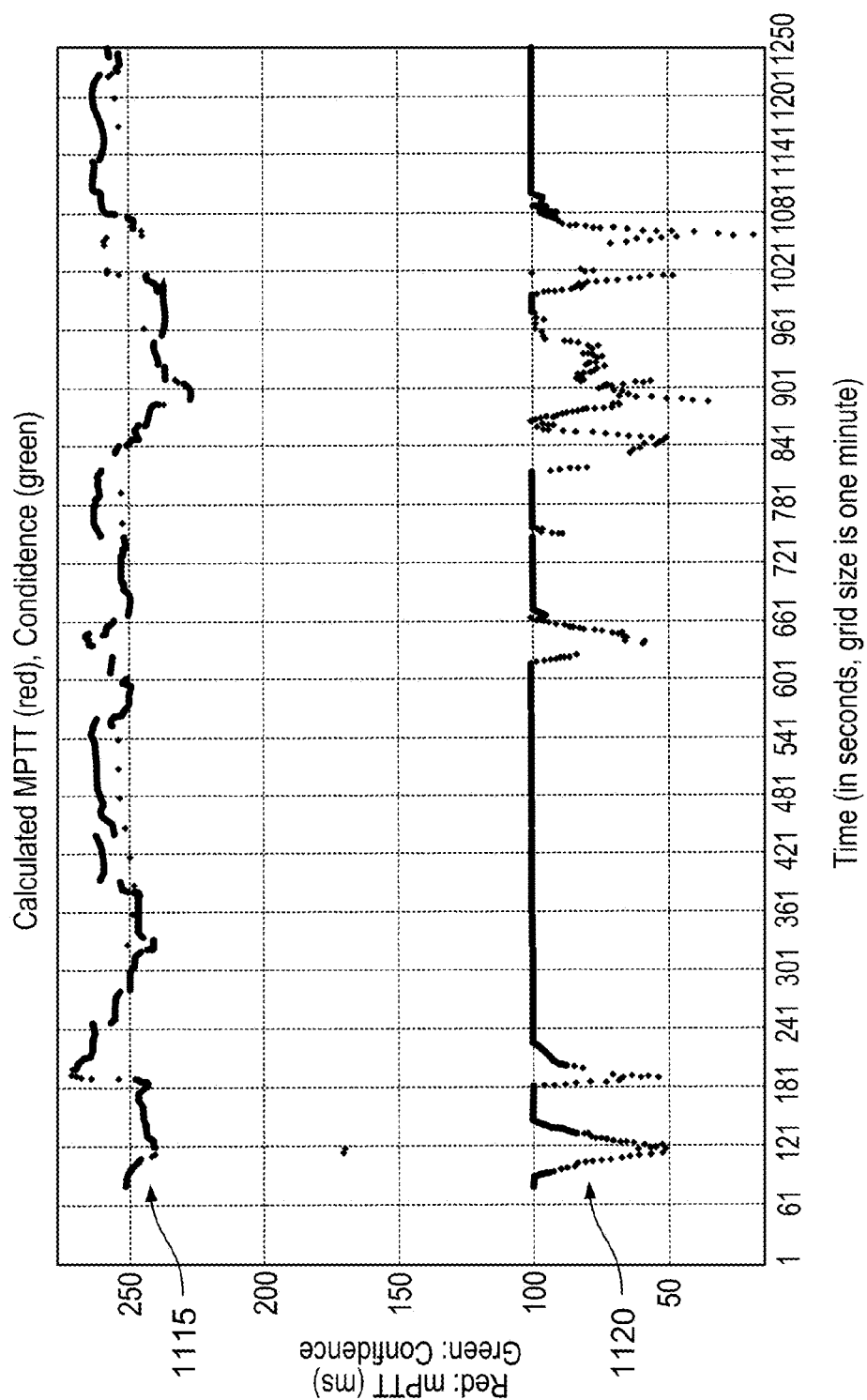

In some implementations, only one candidate MPTT value can be selected. For example, the candidate MPTT value having the highest weights and/or an appropriate or expected morphology can be selected. In some implementations, a confidence measure can be determined for each measurement of MPTT (or other biometric parameters) to indicate the confidence one has in the reading. An example is shown in FIG. 11B, which illustrates computation of confidence measures 1120 corresponding to the calculated values of MPTT 1115. The confidence measures can be used, for example, to determine whether a calculated value can be used for subsequent computations.

Figure 7B:
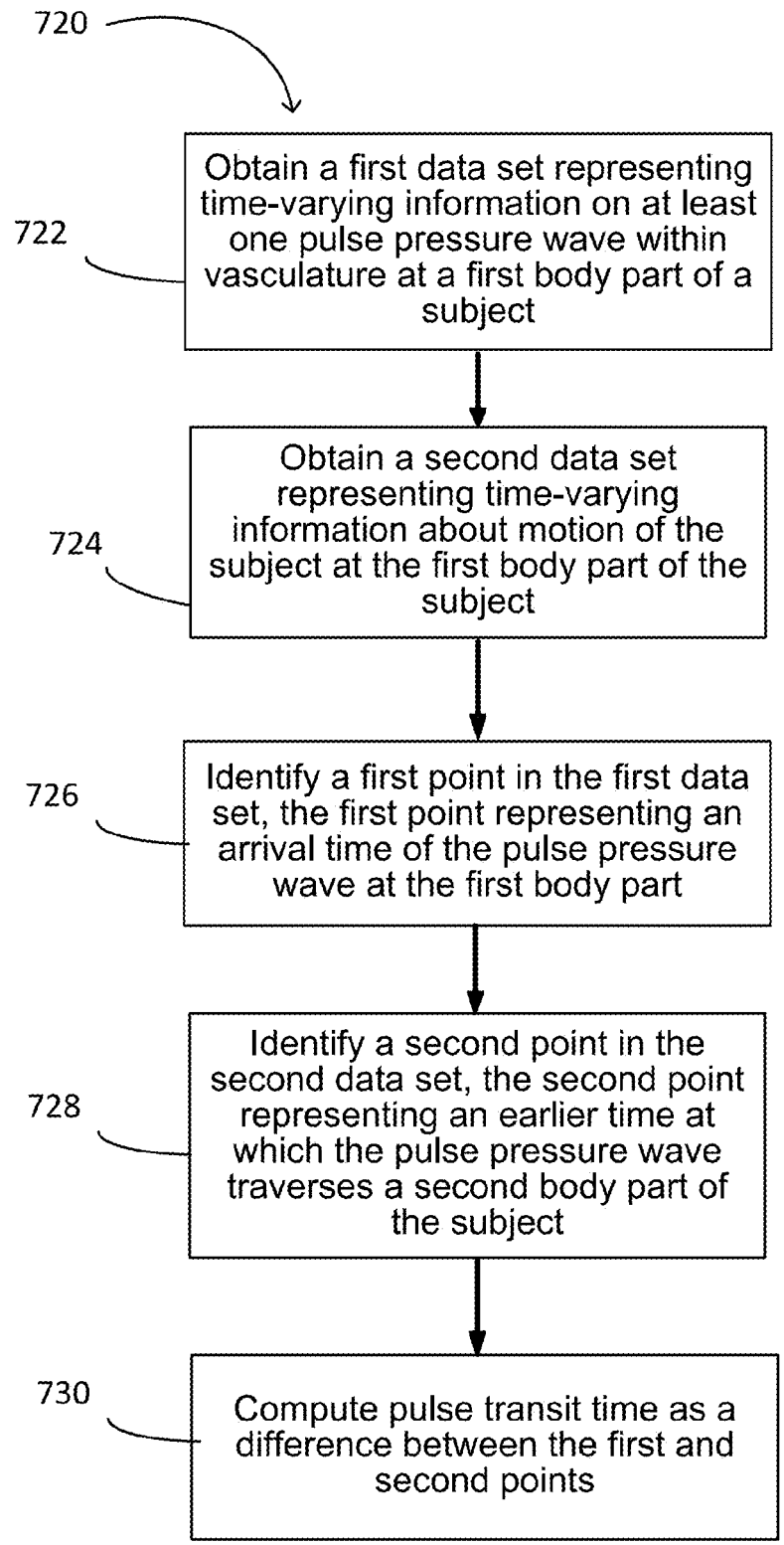
FIG. 7B is a flowchart depicting an example of another process for calculating MPTT.

An example process for calculating MPTT is shown in FIG. 7B. The process can be executed, for example by the device 100 described above with reference to FIG. 1B. Operations of the process can include obtaining a first data set representing time-varying information on at least one pulse pressure wave within vasculature at a first body part of a subject (722). The first data set can be obtained from a first sensor such as a PPG sensor. The operations also include obtaining a second data set representing time-varying information about motion of the subject at the first body part of a subject (724). The second data set can be obtained from a second sensor such as a motion sensor.

The operations further include identifying a first point in the first data set, the first point representing an arrival time of the pulse pressure wave at the first body part (726) and identifying a second point in the second dataset, the second point representing an earlier time at which the pulse pressure wave traverses a second body part of the subject (728). Identifying the first point can include, for example, computing a cross-correlation of a template segment with each of multiple segments of the first dataset, identifying, based on the computed cross-correlations, at least one candidate segment of the first dataset as including the first point, and identifying a first feature within the identified candidate segment as the first point. Identifying the second point can include, for example, determining a reference point in the second data set, wherein the reference point corresponds to substantially the same point in time as the first point in the first data set. One or more target features can then be identified within a predetermined time range relative to the reference point, and a time point corresponding to one of the target features can be selected as the second point.

The operations also include computing MPTT as a difference between the first and second time points (730). The MPTT represents a time taken by the pulse pressure wave to travel from the second body part to the first body part of the subject can then be used in computing various parameters such as blood pressure or arterial stiffness.

Use of the MPTT and SV Values

The calculated MPTT value is related to elasticity of the blood vessels as shown in the following equation:

$$PTT = \frac{L}{PWV} = \frac{L}{\sqrt{\frac{Eh}{2\rho r}}}, \quad (1)$$

where L is the vessel length, PWV is the pulse wave velocity, E is the Young's modulus, h is the vessel wall thickness, ρ is the blood density, and r is the vessel radius.

The elasticity is in turn related to the vessel pressure P as:

$$E = E_o e^{\alpha P}, \quad (2)$$

where $E_0$ is an elasticity parameter, and α is about 0.017 mmHg-1. Based on (1) and (2), the vessel pressure P can be derived as:

$$P = A \ln(PTT) + B, \quad (3)$$

where A and B are parameters calculated as follows:

$$A = -\frac{2}{\alpha}$$

$$B = \frac{1}{\alpha} \ln\left(\frac{2L^2 \rho r}{E_o h}\right)$$

The pressure value calculated using (3) represents diastolic pressure (Dia). The systolic pressure (Sys) can then be computed as:

$$Sys = Dia + C^* SV, \quad (5)$$

where A is a universal constant that applies to all users and is unitless, B is an individual constant in units of mmHg, C is an individual constant in units of mmHg/mg, and SV is the stroke volume.

Calibration

The parameters B and C for calculating the diastolic and systolic pressures may vary from one person to another. Accordingly, a process or device may need to be calibrated for an individual before use. Generally, the calibration is performed the first time the accelerometer and the optical sensor are used for measuring and the algorithms are used for calculating the MPTT, SV, and the other parameters.

Figure 12:
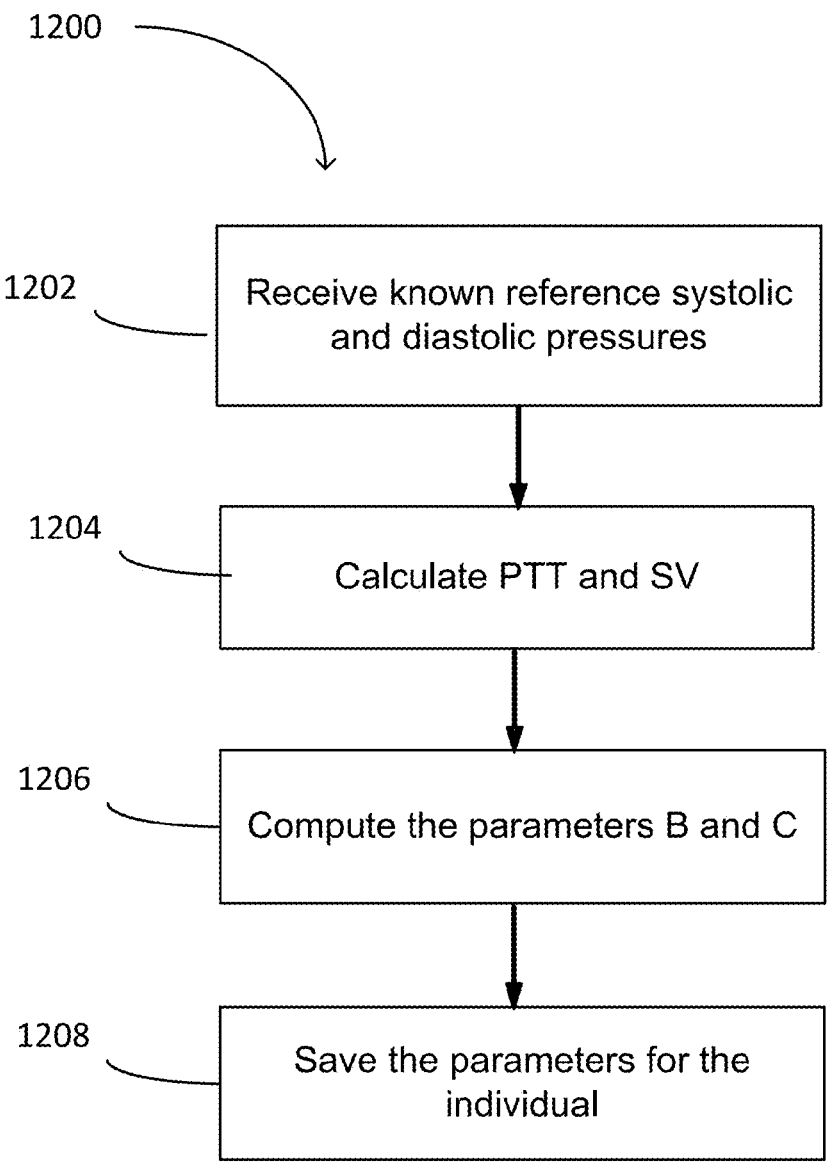
FIG. 12 is a flowchart depicting an example of a process for calibration of the device of FIGS. 1B and 1C.

An example process 1200 of calibration performed by a machine, such as a processor, is shown in FIG. 12. The machine receives (1202) known reference systolic and diastolic pressures (Sys0 and Dia0), e.g., as input from a wearer. If the pressures are unknown to the wearer, generic values of 120/80 mmHg are used. In such cases, the wearer may be allowed to alter the calibration at a later time when the actual pressures becomes known. The machine also calculates (1204) the MPTT and the SV using methods described above. The machine then calculates the constants B and C (1206) for this particular wearer based on the following equations:

$$B = \text{refDia} - A \ln(MPTT), \text{ and}$$

$$C = (\text{refSys} - \text{refDia0})/SV.$$

The values of the parameters are saved or stored (1208) for the individual. In some situations, a device (e.g., the device 100) including the accelerometer and the optical sensor can be used by multiple people. A calibration is performed for each individual following the process 1200 and a set of calculated parameters are stored in association with the corresponding person. The device may automatically choose a set of stored parameters for use with an individual based on biometric identifications of the individual, or may ask the individual to self-identify and choose the correct set of parameters for use, in case the device is shared among multiple users.

After the calibration, blood pressure measurements based on continuously acquired data can be made available for each individual by converting the MPTT and SV into systolic and diastolic pressures as described above.

In some implementations, the systolic and diastolic pressures can also be calculated by adding time-varying parameter estimations based on second order parameters. For example, the diastolic pressure can be calculated as:

$$Dia = B + A^* \ln(MPTT) + D^* f(HR) + E^* g(\text{temperature})$$

where f(.) and g(.) are predetermined functions, and the parameters D and E are time dependent and individual dependent. The parameters can be calibrated when at least two calibration points (e.g., two known sets of systolic and diastolic pressures) at different times are available.

Figure 13:
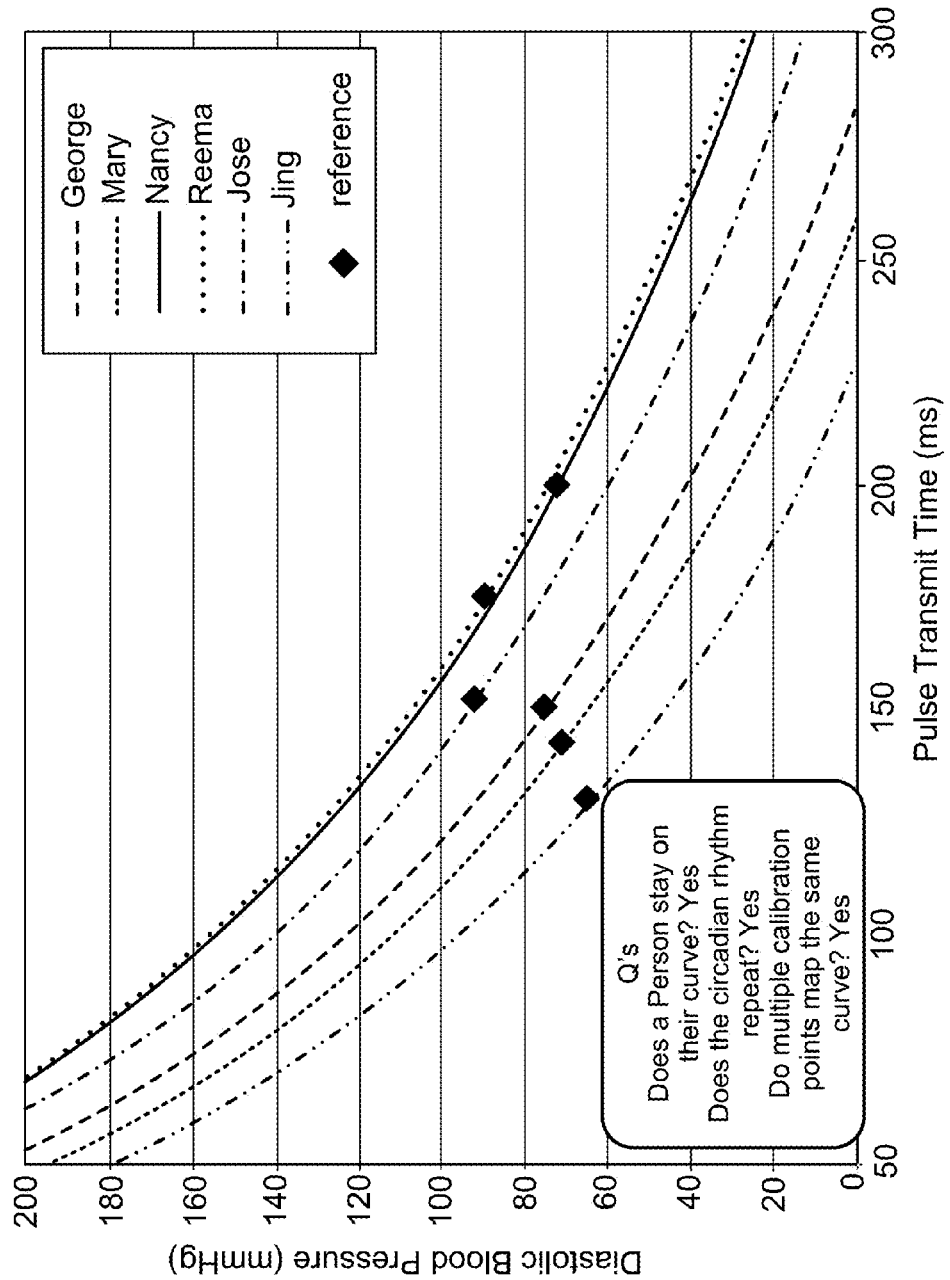
FIGS. 13 and 14 illustrate examples related to calibration of the device of FIGS. 1B and 1C.

Generally, the calibrated parameters do not change frequently. These parameters may be affected by arterial diameters, arterial wall thicknesses, arterial lengths, arterial elasticity, and other physical parameters related to the cardiovascular system of a human body. The majority of the volume of blood related to MPTT travels through large arteries, and is less susceptible to hydrostatic changes, temperature, or peripheral tone. Curves representing relationships between MPTT and blood pressure are illustrated in FIG. 13. As seen from this example, while the curves may differ from one person to another, the general shapes of the curves are similar.

Figure 14:
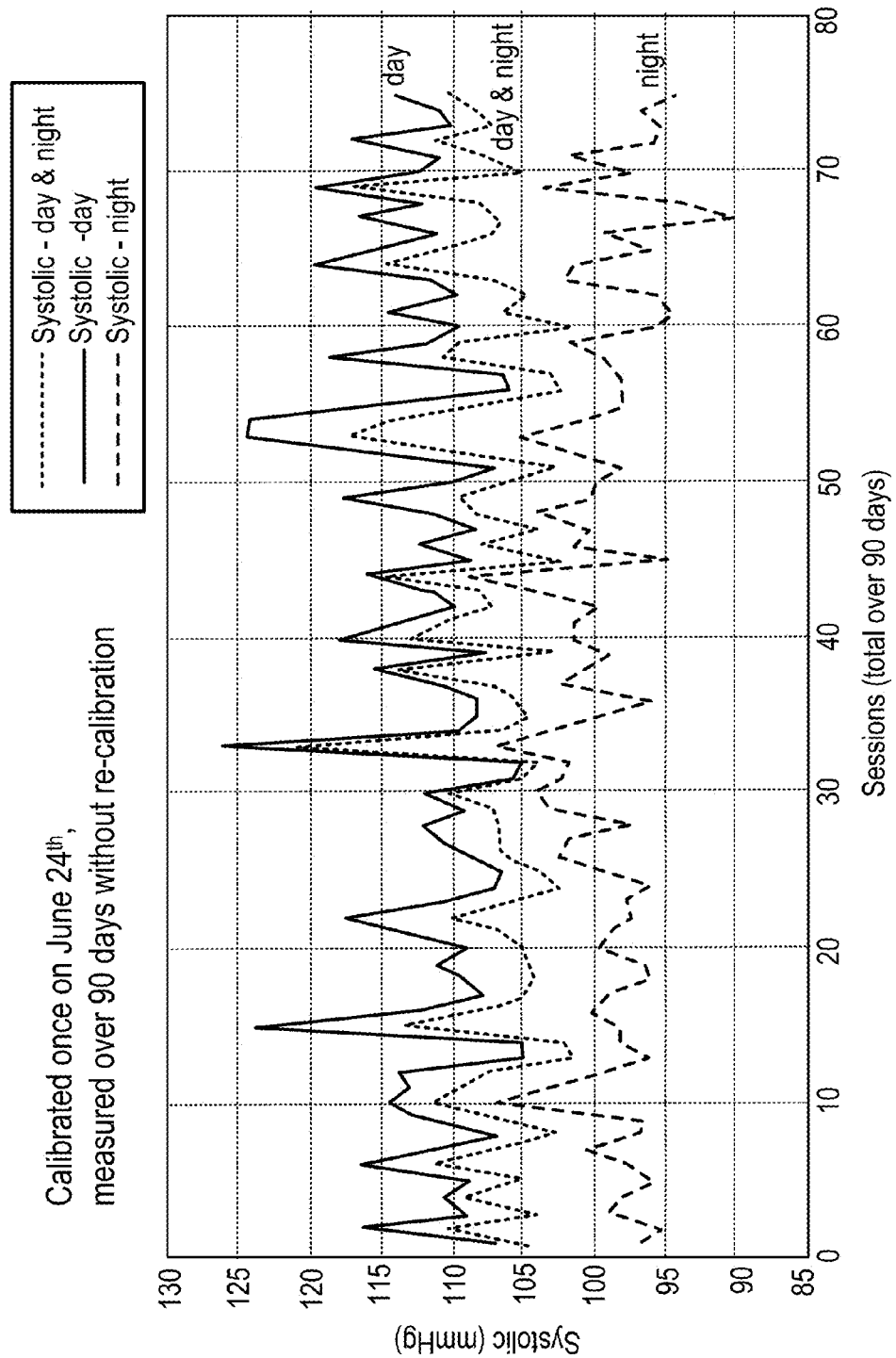

Because multiple calibration points for a given person appear to remain on the corresponding curve, consistent data may be obtained for a reasonably long time after one calibration. With the system being calibrated around the reference 'normal' blood pressure values, if the user's blood pressure deviates from the original calibration values over time, the device will correctly identify that the BP values are different but with reduced accuracy. At that point the device may alert the user that calibration is required. In some cases, the device may not require recalibration for several months. As an example, FIG. 14 illustrates systolic pressure measured over 90 days after a single calibration, and in the absence of any additional recalibration.

In addition to using the PPG data and accelerometer data (e.g., MoCG data) discussed above to determine certain vital signs (e.g., blood pressure (BP), HR, HRV, respiratory rate, blood oxygen levels, SV, and cardiac output (CO)) of the wearer of the device, a processor (e.g., a processor of the computing device 115 (shown in FIG. 1B), or of an external computing device to which the PPG data and the MoCG data is transmitted) can be programmed to use this data to detect or predict certain health-related conditions.

Detection of Irregular Heart Rhythms

The processor can be programmed to use the PPG data and accelerometer data to detect arrhythmia or irregular heart rhythms, such as arterial fibrillation (AFIB) or atrial flutter. FIGS. 15A-15D shows graphs in which heart rate data of the wearer of the device 100 is plotted. The graphs show heart rate data plotted over a 24 hour period (FIG. 15A), during the day (FIG. 15B), and during the night (FIG. 15C). Specifically, each of these graphs includes R wave to R wave interval ($RR_i$) along the x-axis and $RR_{i+1}$ along the y-axis. The plotted data can be used to determine whether the subject has a normal heart rhythm or an irregular heart rhythm, as described below. The plots can be updated after predetermined intervals (e.g., every 5-10 minutes) in order to capture any transient anomaly.

Figure 15A:
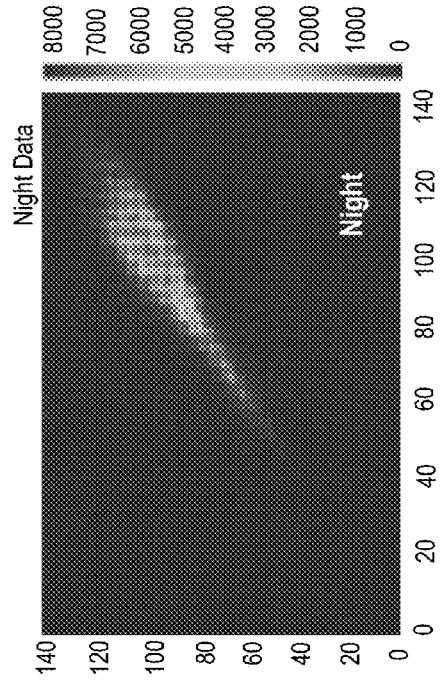
FIGS. 15A-15D and 16A-16C show examples of plots used in detecting various heart conditions.
Figure 15B:
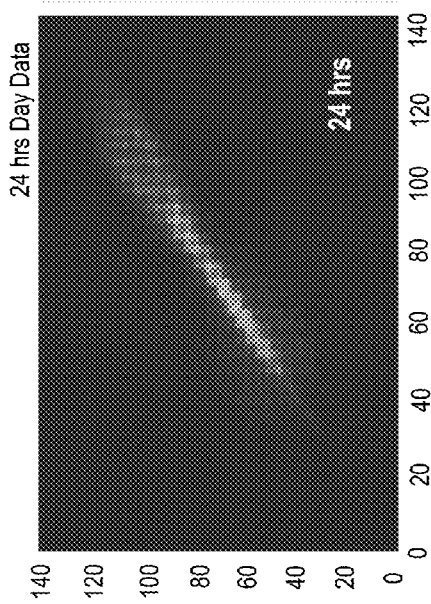
Figure 15C:
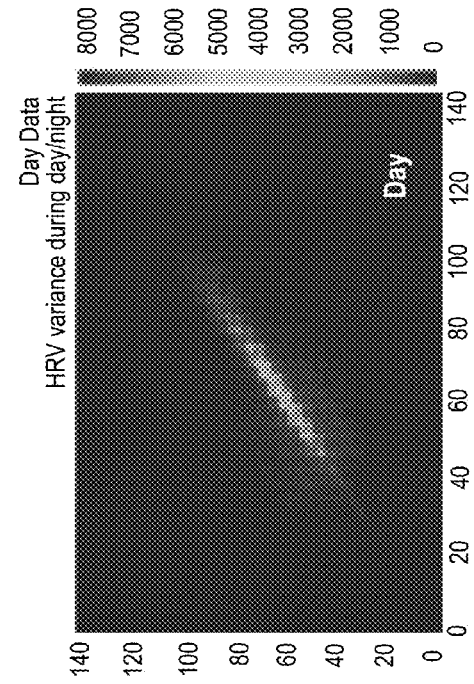

To populate the graphs shown in FIGS. 15A-15C, the PPG and accelerometer signals are used in the manner described above to determine the instantaneous heart rate of the wearer for each heartbeat of the wearer over a period of time (e.g., 20 seconds). The RR values are then determined by examining the instantaneous heart rate curve to determine the time between each of the successive heartbeats. Each RR value is equal to the time between two consecutive heartbeats. Each RR value (RR) is then plotted versus the subsequent RR value ($RR_{i+1}$).

Figure 15D:
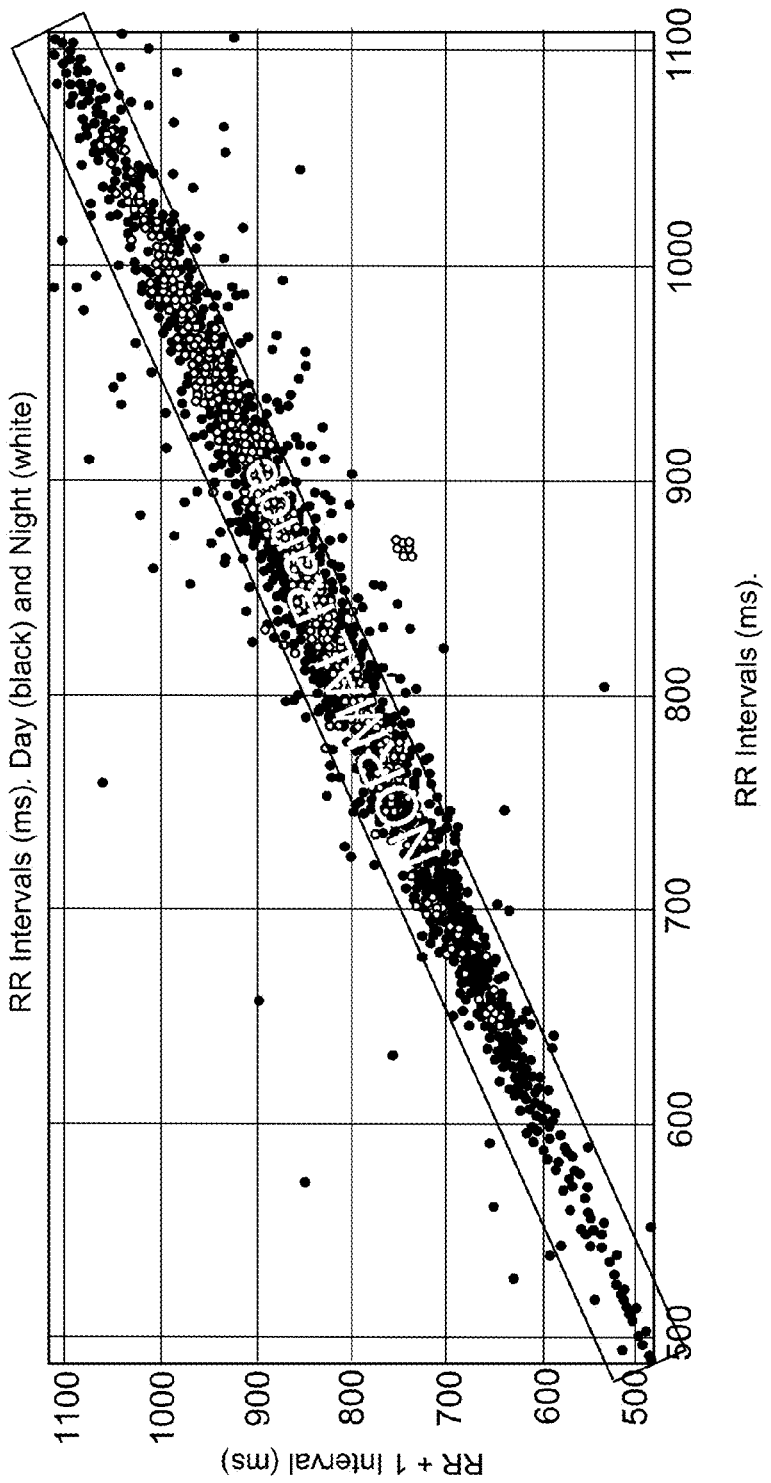

The graphs shown in FIGS. 15A-15D represent plots of a subject with a normal heart rhythm. With a normal heart rhythm, the time between beats tends to be fairly consistent. For example, while a healthy individual's heart rate increases as a result of certain activities, such as exercise, the heart rate tends to increase gradually over time. Thus, while the individual's heart rate may be significantly higher during such activities (as compared to his or her heart rate at rest), the difference in time between consecutive heartbeats should be fairly consistent over the course of a small number of consecutive heart beats. Similarly, while a healthy individual's heart rate may decrease significantly as he or she recovers from such activities, the heart rate tends to decrease gradually over time meaning that the difference in time between consecutive heartbeats should be fairly consistent during such a recovery period. Thus, in a healthy individual, the $RR_i$ vs. $RR_{i+1}$ plot will typically be fairly linear along a diagonal, as shown in FIG. 15D.

Figures 16A, 16B, 16C:
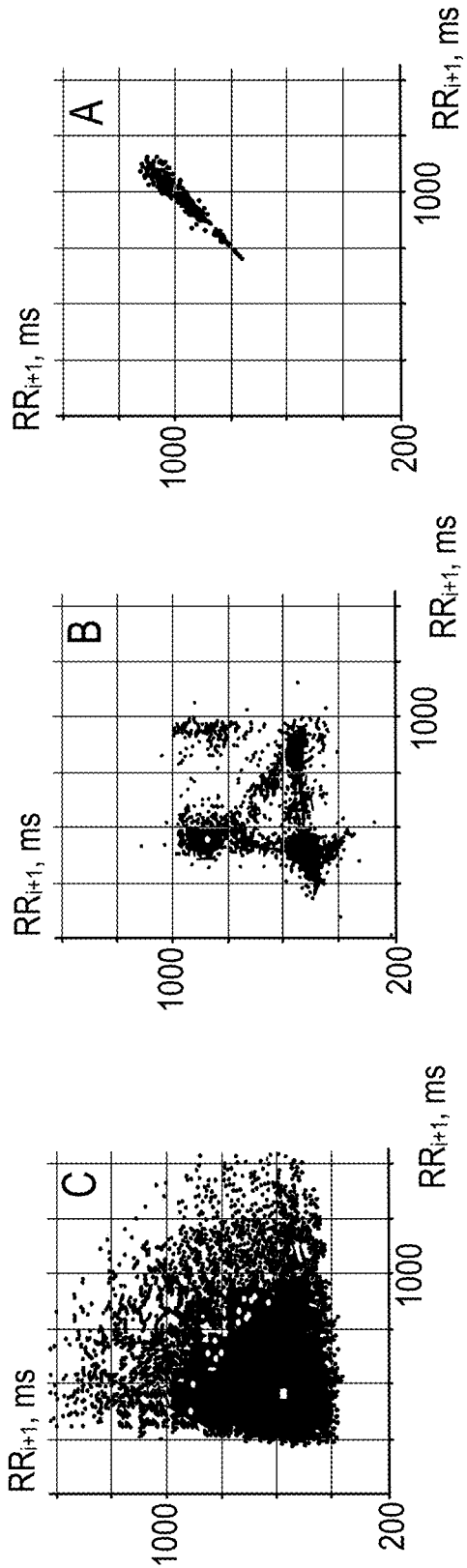

FIGS. 16A-16C show heart rate data for individuals with different heart conditions. For example, FIG. 16A shows heart rate data taken over a 24 hour period from an individual having atrial fibrillation (AFIB). FIG. 16B shows heart rate data taken over a 24 hour period from an individual having atrial flutter, and FIG. 16C shows heart rate data taken over a 24 hour period from an individual having a normal heart rhythm. Referring first to FIG. 16A, AFIB is apparent since the spread of the various RR data points from the expected diagonal is greater than a predetermined spread value. AFIB causes erratic beating of the heart resulting in the time between consecutive heartbeats varying significantly from one pair of heartbeats to the next. It is this characteristic that causes the plot of $RR_i$ vs. $RR_{i+1}$ to spread significantly from the expected diagonal (i.e., the diagonal plot of an individual who has a regular heart rhythm (as shown in FIG. 16C)).

Referring now to FIG. 16B, atrial flutter can be seen by the multiple clusters of data that are offset from the diagonal. Atrial flutter results in changes in heart rate in multiples, which produces the multiple clusters of data that are offset from the diagonal.

In addition to being programmed to detect irregular heart rhythms, such as arterial fibrillation (AFIB) or atrial flutter, the processor can be programmed to alert the wearer in response to detecting such irregular heart rhythms. For example, the processor can activate an audio or visual alarm of the device, which can, for example, instruct the wearer to seek medical attention.

Figure 17:
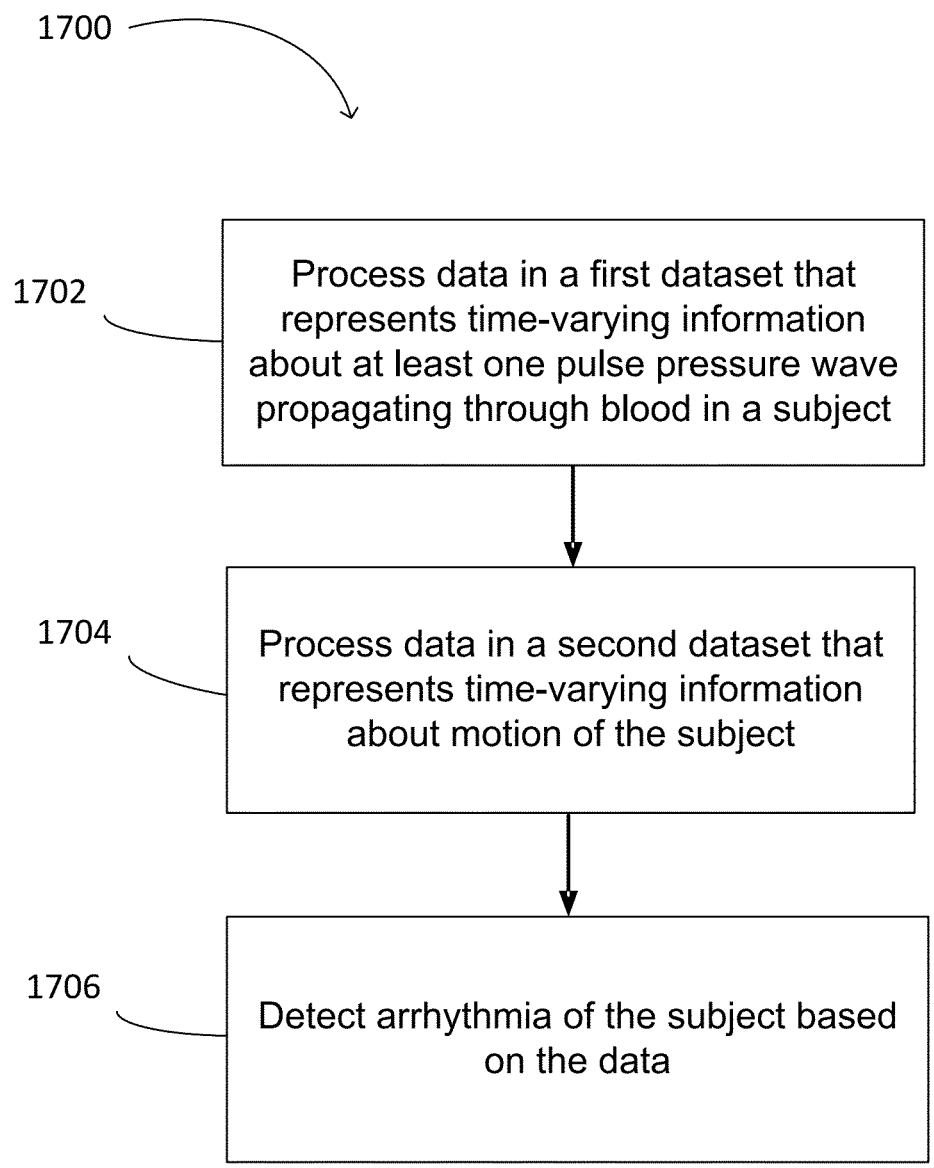
FIG. 17 is a flowchart of an example of a process for detecting arrhythmia.

An example process 1700 of detecting arrhythmia of a subject is shown in FIG. 17. A machine, such as a processor, that receives information from the motion sensor 105 and the optical sensors 110 of the device 100 can perform one or more steps of the process 1700. In some implementations, the machine can include the computing device 115 described above with reference to FIG. 1B. In the process 1700, initially, data in a first dataset that represents time-varying information about at least one pulse pressure wave propagating through blood in a subject can be processed (1702). Data in a second dataset that represents time-varying information about motion of the subject can also be processed (1704). The data can be acquired at a location of the subject (e.g., the arm or the wrist of the subject). Arrhythmia of the subject can be detected based on the processed data (1706). Arrhythmia can include atrial fibrillation or atrial flutter. Processing the data can include determining whether a spread of plotted R wave to R wave intervals versus next consecutive R wave to R wave intervals exceeds a predetermined spread value. Processing the data can also include determining whether multiple clusters of plotted data points are offset from a diagonal Detection of Arterial Stiffness Another health-related characteristic that can be detected by the device described herein is arterial stiffness, which is an indicator for vascular health (e.g. arteriosclerosis), risk for hypertension, stroke, and heart attack. The stiffer the arteries, the faster the blood wave travels (due to fluid dynamics) and thus the shorter the MPTT. The processor can therefore be programmed to calculate arterial stiffness as a function of the pulse transit time (MPTT).

Certain conventional devices that are used to assess arterial stiffness require devices to be placed at two different locations of the subject (e.g., at the carotid and leg of the subject). Thus, the device described herein, which is able to collect from a single location of the subject all necessary data for determining arterial stiffness, tends to be more convenient than those conventional devices.

The processor can be programmed to inform the wearer of the device of his or her arterial stiffness value by, for example, causing that value to be displayed on the display of the device. In addition, the arterial stiffness value can be used as one of multiple factors for assessing the overall health of the wearer. In some cases, for example, the processor is programmed to use arterial stiffness of the wearer to determine a health metric (e.g., a health score) for the wearer. The health score may be a numerical value. In some cases, the numerical value is between 1 and 10 or between 1 and 100.

Figure 18:
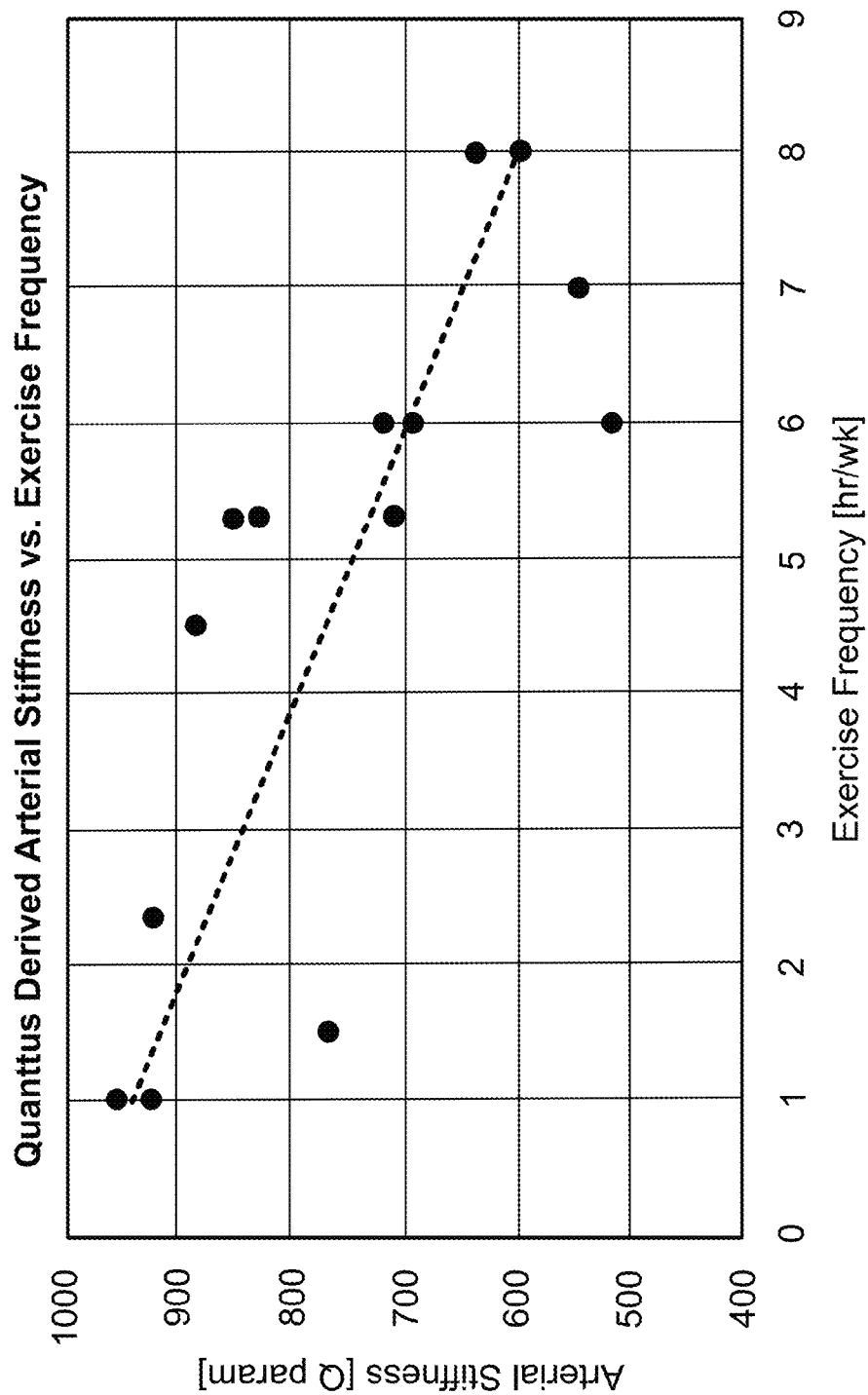
FIG. 18 is an example of a plot of arterial stiffness vs. exercise frequency.

As shown in FIG. 18, the arterial stiffness of a subject tends to decrease as the activity level of the subject (e.g., the number of times per week that the subject exercises) increases. Thus, arterial stiffness is one parameter that can be monitored by the device and shared with the user to track the progress of a subject involved in an exercise regimen. This can serve as positive feedback for the user in addition to conventional feedback, such as weight loss.

Detection of Sleep Conditions

Figure 19A:
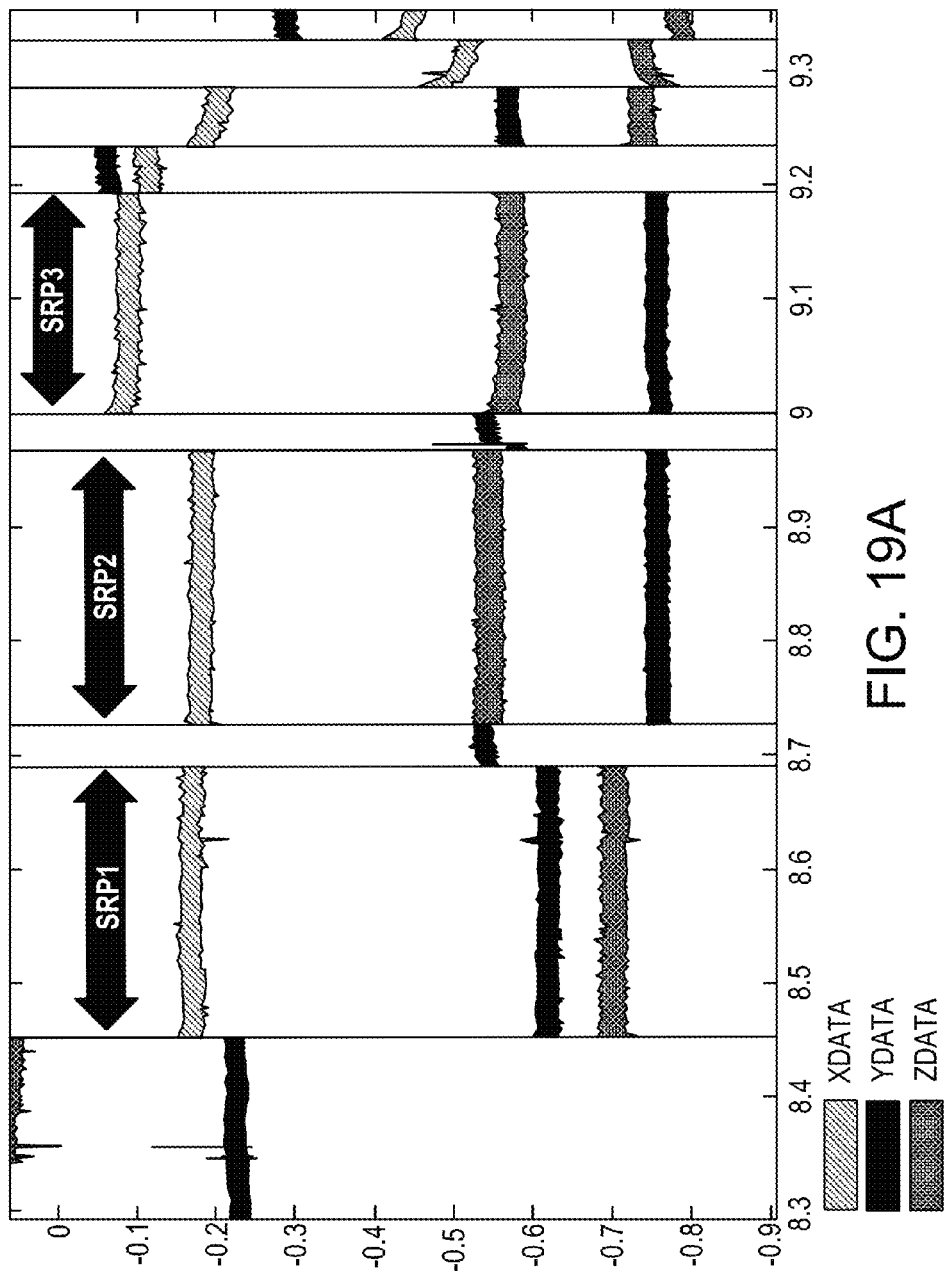
FIGS. 19A and 19B are examples of plots used in determining sleep quality and/or sleep disorders.

The processor can also be programmed to use the PPG data and accelerometer data to detect sleep disorders, such as sleep apnea, and to deduce sleep quality and sleep stages. Referring to FIG. 19, to analyze the sleep of the wearer of the device, the processor first analyzes the low frequency components of the accelerometer data to identify sleep rest periods (SRPs), which are periods in which the accelerometer data is substantially flat for a minimum period of time (e.g., 90 seconds). The flatness of the accelerometer data indicates that the wearer of the device is not moving during the SRPs. Thus, SRPs are periods during which the wearer of the device is likely to be asleep.

FIG. 19 illustrates three separate SRPs (SRP1, SRP2, and SRP3). SRP1 and SRP2 and SRP2 and SRP3 are respectively separated from one another by a brief period of motion by the wearer of the device. However, for purposes of analyzing the heart rate signal for sleep conditions, the three SRPs are treated as a single sleep cycle. The processor can, for example, be programmed to treat periods of motion that last less than five minutes as not interrupting a sleep cycle during which that motion occurs.

After identifying the SRPs, the processor uses the PPG data and the accelerometer data collected during the SRPs to calculate the average heart rate, the standard deviation of the heart rate, the average heart rate variability (HRV), and the average activity level for each of the SRPs. In addition, the processor analyzes the complexity of the heart rate signal and the deviation from diagonal of values plotted on an $RR_i$ vs. $RR_{i+1}$ plot. These parameters can be used to confirm that the wearer of the device was sleeping during the SRP being analyzed and to identify certain sleep conditions and sleep disorders, as discussed below. In some implementations, jet-lag can also be detected by analyzing heart rate during sleep. For example, an upward heart rate during sleep can indicate a presence of jetlag, and a flat heart rate during sleep can indicate that the subject is not jetlagged.

Because lack of motion cannot alone be used to determine whether the wearer of the device was sleeping, the processor can be programmed to consider the average heart rate, the standard deviation of the heart rate, and the average heart rate variability (HRV) to confirm that the wearer was sleeping during the SRP being considered. For example, the average heart rate, the standard deviation of the heart rate, and the average heart rate variability (HRV) of the subject over the SRP being analyzed is compared to the baselines of these values in the subject. If they fall below the baseline by a predetermined amount, this confirms that the subject was asleep during the period being analyzed.

Once the processor has confirmed during which of the identified SRPs the wearer was sleeping, the data collected during those periods can be analyzed to provide detailed information about the wearer's sleep and to deduce the sleep quality. For example, by analyzing the PPG data and the accelerometer data during the relevant time periods, the processor can determine the number of hours slept by the wearer, the sleep latency of the wearer (e.g., the length of time that it took for the subject to transition from wakefulness to sleep), the number of times that the wearer tossed and turned, and the percent of time that the wearer was asleep between the time that he or she went to bed and got up. In some cases, the processor can further determine the deepness of the sleep of the wearer during each of the SRPs. The deepness of the sleep is sometimes referred to as the sleep stage. For example, if the accelerometer detected minimal movement and the patient's heart rate variability was a predetermined amount below the wearer's baseline heart rate during a portion of the SRP, it can be concluded that the wearer was in a deep sleep during that portion of the SRP. If the accelerometer detected some movement and the patient's heart rate was higher than can be expected of a deep sleep during a portion of the SRP, it can be concluded that the wearer was in REM sleep during that portion of the SRP. Otherwise, it can be concluded that the wearer was in a light sleep during that portion of the SRP.

In some cases, the processor is programmed to use the above-noted parameters (e.g., the number of hours slept by the wearer, the number of times that the wearer tossed and turned, the percent of time that the wearer was asleep between the time that he or she went to bed and got up, and the deepness of sleep) to derive a quality of sleep metric or sleep score. The wearer can monitor his or her sleep score over time in an effort to modify his or her sleep habits and maximize the quality of his or her sleep. It has been found that the use of such scores, as opposed to the various different related parameters, are more easily understood by users.

In some cases, the processor can cause the device to automatically display the sleep score when the wearer is determined to have awoken. The device can determine when the wearer has awoken based on information related to the SRPs. Based on characteristics related to the wearer's sleep, information can be provided to the wearer to assist the wearer in improving his or her sleep score. In some implementations, the wearer can be provided with a recommended sleep schedule. For example, if the wearer is determined to have been getting too little sleep, the recommended sleep schedule may suggest that the wearer go to bed earlier in the evening or sleep in later into the morning. The information can be provided on the display of the device or on a separate device, such as a mobile phone of the wearer.

Figure 19B:
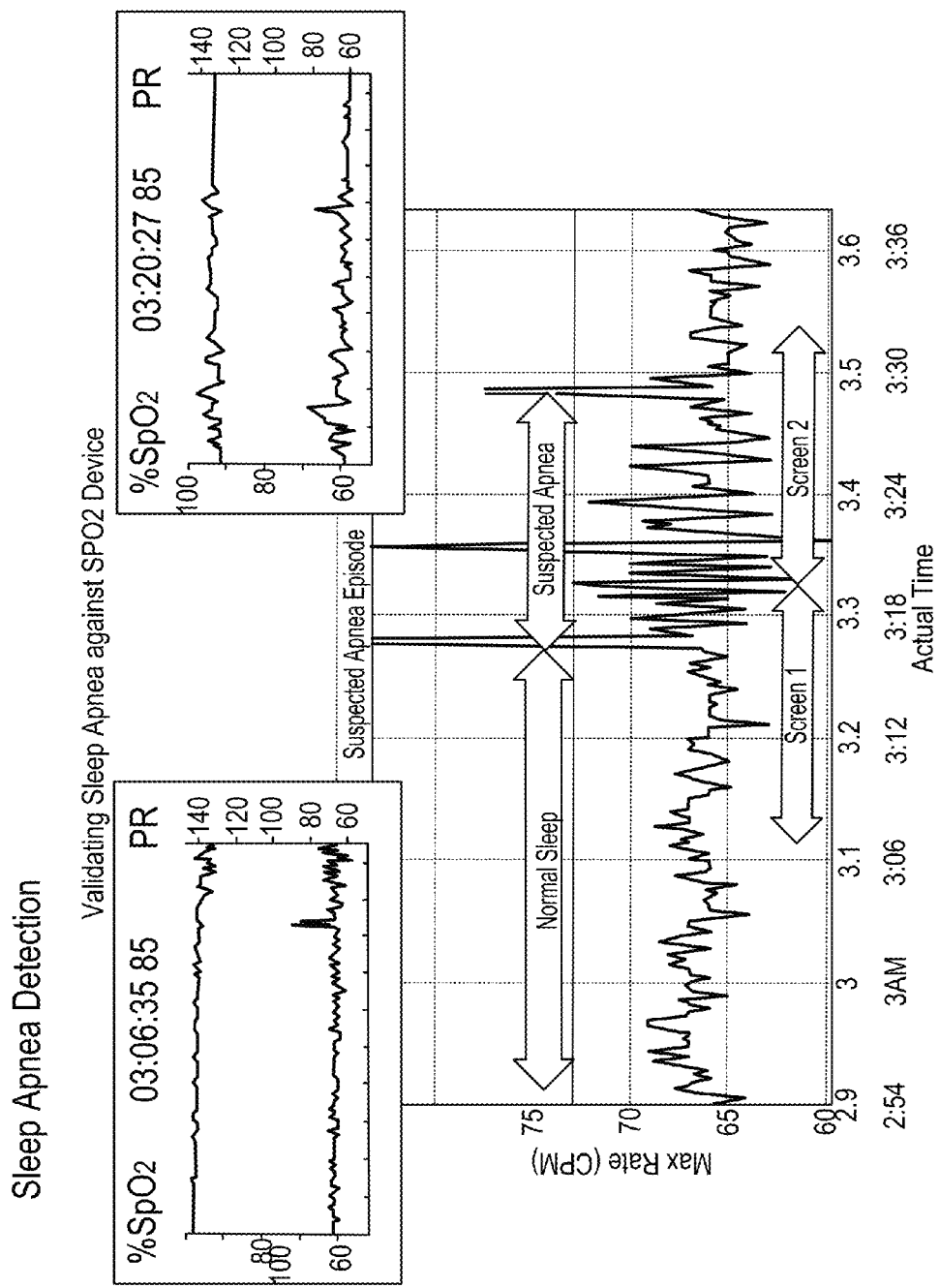

As noted above, in addition to generally determining the quality of the wearer's sleep, the processor can detect certain sleep disorders, such as sleep apnea. FIG. 19B illustrates the heart rate signal of the wearer during a period of time in which the wearer experienced an episode of sleep apnea. Referring to FIG. 19B, the heart rate signal of the wearer is complex from 2:54 AM until about 3:16 AM at which time the heart rate of the wearer spikes suddenly. From 3:16 AM until about 3:30 AM, the heart rate signal is simple (i.e., includes periodicity or a repeating pattern). The presence of a simple heart signal at least every two minutes during an SRP can be indicative of sleep apnea.

The processor can be programmed to carry out a multi-step test to detect sleep apnea. First, the processor analyzes the heart rate throughout the SRP being analyzed. If the difference between the minimum heart rate and the maximum heart rate during the SRP is less than a threshold heart rate differential, then the processor determines that there was no sleep apnea and the test is concluded. If, however, the minimum-maximum heart rate differential exceeds the threshold heart rate differential, then the processor determines that sleep apnea could be the cause and a carries out a further analysis of the SRP. Specifically, the processor analyzes the heart rate variability, the plotted RR points, the complexity of the signal, and the activity level of the subject during the SRP If the heart rate variability is lower during the SRP than in neighboring periods, then this weighs against a finding of sleep apnea. If, however, the heart rate variability during the SRP exceeds the heart rate variability during neighboring periods, then this weighs in favor of a finding of sleep apnea.

Similarly, if the spread of data points in an $RR_i$ vs. $RR_{i+1}$ plot largely lie along the diagonal, this weighs against a finding of sleep apnea. If, however, the data points are spread from the diagonal, then this weighs in favor of a finding of sleep apnea. The data points would be expected to spread from the diagonal during a sleep apnea episode because the wearer's heart rate would drastically increase in a very short period of time due to lack of oxygen in the wearer's blood. This drastic increase in a short period of time would translate to a larger than normal discrepancy between the $RR_i$ and $RR_{i+1}$ values during that time period.

Another factor used to determine whether the wearer has sleep apnea is the complexity of the heart rate signal. If the heart rate signal is complex during the SRP, then this weighs against a finding of sleep apnea. If, however, at least every two minutes, the heart rate signal becomes simple (i.e., has periodicity or a repeating pattern), then this weighs in favor of sleep apnea.

Activity level is another factor used to identify sleep apnea. If the activity level of the wearer during the SRP being analyzed (as determined using the accelerometer data) is greater than the activity level of the wearer during neighboring periods, this weighs against a finding of sleep apnea. If, however, the activity level of the wearer during the SRP being analyzed is less than the activity level of the wearer during neighboring periods, this weighs in favor of a finding of sleep apnea.

The processor can be programmed to determine the presence or absence of sleep apnea as a function of heart rate, heart rate variability, the location of data points on the $RR_i$ vs. $RR_{i+1}$ plot, the complexity of the heart rate signal, and the activity level of the subject.

Figure 20:
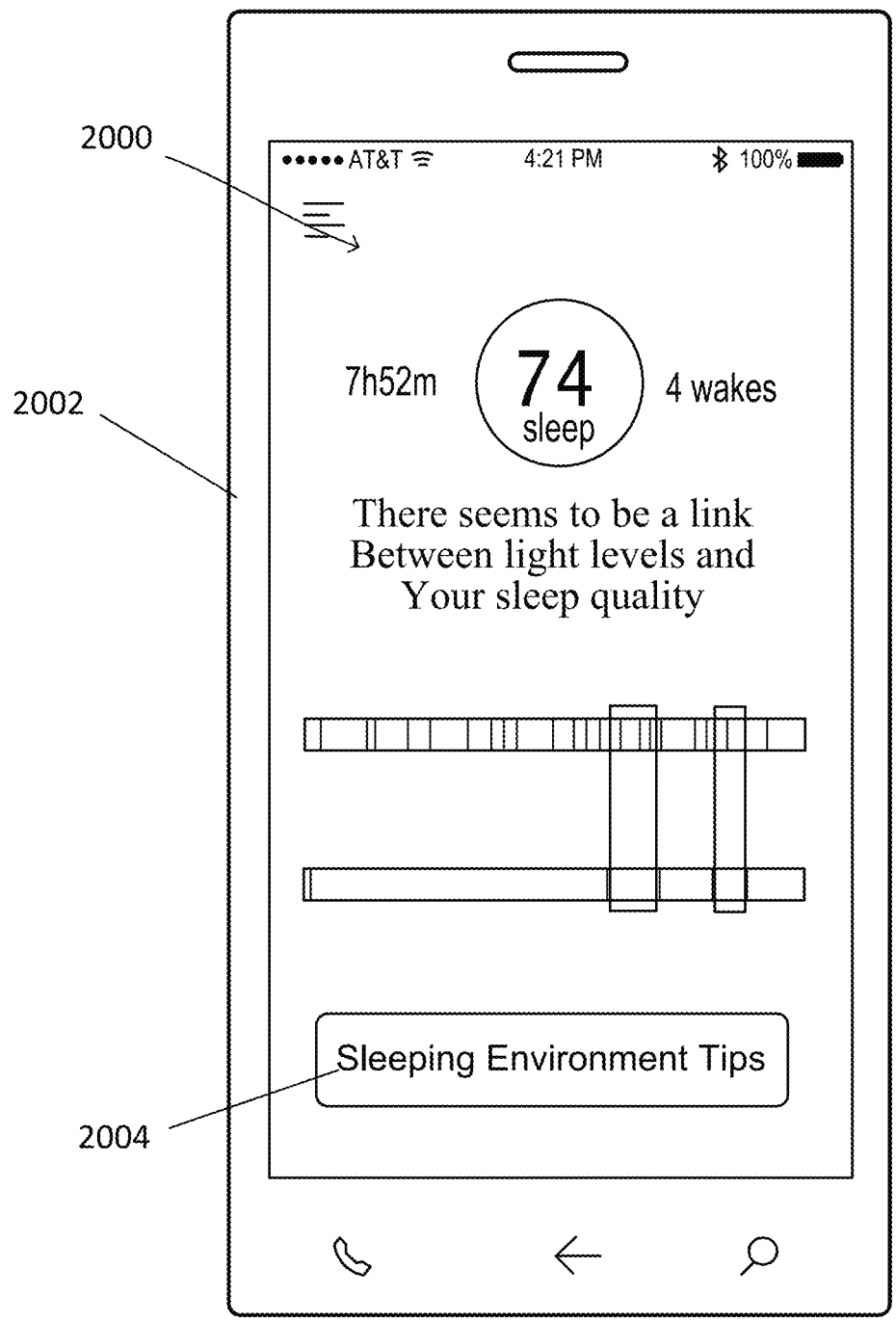
FIG. 20 is an example of a screenshot for showing sleep quality.

In some cases, the processor can be programmed to determine a correlation between the wearer's sleep quality and an amount of light that the wearer is exposed to. FIG. 20 shows an example screenshot 2000 on a mobile phone 2002 of a wearer that displays qualities of the wearer's sleep in conjunction with light levels during various times. In this example, the wearer slept for 7 hours and 52 minutes total, awoke, 4 times, and has a sleep score of 74. The screenshot also includes two bars: one bar shows times when the wearer had low-quality sleep, and another bar shows the measured light levels during those times. In this way, a correlation is made between the wearer's sleep quality and light levels experienced by the wearer. The screenshot 2000 also includes a link 2004 for the wearer to receive sleeping environment tips that can improve his or her sleep quality.

Upon detecting an episode of sleep apnea, the processor can alert the wearer that he or she may have experienced an irregular sleep pattern.

Figure 21:
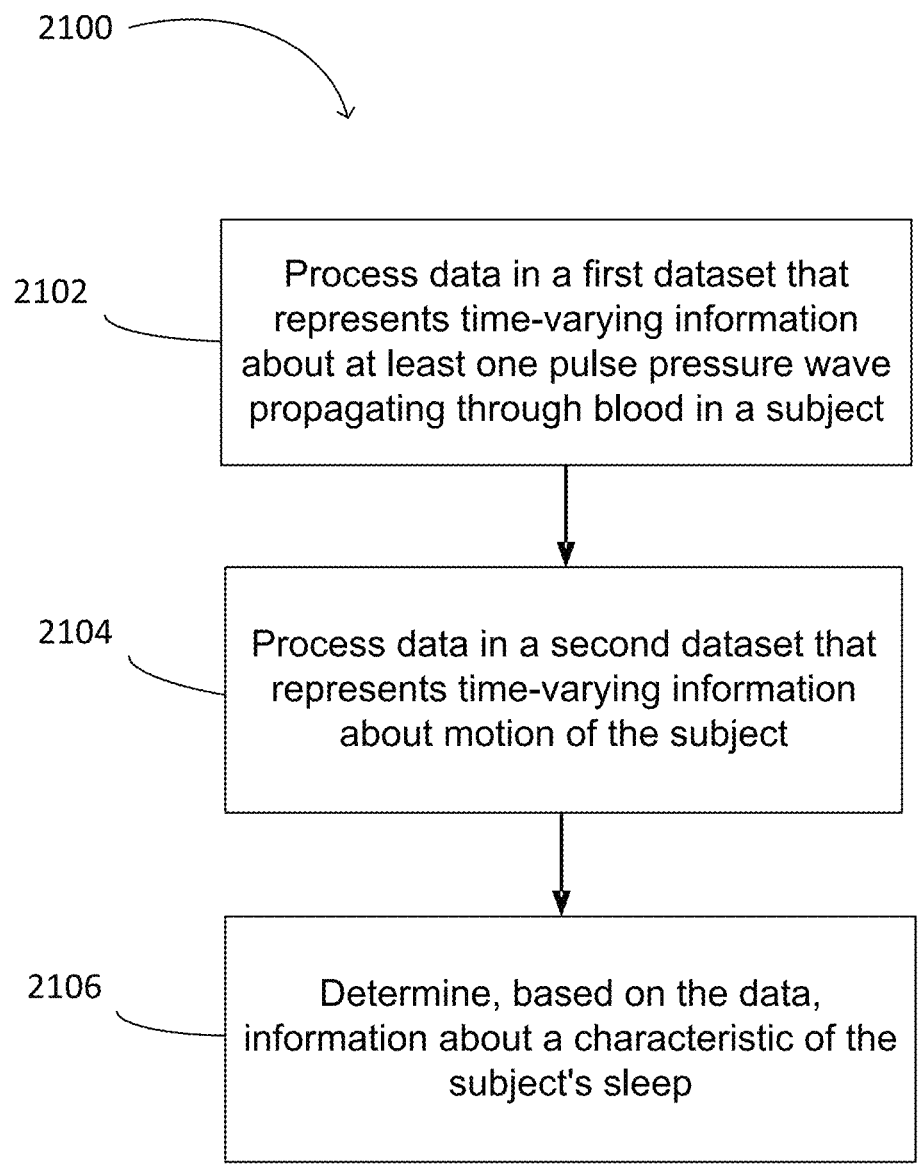
FIG. 21 is a flowchart depicting an example of a process for determining sleep quality.

An example process 2100 of determining information about a characteristic of a subject's sleep is shown in FIG. 21. A machine, such as a processor, that receives information from the motion sensor 105 and the optical sensors 110 of the device 100 can perform one or more steps of the process 2100. In some implementations, the machine can include the computing device 115 described above with reference to FIG. 1B. In the process 2100, initially, data in a first dataset that represents time-varying information about at least one pulse pressure wave propagating through blood in a subject can be processed (2102). Data in a second dataset that represents time-varying information about motion of the subject can also be processed (2104). The data can be acquired at a location of the subject (e.g., the arm or the wrist of the subject). The information about at least one pulse pressure wave propagating through blood in the subject can include photoplethysmographic (PPG) data, and the information about motion of the subject can include one or both of motioncardiogram (MoCG) data and gross motion data. Based on the data, information about a characteristic of the subject's sleep can be determined (2106). The characteristic can include a quality of the sleep of the subject. The quality of the sleep of the subject can include one or more of a sleep duration, a sleep latency, a sleep staging, latency to sleep, a number of disturbances, and a number of tosses and turns. The characteristic of the subject's sleep can also include sleep apnea.

Fitness-Related Applications

The processor can also be programmed to perform various fitness applications that allow the wearer to monitor his or her fitness level. As an example, the processor can be programmed to analyze the accelerometer data over a given period of time (e.g., 15 minutes) to determine the total number of steps taken by the wearer during that time. The processor is programmed to look for rhythm/cadence to detect walking as opposed to other ordinary motion, such as hand motions and vibrations. The absolute value of the accelerometer data will typically be higher during periods of walking that during periods of most other daily activities.

In addition, the processor can calculate calories burned over a given period of time by analyzing the activity level of the wearer and/or the heart rate of the user. Using both the activity level and the heart rate to determine calories burned can lead to a more accurate estimation of caloric output.

In some cases, the processor is programmed to provide a fitness score based on certain fitness-related parameters, such as resting heart rate. The more fit an individual is, the lower his or her baseline HR will be. Thus, in some cases, the processor is programmed to determine a fitness score based on the average heart rate of the wearer during sleep periods or periods of inactivity. Additionally, the speed of heart rate recovery can be a strong indicator of a person's fitness level. For example, the more fit an individual is, the faster his or her heart rate returns to the baseline after exercising. Similarly the more fit an individual is, the longer it takes for his or her heart rate to increase during exercise. Thus, in certain cases, the processor is programmed to determine an individual's fitness score based on the amount of time that it takes for the individual's heart rate to reach a maximum during exercise and the amount of time that it takes for his or her heart rate to return to the baseline after exercise.

In some cases, the processor can cause the device to automatically display the fitness score when the wearer is determined to be in the fitness state. For example, the fitness score may be displayed when the wearer starts to go for a run, and may be displayed throughout the run. In some implementations, the fitness score may be displayed when the wearer transitions from a fitness state to a non-fitness state. For example, the fitness score may be displayed when the wearer finishes a run. In some implementations, the device can determine when the wearer is in the fitness state based on the gross motion data and the vitals of the wearer, such as the wearer's heart rate. Based on characteristics related to the wearer's fitness, information can be provided to the wearer to assist the wearer in improving his or her fitness score.

Figure 22:
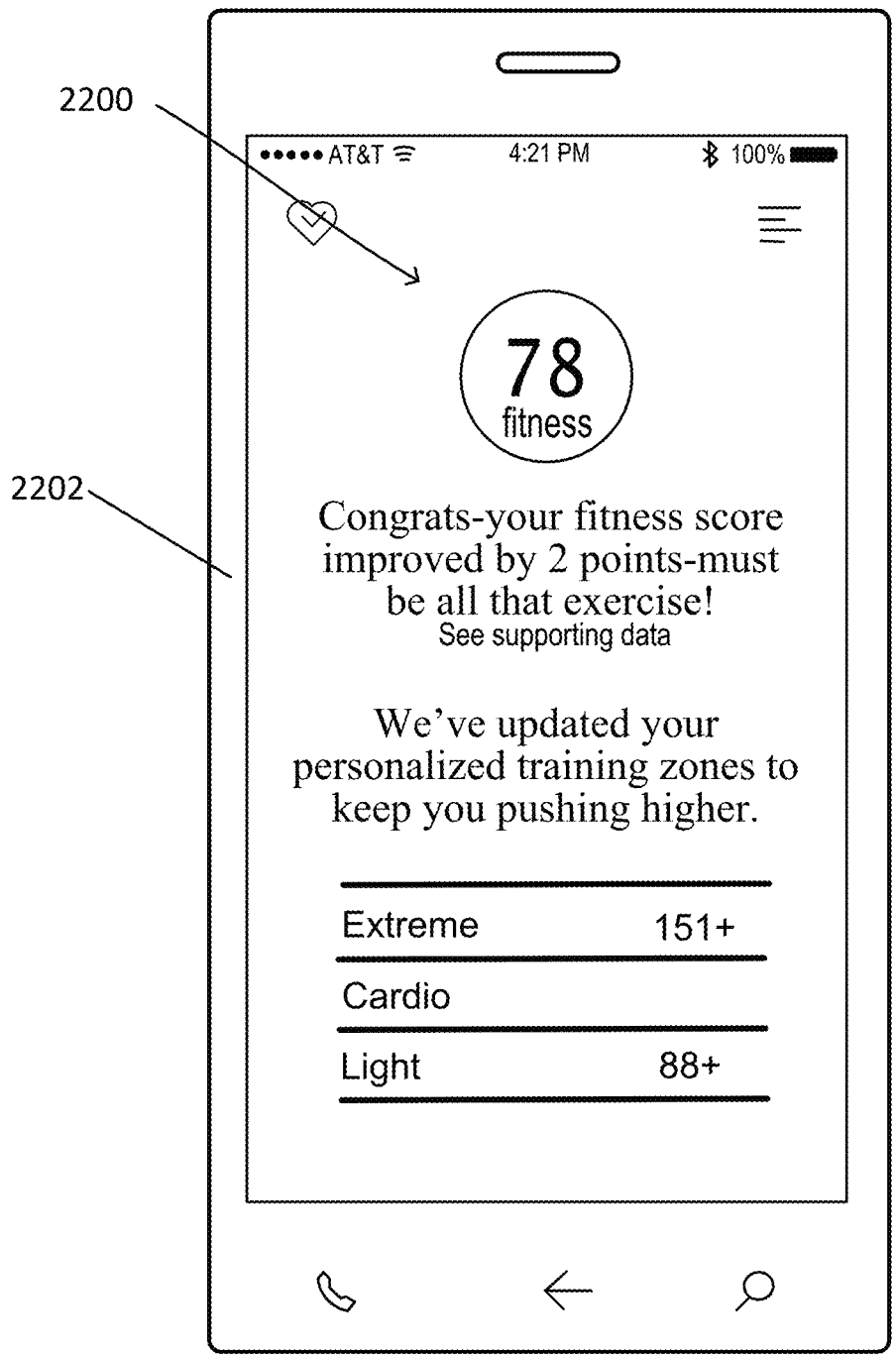
FIG. 22 is an example of a screenshot for showing a fitness-related metric.

FIG. 22 shows an example screenshot 2200 displaying a fitness score on a mobile phone 2202 of a wearer. The information on the screenshot indicates that the wearer has improved his or her fitness score by two points. The screenshot also provides the wearer with updated personalized training zones. The personalized training zones represent the heart rate that the wearer should strive to achieve under various exercise conditions. For example, if the wearer is performing extreme exercise, he or she should strive to have a heart rate of more than 151 beats per minute.

In some implementations, the wearer can be provided with a recommended fitness routine. For example, it may be determined that the wearer has trouble completing a three-mile run, as indicated by an abnormally high heart rate during the run. The recommended fitness schedule may suggest that the wearer run one mile twice a week for a week in order to improve his or her fitness, thereby allowing the wearer to work up to a fitness level appropriate for safely completing a three-mile run. The information for assisting the wearer can be provided on the display of the device or on a separate device, such as a mobile phone of the wearer.

In some implementations, the device may have access to other users' vital information and fitness scores, such that a wearer of the device can compare his or her fitness score to those of other people. For example, a professional athlete who uses the device while training exhibits particular vital information and fitness scores. A wearer of the device may want to follow the same training regimen as the one that the professional athlete follows. However, following the same training regimen does not necessarily produce the same results. For example, a wearer of the device may follow the same training regimen as a professional athlete, but he may not exhibit the same level of effort as the professional athlete. By gaining access to the professional athlete's vital information and comparing it to the wearer's vital information, the device can determine the degree of similarity between the wearer's training level and the professional athlete's training level.

In some implementations, vital information of a professional athlete from when the athlete performed or is performing a particular training routine is presented to the wearer while the wearer performs the same training routine. For example, a video showing the athlete performing the training routine can include a visual indication of the athlete's BP, HR, and respiratory rate over the course of the training routine. As the wearer performs the same training routine while watching the video, the wearer can determine whether he or she is experiencing a similar BP, HR, and respiratory rate as the athlete, thereby indicating whether the wearer is training with the same intensity as the athlete. The video may be configured to interact with the device such that the video encourages the wearer to try harder if the wearer's intensity is below that of the athlete. Similarly, after training, the device can continue to monitor the BP, HR, and respiratory rate of the wearer to determine whether the wearer is physically recovering as well as the athlete.

The vital information of the professional athlete can be used to determine the athlete's physical state at particular times during competition. For example, the athlete's vital information can represent how the athlete physically feels while completing the last 20 meters of a 100 meter dash, or while catching a game-winning touchdown as time expires. A wearer may desire to recreate this feeling for himself or herself. In some implementations, the device is configured to assist the wearer in recreating similar competition situations. For example, the athlete's vital information may indicate that a wide receiver had a particular BP, HR, and respiratory rate while catching a game-winning touchdown in a championship game. The particular BP, HR, and respiratory rate may be significantly higher than they typically would be due to the intensity and importance of the game situation. In order to recreate the situation, a wearer cannot simply go to a local football field and catch a pass from a friend because the wearer would not be in the same physical state that the wide receiver was in at the time of the catch. Rather, the user needs to match the wide receiver's BP, HR, and respiratory rate before recreating the catch. The wearer may perform various actions or activities to artificially match the wide receiver's vitals (e.g., running, listening to loud or exciting music, etc.). When the wearer has achieved a physical state that matches the athlete's, the device can alert the wearer. At that point, the wearer can recreate the game situation with improved accuracy.

In some implementations, the wearer can recreate the game situation with the aid of a virtual reality device, such as a stereoscopic device that creates a computer-simulated environment. For example, the stereoscopic device can be used to aid the wearer in artificially matching his or her vitals with the athlete's by presenting to the wearer the same visuals and sounds that the athlete experienced before the game situation. Once the wearer has achieved a matching physical state, the stereoscopic device can also be used to recreate the particular game situation or play. That is, rather than catching a real football from a real person, the stereoscopic device can display visuals that simulate the action of catching the game-winning touchdown.

Concepts similar to those described above can also apply in the context of combat training A person in a real combat situation typically exhibits increases in BP, HR, and respiratory rate due to the danger of the situation. Training for these situations does not involve the same risk of danger. Thus, such training is typically not performed under the same physical conditions. That is, a trainee does not have the same BP, HR, and respiratory rate that he would otherwise have in a real combat situation. In some implementations, a person's vital information can be used to determine the person's physical state at particular times during a real combat situation. For example, a Navy SEAL may exhibit a particular BP, HR, and respiratory rate while performing a raid of a terrorist hideout. A trainee who is wearing the device may perform various actions or activities to artificially match the Navy SEAL's vitals. When the trainee has achieved a physical state that matches the Navy SEAL's, the device can alert the trainee, who can then recreate a training scenario with improved accuracy.

Monitoring Stress Levels

The processor can also be programmed to analyze the PPG data and the accelerometer data in a way to determine the stress level of the wearer of the device. Heart rate (HR), heart rate variability (HRV), blood pressure (BP), and respiratory rate are all indicators of stress. Specifically, the values of these parameters increase as stress levels increase. Thus, by comparing these values to baseline values of the wearer for associated parameters, the level of stress of the wearer can be estimated. The stress level can, for example, be provided to the wearer as a stress score.

In some cases, the processor can cause the device to automatically display the stress score when the wearer is determined to be in a stress state. The device can determine when the wearer is in a stress state based on the vitals of the wearer, such as the wearer's heart rate, heart rate variability, blood pressure, and respiratory rate. Based on characteristics related to the wearer's stress, information can be provided to the wearer to assist the wearer in improving his or her stress score. In some implementations, the wearer can be provided with a recommended stress-reducing routine. For example, the recommended stress-reducing routine may suggest that the wearer meditate at particular times (e.g., once a day) or adjust his or her daily schedule to minimize circumstances that are generally attributed to stress (e.g., sitting in traffic, working too much, etc.). The information can be provided on the display of the device or on a separate device, such as a mobile phone of the wearer.

Figure 23:
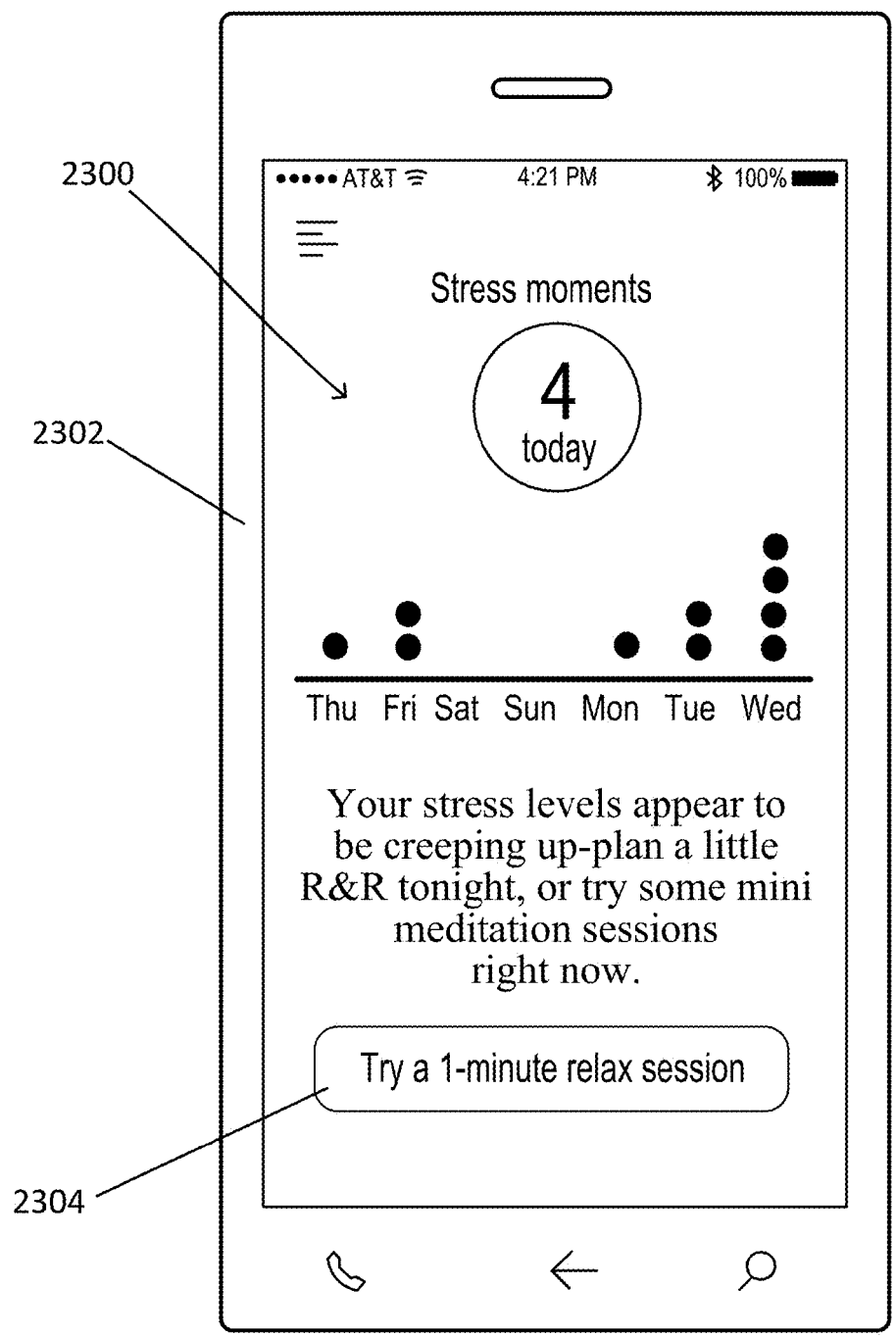
FIG. 23 is an example of a screenshot for showing a stress-related metric.

FIG. 23 shows an example screenshot 2300 on a mobile phone 2302 of a wearer that includes a number of stress moments experienced by the wearer. In this example, the wearer has experienced four stress moments on the current day. A graph indicates the number of stress moments that the wearer has experienced throughout the week. The screenshot includes recommendations for the wearer to reduce his or her stress. In this example, the screenshot recommends that the wearer plan some rest, relaxation, and/or a meditation session to reduce stress. The screenshot also includes a link 2304 to a 1-minute relax sessions, during which the mobile phone guides the wearer on a relaxation session.

Figure 24:
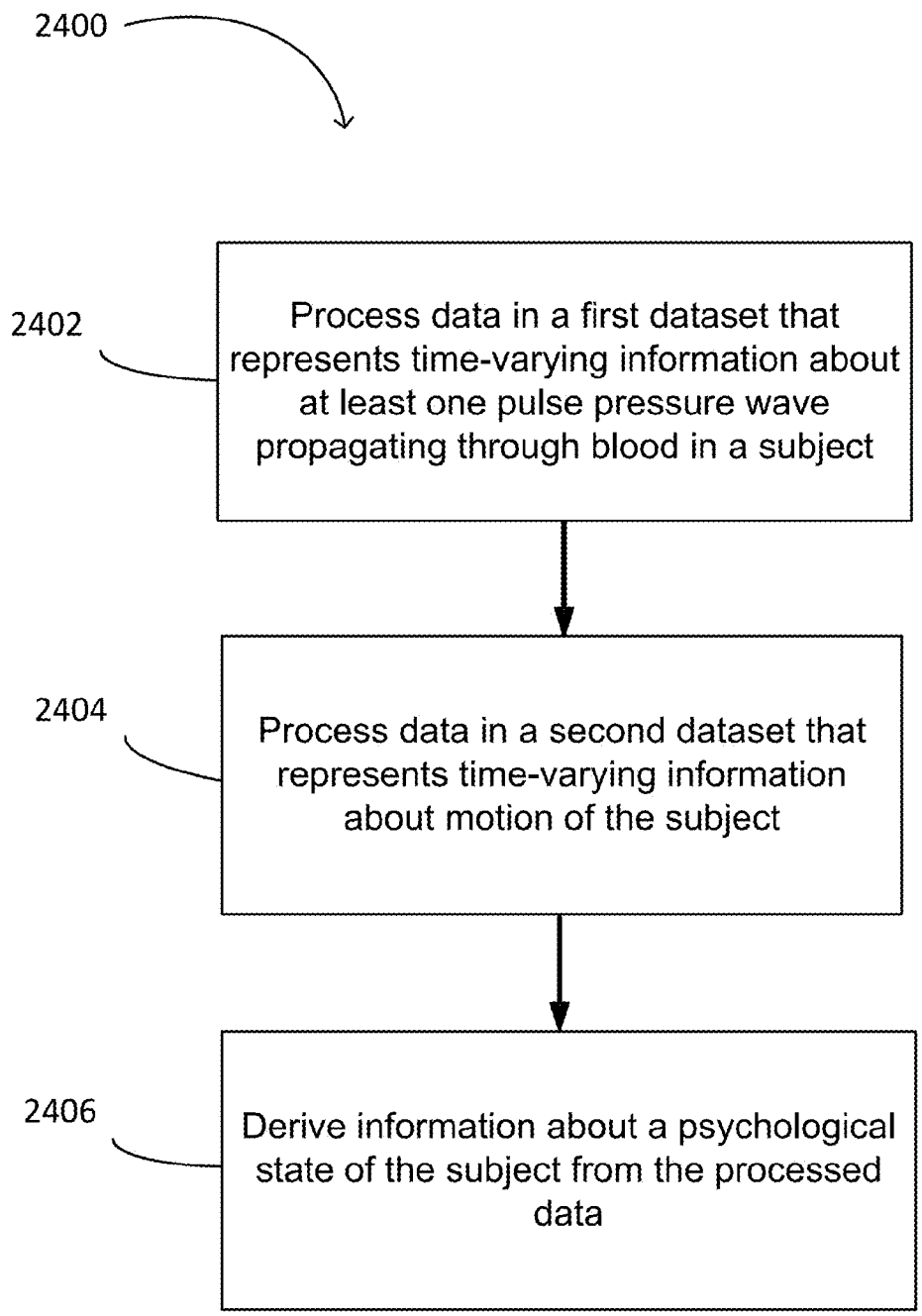
FIG. 24 is a flowchart depicting an example of a process for deriving information about a psychological state of a subject.

An example process 2400 of deriving information about a psychological state of a subject is shown in FIG. 24. A machine, such as a processor, that receives information from the motion sensor 105 and the optical sensors 110 of the device 100 can perform one or more steps of the process 2400. In some implementations, the machine can include the computing device 115 described above with reference to FIG. 1B. In the process 2400, initially, data in a first dataset that represents time-varying information about at least one pulse pressure wave propagating through blood in a subject can be processed (2402). Data in a second dataset that represents time-varying information about motion of the subject can also be processed (2404). The data can be acquired at a location of the subject (e.g., the arm or the wrist of the subject). Information about a psychological state of the subject can be derived from the processed data (2406). The psychological state of the subject can be a state of stress, a malicious intent, or a state of lying. Relationships between at least some of the processed data and a psychological state of the subject can be inferred.

Health Metrics

As described above, one or more scores, also referred to as health metrics, can be derived based on data collected by the device 100. A machine, such as a processor, that receives information from the optical sensors 110 of the device 100 can perform one or more steps of the process. In some implementations, the machine can include the computing device 115 described above with reference to FIG. 1B. Operations of the process can include deriving a score that is associated with a state of a subject. The state of the subject can be one or more of a health state, a sleep metric, a fitness state, and a stress state. Deriving the score can be based on data in a first dataset that represents time-varying information about at least one pulse pressure wave propagating through blood in the subject. The data can be acquired at a location of the subject (e.g., the arm or the wrist of the subject). Deriving the score can also be based on data in a second dataset that represents time-varying information about motion of the subject. The machine can receive information from the motion sensor 105 of the device 100.

Triage Applications

The data produced by the device can be used to assist triage medical personnel in various settings. As an example, the device could be worn by military personnel in battle to provide medical personnel with valuable information regarding the vital signs of the military personnel. The devices worn by the military personnel can, for example, be configured to transmit data regarding their vital signs to a central computer manned by medical personnel. In the event that that multiple casualties are suffered at the same time, the medical personnel can view the vital signs of the various military personnel to prioritize medical care. As a result, the people that most need urgent treatment will receive it first, while those who have less threatening injuries will be attended to later.

In addition to being used for military personnel, the devices described herein could be used to assist medical personnel in various other triage settings, such as sites of natural disasters or terrorist attacks. For example, the medical personnel could be provided with a number of devices that could be put on patients in the triage setting as those patients are being assessed. In this way, after the medical personnel have performed an initial assessment of a victim and determined that he or she does not require urgent medical care, the medical personnel can leave that victim and focus their efforts on victims in more urgent need of medical care. While doing so, the vital signs of those victims who were initially assessed and determined not to require urgent medical care will be monitored and transmitted to a central monitoring station. Thus, in the event that the condition of one of those victims being monitored deteriorates to the point of requiring urgent medical attention, medical personnel in the area can be directed to that victim to provide the necessary medical care.

A machine, such as a processor, that receives information from the optical sensors 110 of the device 100 can perform a process for risk assessment. In some implementations, the machine can include the computing device 115 described above with reference to FIG. 1B. The process can include processing data from a first dataset that represents time-varying information about at least one pulse pressure wave propagating through blood in the subject. The data can be acquired at a location of the subject (e.g., the arm or the wrist of the subject). Data in a second dataset that represents time-varying information about motion of the subject can also be processed. The machine can receive information from the motion sensor 105 of the device 100. The data can be acquired while the subject is in a situation associated with risk. Whether the subject is in a situation associated with risk can be indicated by the data. The risk can be trauma to the subject, and the data can be indicative of the existence of the trauma.

In additional to being used in the triage context, the devices described herein could be used to assist medical personnel in a hospital setting. Once a patient is stabilized following triage, he or she is typically monitored based on a provider's standard of care or mandate (e.g., according to an accountable care organization (ACO)). In some implementations, the device can continue to monitor the vital signs of the patient outside of the triage context to ensure that the care that the patient is receiving is appropriate in view of the patient's vitals. A provider's standard of care may require a patient to go through a progression of steps before the patient is deemed to be ready for discharge. The device can monitor the vital signs of the patient during each step of the progression. For example, the first step of the progression may involve monitoring the patient's vitals while the patient is resting (e.g., lying down and/or sleeping), the second step of the progression may involve monitoring the patient's vitals while the patient is sitting up in bed, the third step of the progression may involve monitoring the patient's vitals while the patient is standing up while being supported, the fourth step of the progression may involve monitoring the patient's vitals while the patient is standing up unassisted, and the fifth step of the progression may involve monitoring the patient's vitals while the patient is walking. The device continuously monitors the patient's vitals throughout each of these stages and can present a notification if the vitals indicate that the patient is in a dangerous state (e.g., if the patient is progressing through each step too quickly without giving his or her body a chance to recover). In this way, the device monitors the patient's compliance with the provider's standard of care.

In some implementations, the patient's vitals can also serve as an indicator of the quality of care that the patient is receiving at a care facility. For example, the device can monitor the vitals of residents at a nursing home to determine the level of activity that the residents are experiencing. Data from the motion sensor of the device may indicate that the residents typically walk or perform other exercises one hour per day, and data from the ultraviolet light sensor of the device may indicate that the residents typically spend two hours per day outdoors. The monitored vitals can be compared to metrics defined by a health organization (e.g., the American Heart Association) to determine whether the residents are adhering to the organization's recommendations regarding physical activity and other health-related actions. The residents' level of compliance with the organization's recommendations can be used to assess the quality of care at the nursing home. In some implementations, the nursing home may be assigned a quality score based on the monitored vitals and the level of compliance with the organization's recommendations, and multiple nursing homes may be compared and/or ranked according to their quality scores. Similar concepts can also apply in the context of child care.

Figure 25:
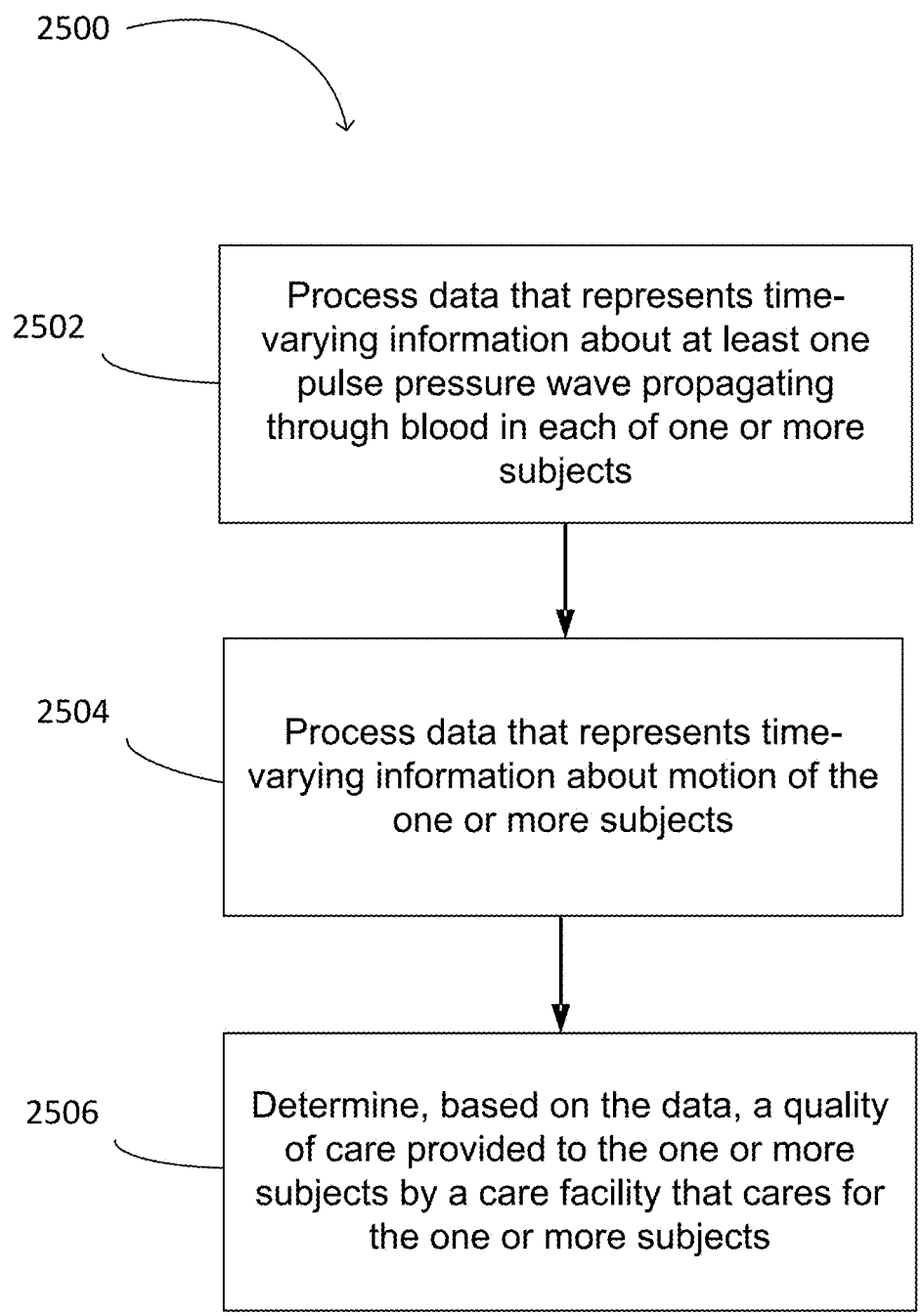
FIG. 25 is a flowchart depicting an example of a process for determining a metric for quality of care provided at a care facility.

An example process 2500 of determining a quality of care provided to the one or more subjects by a care facility is shown in FIG. 25. A machine, such as a processor, that receives information from the motion sensor 105 and the optical sensors 110 of the device 100 can perform one or more steps of the process 2500. In some implementations, the machine can include the computing device 115 described above with reference to FIG. 1B. In the process 2500, initially, data that represents time-varying information about at least one pulse pressure wave propagating through blood in each of one or more subjects can be processed (2502). Data that represents time-varying information about motion of the one or more subjects can also be processed (2504). The data can be acquired at a location of the subject (e.g., the arm or the wrist of the subject). A quality of care provided to the one or more subjects by a care facility that cares for the one or more subjects can be determined (2506). Determining a quality of care can include determining a level of physical activity experienced by each of the one or more subjects. The level of physical activity can be determined by comparing gross motion data gathered by the motion sensor 105 to a threshold. Data that represents information about an amount of ultraviolet light that each of the one or more subjects has been exposed to over a particular time period can also be processed, and an amount of time that each of the one or more subjects has spent outside can be determined.

First Responder Applications

Figure 26:
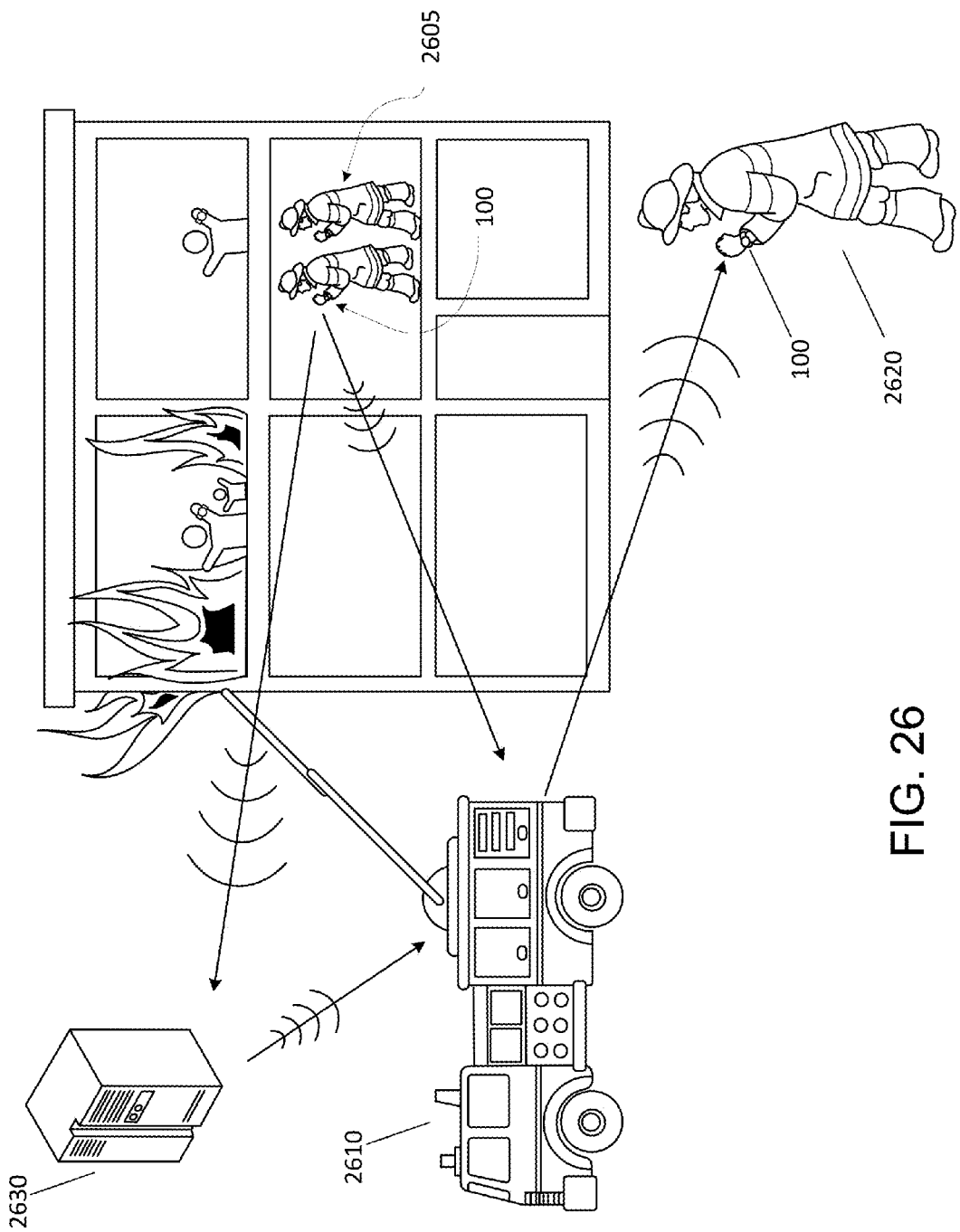
FIG. 26 shows an example where the technology described is used by emergency responders.

The devices described herein can also be beneficial to first responders, such as firefighters and police offers. By wearing the devices, the first responders will ensure that their vital signs are monitored before, during, and after any stressful events that they experience to ensure that they receive the help they need. This is illustrated in the example of FIG. 26, where health parameters of one or more firefighters 2605 on a potentially hazardous mission are obtained via devices 100 worn or carried by the firefighters 2605. In this example, the firefighters' vital signs could be obtained by the devices 100 and transmitted to a central monitoring station (e.g., within a fire truck 2610, or at a fire station) where the vital signs can be monitored to determine whether the firefighters 2605 are well enough to continue fighting a fire or otherwise responding to an emergency. In the event that a firefighter's health is considered to be in jeopardy based on his monitored vital signs, that firefighter could be prevented from continuing to fight the fire or respond to the emergency, for example, by sending an alert to the firefighter 2605 to retreat to a safe location.

In certain implementations, the devices 100 worn or carried by the firefighters 2605 further include GPS transponders. Such devices are particularly beneficial for situations in which one or more first responders 2605 become incapacitated in a dangerous setting. For example, in the event that a firefighter 2605 has a heart attack while fighting a fire inside a building, the device could not only send the firefighter's vital sign data to the central monitoring station to alert someone that the firefighter is in need of medical care, the device could also identify the location of the firefighter 2605 to a rescuer 2620 (possibly via a device 100) sent to assist the incapacitated firefighter 2605, such that the rescuer 2620 knows exactly where to go.

The communications about the health parameters of the one or more firefighters 2605 can be sent directly to the central monitoring station, or via a server 2630. In some implementations, if the server 2630 determines that a firefighter's mental/physical state is not suitable for continuing the mission, the server 2630 can send a signal to the firefighter (e.g., via the device 100, or via another communication device) to alert the firefighter 2605 about the situation. For example, if the health condition of the firefighter deteriorates during the mission (e.g., because of excessive smoke inhalation), a signal can be sent to the device 100 to alert the firefighter to take corrective measures.

In some implementations, the device 100 can be configured to communicate with the central monitoring station on the fire truck 2610. The data from the devices 100 can be transmitted to the server 2630 (possibly via the central monitoring station) for determining whether a firefighter 2605 is safe. The determination can also be made at the central monitoring station. The data from the device 100 may also indicate whether the wearer of the device 100 requires assistance from a rescuer 2620. The server 2630 and/or the central monitoring station can then alert the firefighter 2605 and/or a rescuer 2620 accordingly. In some implementations, if another individual (i.e., someone not in the firefighting team) is wearing a device 100, his/her location may also be tracked using information transmitted from the corresponding device.

Alertness Monitoring

The processor can also be programmed to monitor the alertness of the wearer. This can be particularly advantageous for personnel who perform tasks that require attention and concentration, and could result in serious harm or danger if carried out incorrectly. Examples of such personnel include air traffic controllers, pilots, military truck drivers, tanker drivers, security guards, TSA agents, intelligence analysts, etc.

To monitor the alertness of the wearer, the processor can analyze the respiratory rate, heart rate, blood pressure, and activity level of the wearer. Each of these parameters tends to decrease as a subject falls asleep. Thus, the processor can be programmed to conclude that the wearer's alertness level has dropped to an unacceptable level when one or more of those parameters falls a predetermined amount from the baseline of those parameters.

The processor can be programmed so that, upon determining that the wearer's alert level has dropped to an unacceptable level, an alarm (e.g., an audible, visual, or tactile alarm) on the device is activated. The alarm can raise the alertness level of the wearer and thus reduce risk of harm to the wearer and others.

As noted above, some wearers that may benefit from this application of the device are those wearers that drive vehicles or operate machinery that could present a danger if driven or operated incorrectly. In those cases, the processor can be configured to communicate with the vehicle or machinery for which the wearer is responsible. As an example, the device worn by a truck driver can transmit data regarding his or her alertness level to a controller of the truck. The controller can be configured to disable operation of the truck if the alertness level is below an acceptable threshold. For example, the controller can warn the driver that he or she has a certain period of time to pull the truck over before it is disabled. This will encourage the driver to pull off the road and either get some sleep or otherwise increase his or her alertness level before driving the truck again.

As an alternative to or in addition to taking the actions discussed above in response to detecting a potentially unsafe alertness level, the alertness data can be stored in a database for later analysis. Studying the alertness data from a large sampling of personnel in a given industry can help regulatory bodies for those industries to draft safety standards that increase or maximize safety while maintaining productivity.

Similarly, alertness data over a period of time for a particular wearer of the device can be analyzed to determine the overall physical and/or mental state of a given wearer (e.g., as opposed to the instantaneous state of the given user). Such information can be used to detect a trend of regressing physical and/or mental state of the given wearer. For example, although a wearer of the device may exhibit vitals that indicate that he is alert enough to perform a particular task (e.g., fly a plane) at a particular time, the wearer's alertness data over a period of time may indicate that the wearer's general alertness is on the decline. This may be due to the wearer's old age. The device can detect such a trend and alert the wearer and/or an external entity that the wearer should be closely monitored.

In some implementations, a process can be configured to acquire data while a subject is in a situation that requires a predetermined amount of alertness of the subject. A machine, such as a processor, that receives information from the optical sensors 110 of the device 100 can perform one or more steps of such a process. In some implementations, the machine can include the computing device 115 described above with reference to FIG. 1B. Operations of the process can include processing data in a first dataset that represents time-varying information about at least one pulse pressure wave propagating through blood in the subject. The data can be acquired at a location of the subject (e.g., the arm or the wrist of the subject). The operations can also include processing data in a second dataset that represents time-varying information about motion of the subject. The machine can receive information from the motion sensor 105 of the device 100. The data can be acquired while the subject is in a situation that requires at least a predetermined amount of alertness of the subject. The situation can include one or more of air traffic control, intelligence analysis, vehicle driving, machinery driving, security guarding, baggage screening, and aircraft piloting.

Detection of Malicious Intent

The devices described herein can also be used as polygraph devices. Like conventional polygraph devices, the devices described herein gather a baseline for the wearer's vital signs (e.g., respiratory rate, electrical skin impedance, heart rate, heart rate variability, and blood pressure) and those baselines can later be compared to associated vital signs recorded during questioning. Because the devices described herein are wearable, untethered, and non-cumbersome, and thus do not reduce the mobility of the wearer, the individual being tested can be required to wear the device for a specified period of time (e.g., 24 hours) before and after questioning without hindering the normal, everyday activities of the individual. As a result of the long period of time for which the subject wears the device, the baselines for the subject's vital signs can be more accurately determined. For example, it is less likely that the subject could artificially adjust his or her vital baselines due to the large amounts of data collected to form those baselines. Therefore, the accuracy of the polygraph test can be increased relative to certain conventional polygraph devices.

In addition to monitoring the above-noted vital signs of the subject determine whether the subject is answering questions truthfully, the accelerometer data can be analyzed to identify movements or lack of movements that may indicate that the subject is lying. It is believed, for example, that individuals freeze for a moment when they are caught doing something wrong. In the case of polygraph examinations, it is believed that a subject will freeze when asked a question about the subject's wrongdoing. Thus, by analyzing the accelerometer data of the device, it is possible to identify those times during questioning that the subject freezes. This information can be used to further assess the truthfulness of the subject's response during that time.

Readiness Detection

In addition to those applications discussed above, the processor can be programmed to analyze the PPG data and the accelerometer data to determine the physical and mental readiness of a subject to perform a certain task. General fatigue and stress, which can result in a drop in physical and mental readiness, is generally evidenced by an increase in respiratory rate, heart rate, and blood pressure. Thus, in order to determine a wearer's physical and/or mental readiness, the processor can be programmed to analyze the wearer's respiratory rate, heart rate, and blood pressure and to indicate a state of unreadiness if those parameters fall a certain amount below the baseline for those parameters. In certain cases, the processor is programmed to also consider other factors in this readiness assessment, including the quality of the wearer's sleep (e.g., the wearer's sleep score) over a period of time (e.g., 24 hours or 48 hours) leading up to the assessment.

The determination of readiness of wearers of the device can assist leaders of those wearers with maximizing his or her human resources during taxing situations. For example, military leaders can analyze the data of soldiers in their units to determine which of those soldiers is most physically and mentally able to successfully carry out a mission and can staff the mission accordingly. Similarly, coaches may analyze the data of their team members to determine which of those athletes are best physically and mentally fit to play at their top level at any given time during a competition and can use those players that are able to perform at their top level.

In some implementations, the physical and mental readiness of a subject, as well as motion sensor data and information related to other factors, can be used by the device to predict a winner of a competition. For example, by analyzing vital signs (e.g., BP, HR, respiratory rate) of the contestant before and during a track race, a change in physical and mental readiness can be inferred. The device can also consider information such as the force exerted against the ground by the contestant and the velocity of the contestant at various points during the race to determine a likelihood that the contestant will win the race. The contestant's device can also consider similar information related to other contestants in determining the likelihood that the contestant will win the race. For example, the device may determine that a first contestant got off to a quicker start than a second contestant in a 100 meter dash based on collected motion data. Historical data may indicate that the contestant who is "first out of the blocks" has a 65% chance of winning the race. Thus, the device can predict the winner of the race within milliseconds of the start of the race.

In some implementations, the device can monitor a contestant's performance at an infinite number of intervals while correlating the contestant's performance to the measured vitals. During a one mile track race, a contestant typically keeps track of his lap times for each of the four laps. However, the contestant does not typically have access to more detailed data, such as his or her performance over the first 100 meters, the last 100 meters, at various points in the middle of the race, etc. The device can be configured to keep track of the contestant's performance at any time or range of times during the race, and can also correlate the contestant's performance to the vitals measured by the device. For example, the contestant may complete the first lap of the mile in 50 seconds, putting him or her on pace to easily break the world record. However, the device may determine that the contestant has a BP, HR, and respiratory rate significantly higher than what would typically be seen in someone who has only completed 25% of the race, and thus determine that the contestant likely will not win the race. By exhibiting so much effort early in the race, the contestant burns out and finishes the race with a mediocre time. In some implementations, the contestant can use the performance data and the measured vitals to improve his or her training in the future. For example, the next time the contestant runs a mile, the device may detect that the contestant is exhibiting too much effort early in the race by measuring a high BP, HR, and respiratory rate. The device can be configured to notify the contestant to reserve energy in order to optimize his or her performance.

Similarly, in some implementations, the device can be used to monitor the performance of an entire team of individuals wearing the device. For example, the collective physical and mental readiness of a football team, as well as motion sensor data and information related to other factors, can be used to determine whether the football team is performing to its potential. Information related to the vitals of a first team, such as the team's collective BP, HR, and respiratory rate, may indicate that the first team is exhibiting a large amount of effort. Information related to the vitals of a second team may indicate that the second team is exhibiting minimal effort. However, the second team is winning the football game against the first team, indicating that the first team may have inferior technique or coaching. Such information can be used during training to indicate areas where the team needs to improve their technique. Information related to a team's vitals can also be used to ensure that the team does not exhibit too much effort early in the season, thereby making it susceptible to "burning out" towards the end of the season.

Figure 27:
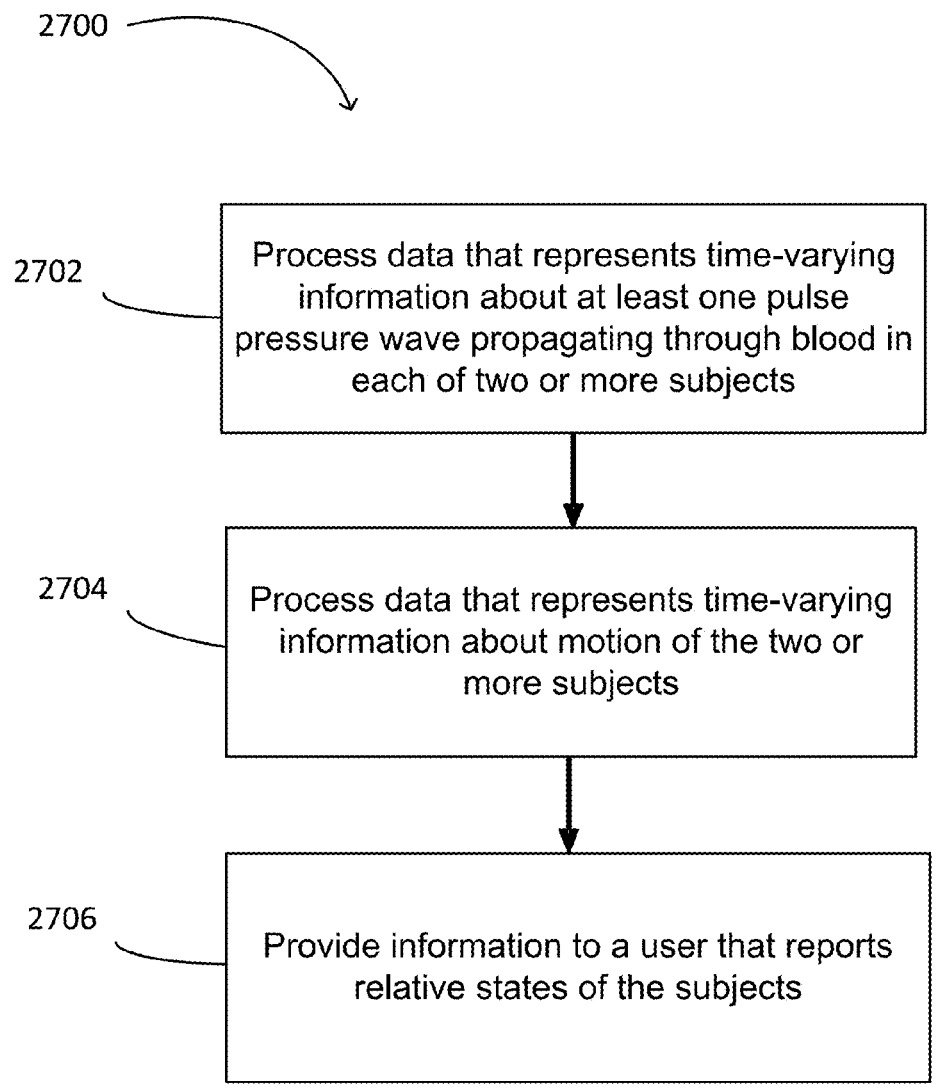
FIG. 27 is a flowchart depicting an example of a process for determining relative states of multiple subjects.

An example process 2700 of providing information to a user that reports relative states of subjects is shown in FIG. 27. A machine, such as a processor, that receives information from the motion sensor 105 and the optical sensors 110 of the device 100 can perform one or more steps of the process 2700. In some implementations, the machine can include the computing device 115 described above with reference to FIG. 1B. In the process 2700, initially, data that represents time-varying information about at least one pulse pressure wave propagating through blood in each of two or more subjects can be processed (2702). Data that represents time-varying information about motion of the two or more subjects can also be processed (2704). The data can be acquired at a location of the subject (e.g., the arm or the wrist of the subject). Information can be provided to a user that reports relative states of the subjects (2706). The information can be based on the processed data. The relative states of the subjects can include one or more of relative psychological states, relative physical states, and relative states of readiness. The subjects can be put into an athletic contest or assigned a particular combat task according to the relative states of the subjects.

Correlation between Impact Force and Vitals of Multiple Users

In some implementations, the processor can be programmed to analyze the vital signs of multiple users in the moments leading up to a collision. For example, when two players collide during a sporting competition, a large amount of force is absorbed by each player. Force data can be measured by the motion sensor of the device, and the device can determine the magnitude of force absorbed by each player. The device can determine the effect of the force on each player by analyzing the players' vitals (e.g., BP, HR, respiratory rate, body temperature) before, during, and after the collision. The vitals and the force information can be used to determine whether a player has sustained bodily damage due to the impact force. For example, if a player experiences a sudden increase in HR, respiratory rate, and body temperature following a collision, it may be an indication that the player has sustained a concussion.

In some cases, a player's bodily reaction to sustaining a concussion is delayed. For example, a player may experience a sudden increase in HR, respiratory rate, and body temperature at some time following a collision, or the player may experience a gradual increase in HR, respiratory rate, and body temperature beginning at the time of the collision. The device can monitor the player's vitals for an extended time following the collision and compare the monitored vital information to vital information of a player who was previously diagnosed with a concussion. In this way, the device can determine vital patterns that are indicative of a person who sustains a concussion. If the device determines that a player has sustained a concussion, the device may be configured to alert the player or a third party. The player may be required to pass a protocol before reentering the game. If the device determines that there is a possibility that the player has sustained a concussion, the device may enter a mode where the player is monitored more closely in order to make a more definitive determination.

Human Flight Recorder

The devices described herein can also be used as human flight recorders. While accident investigators (e.g., National Transportation Safety Board (NTSB) investigators) have traditionally been limited to analyzing voice recorders and, in some cases, black boxes, after airplane and train crashes, the devices described herein, when worn by the operators of those vehicles, will provide insight into the state of the operator at the time of the crash. For example, by analyzing vital signs of the operator (e.g., the respiratory rate, heart rate, heart rate variability, and blood pressure of the operator) in the moments leading up to the crash, the investigators can learn whether the operator fell asleep, experienced some form of medical emergency, etc. This information is valuable for the investigators to determine whether the crash was the result of the operator's actions as opposed to some other reason, such as mechanical failure.

For example, in the context of a car accident, information related to the vital signs of the operator as well as information related to the operating characteristics of the car (e.g., the speed, direction, and breaking, as measured by other sensors) can be used to determine the cause of the accident, the mechanism of injury to the operator, and the impact of the injury to the operator. In this way, the mental and/or physiological state of the operator before, during, and/or after the accident can be ascertained. The 60 minutes following a traumatic injury is generally referred to as the "golden hour," during which there is the highest likelihood that prompt medical treatment will prevent death. It is especially important to quickly gather vital information during this time to assist first responders and doctors in diagnosing and treating the operator.

In some implementations, the human flight recorder information can be used by third parties to determine who was at fault in creating the accident. For example, a law enforcement body may analyze the human flight recorder information to determine whether a tort or a crime was committed by an operator. In some implementations, the human flight recorder information can be used to determine an exact time when an event occurred. For example, the information can be used to determine an exact time of death, an exact time when a person went missing (e.g., by being abducted), or an exact time when a person fell down.

Similarly, after a wearer of the device experiences a period of illness or discomfort, the data could be analyzed by his or her physician to help diagnose the condition. For example, if a wearer has a heart attack, the data could be analyzed to investigate the variation in the vital signs leading up to the attack. Other data can also be considered, such as the wearer's genetics, epigenetics, diet, exercise practice, and environmental circumstances surrounding the event or condition. This information may be correlated and used to prevent onset of similar conditions in the future, for example, by alerting the user of such a possibility upon detecting similar variations in vital signs.

In some implementations, the device is able to determine a "baseline biorhythm" of a wearer based on the wearer's vital signs in various circumstances and environmental environments. The baseline biorhythm is typically unique to each individual. Once the baseline biorhythm is established and substantially refined, the device is able to detect when the wearer's vital signs are shifting away from the baseline biorhythm. For example, the device may detect that a wearer's biorhythm has gradually shifted over a particular time period, as indicated by variations in the wearer's vital signs. The device may also detect that the wearer has spent minimal time outside over the same time period, as indicated by measurements from the device's ultraviolet light sensor. The device can identify a correlation between the wearer's changed biorhythm and the change in ultraviolet light exposure.

In some implementations, the device can identify a correlation between the wearer's changed biorhythm and changes in the weather. For example, the device can consider the wearer's location information in conjunction with weather information from the National Oceanic and Atmospheric Administration to determine the type of weather experienced by the wearer over a particular period of time. The device may identify that the wearer experiences higher BP and HR when the weather is cold and/or rainy and determine that such weather causes increased stress in the wearer.

Detection of Temperature

In addition to using the accelerometer and optical sensor to determine vital signs of the wearer, the device can include a temperature sensor for determining the skin temperature of the wearer and an ambient temperature sensor for detecting the ambient temperature. The processor can be programmed to estimate the wearer's core temperature as a function of the measured skin temperature and ambient temperature (e.g., based on the difference between the skin temperature and the ambient temperature).

Prediction of Medical Events

While certain examples discussed above relate to the use of PPG data and accelerometer data (e.g., MoCG data) to diagnose medical conditions or events that were already experienced by the user, in certain implementations, the processor can be programmed to use this data to predict medical conditions before they happen. For example, the heart rate, heart rate variability, and blood pressure of the wearer can be monitored and processed by the processor to make such predictions. One example of a medical event that can be predicted in a subject is tachycardia. Tachycardia is when a subject's heart rate is over 100 beats per minute. If a subject's heart rate is trending upwards, a prediction can be made as to when the subject will experience tachycardia. Other examples of medical events that can be predicted are hypertension and stroke. For example, if a subject's blood pressure is increasing over time (e.g., if the rate of change of the blood pressure is above a threshold), a prediction can be made as to when the subject will experience hypertension. Hypertension is diagnosed when a subject's blood pressure exceeds 140/90 mmHg. If the increase is rapid, a prediction can be made as to when the subject will have a high likelihood of experiencing a stroke. Similarly, if a subject's blood pressure is decreasing rapidly (e.g., if the rate of change of the blood pressure is negative and below a threshold), a prediction can be made as to whether the subject will have a heart condition.

In cases where the heart rate variability of the subject is used to predict a medical event, whether the subject experiences arrhythmia (e.g., atrial fibrillation) can determine what an appropriate heart rate variability of the subject is. For example, a subject who experiences arrhythmia may have a high heart rate variability, but this may be normal given the subject's condition.

Figure 28:
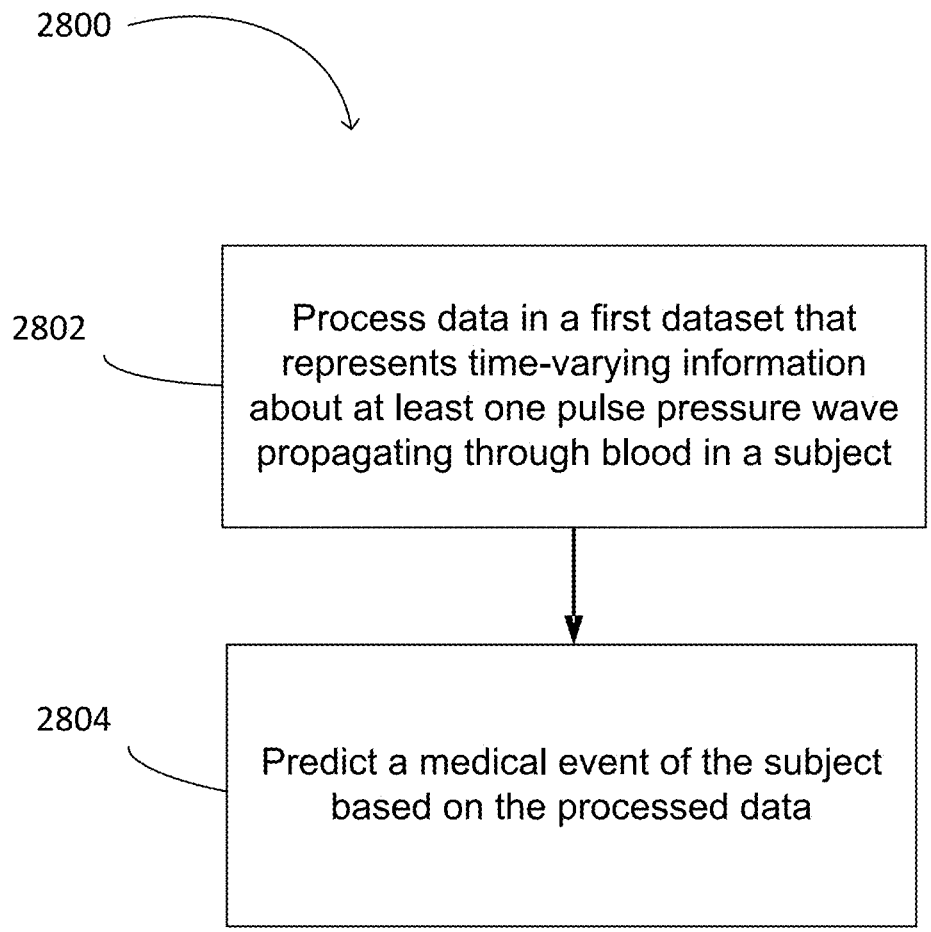
FIG. 28 is a flowchart depicting an example of a process for predicting a medical event.

An example process 2800 of predicting a medical event of a subject is shown in FIG. 28. A machine, such as a processor, that receives information from the optical sensors 110 of the device 100 can perform one or more steps of the process ##00. In some implementations, the machine can include the computing device 115 described above with reference to FIG. 1B. In the process 2800, initially, data in a first dataset that represents time-varying information about at least one pulse pressure wave propagating through blood in a subject can be processed (2802). Data in a second dataset that represents time-varying information about motion of the subject can also be processed. The data can be acquired at a location of the subject (e.g., the arm or the wrist of the subject). A medical event of the subject can then be predicted (2804). The medical event can be predicted based on the processed data. Medical events that can be predicted include tachycardia, hypertension, stroke, and heart condition.

Medication Compliance

The processor can also be programmed to ensure that the wearer of the device is adhering to a prescribed medication regimen. For example, for wearers who are prescribed blood pressure medication, the processor can be programmed to monitor the blood pressure of the wearer and to alert the wearer if, based on the blood pressure data, it appears that the wearer forgot to take his or her medication. The device can be used in this manner to monitor a wearer's adherence to a prescribed medication schedule for any of various other medications that impact the various different vital signs monitored by the device.

Medication Effectiveness

The processor can also be programmed to determine the effectiveness of a medication. For example, in the context of inhalation medications, it is unknown if generic inhalation medications have the same effectiveness as brand name inhalation medications. One reason for this is that environmental and genetic makeups are generally different between users. The processors can be programmed to monitor the heart rate and the blood oxygenation ($SpO_2$) of wearers of devices who are prescribed generic inhalation medication and wearers of devices who are prescribed name brand inhalation medication. The processors can also consider data related to environment and genetic makeups of the wearers. Data related to the effects of the inhalation medication on the wearers can be used to determine the effectiveness of the generic inhalation medication compared to the effectiveness of the name brand inhalation medication. The device can be used in this manner to monitor the effectiveness of any of various other medications that impact the various different vital signs monitored by the device.

In some implementations, the processor can determine a correlation between a particular medication's effectiveness and environmental factors. For example, two wearers of the device who reside in two different extreme environments (e.g., Alaska and Florida) may experience different effects from the particular medication. Differences in the medication's effectiveness may be attributed to the different extreme environments experienced by the wearers. For example, the processor can determine a correlation between the particular medication's effectiveness and the environmental temperature experienced the wearer.

In some implementations, the device may identify a correlation between a particular medication's effectiveness and other environmental factors. For example, differences in a medication's effectiveness between two users may be attributed to the food that people generally eat in a particular region, thereby allowing the device to identify food-drug interaction information related to the medication.

Because everyone has a different genetic makeup, different people may require different dosages and dosage timings of a particular medication. For example, a person with a relatively fast metabolism may be able to increase the effectiveness of a medication by taking multiple small doses of the medication over the course of the day. In contrast, a person with a relatively slow metabolism may benefit from taking fewer large doses. The device can be configured to determine an optimal timing and dosage regimen for a particular wearer by monitoring the wearer's vitals while the wearer is under the influence of the medication. For example, a wearer may take a medication to maintain his or her blood pressure below a particular level. After the wearer takes the general recommended dose of the medication, the device may determine that the wearer's blood pressure was reduced too much, and recommend that the wearer take a smaller dose the next day. The following day, the wearer may take the dosage amount recommended by the device. The device may determine that the wearer's blood pressure was reduced to the ideal level, but that the wearer may need to take a second small dose of the medication to maintain his or her blood pressure at the ideal level over the course of the day. In this way, the device can continuously refine the wearer's dosage regimen to be custom tailored to the wearer. The device can be used in this manner to determine an optimal dosage regimen for any of various other medications that impact the various different vital signs monitored by the device as described herein.

In some implementations, the processor can determine an optimal time for a wearer of the device to take a medication. For example, a doctor typically tell a patient to take particular medications at particular times of the day or under particular circumstances (e.g., in the morning, in the evening, with food, etc.). Such blanket directions do not typically apply to all patients under all circumstances. The processor can monitor the vital signs of the wearer of the device to determine the optimal time for the wearer to take the medication under the current circumstances. The processor can consider characteristics of the particular medication when making the determination.

For example, the wearer of the device may take a medication that has a tendency to cause the wearer to be energetic. A doctor may suggest that the medication be taken no later than 3:00 pm to prevent disruption of the wearer's sleep. By analyzing the wearer's vital signs, such as the wearer's heart rate and respiratory rate over the course of a particular day, the processor may determine that the wearer is more energized than usual. The processor may recommend that the wearer take the medication earlier than usual to prevent the wearer from becoming too energized and having his sleep disrupted later.

Figure 29:
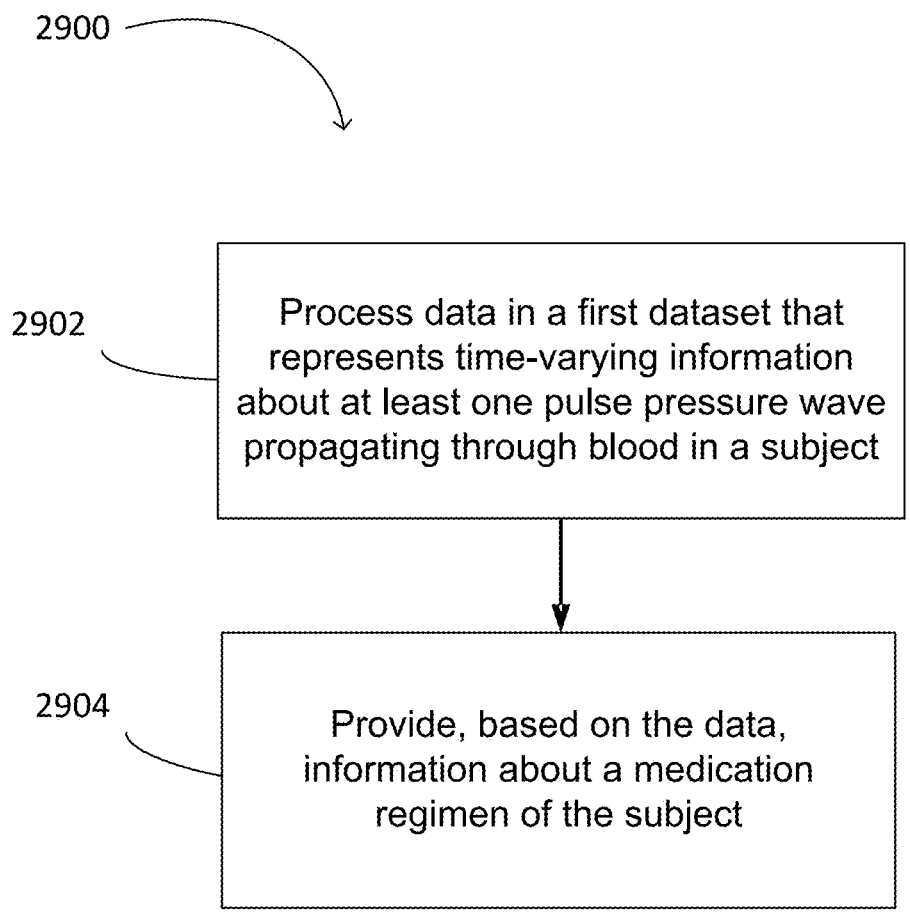
FIG. 29 is a flowchart depicting an example of a process for determining information about a medication regimen.

An example process 2900 of providing information about a medication regimen of a subject is shown in FIG. 29. A machine, such as a processor, that receives information from the optical sensors 110 of the device 100 can perform one or more steps of the process 2900. In some implementations, the machine can include the computing device 115 described above with reference to FIG. 1B. In the process 2900, initially, data in a first dataset that represents time-varying information about at least one pulse pressure wave propagating through blood in a subject can be processed (2902). Data in a second dataset that represents time-varying information about motion of the subject can also be processed. The data can be acquired at a location of the subject (e.g., the arm or the wrist of the subject). Information about a medication regimen of the subject can then be provided (2904). Based on the data, a determination can be made that the subject has potentially missed a dose of a medication, and a notification can be provided to the subject indicating such. Based on the data, a reaction of the subject to a medication can be determined, and a recommended medication regimen of the medication can be provided to the subject based on the reaction to the medication. The recommended medication regimen can include one or more recommended dosage timings and one or more recommended dosage amounts, each of which corresponds to one of the dosage timings.

Connectivity with Other Devices

Figure 30:
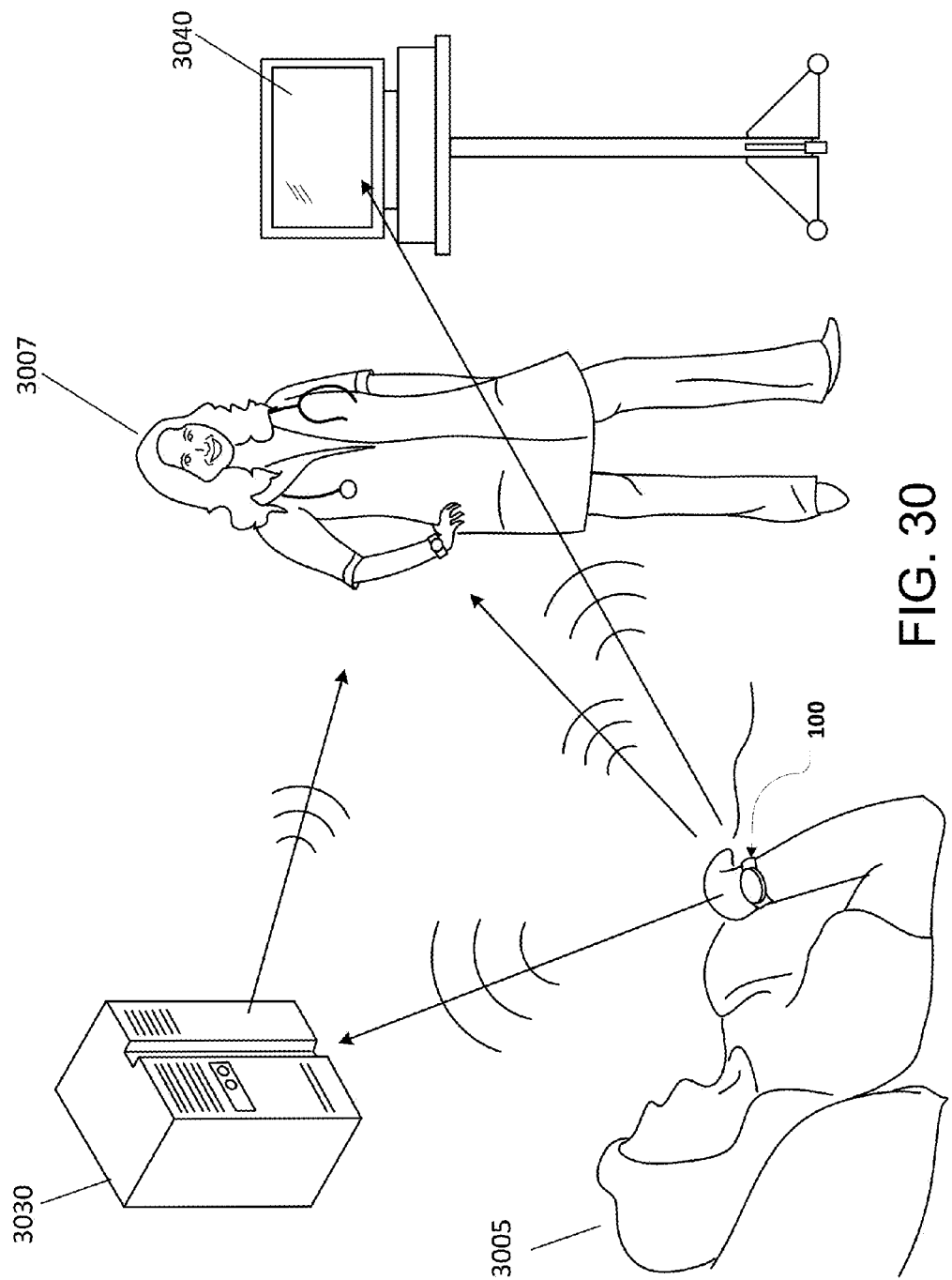
FIG. 30 shows an example where the technology is used at a medical or caregiving facility.

In some implementations, the device 100 can be configured to communicate with other computing devices. For example, the device 100 can include a transceiver module that can send data to, and receive data from, a server computer. In such cases, the device 100 can be configured to act as a client within a client-server architecture. The server computer can be configured to receive and store data provided by the device 100 and share the data with other computing devices. This is illustrated in FIG. 30, which shows an example where, a hospital, nursing home, or elder-care center uses a server computer (or another central computer acting as a hub) 3030 that is configured to receive communications from devices 100 worn by patients or residents 3005. In such cases, the server computer 3030 can be configured to determine, based on data received from a particular device 100, that the wearer of the device 100 is in need of assistance. The server computer can be configured to alert appropriate personnel (e.g., medical personnel 3007) accordingly. For example, based on data (e.g., heart rate or blood pressure) received from a particular device 100, the server computer 3030 may determine that the wearer of the particular device 100 is experiencing (or is likely to experience) a health-related emergency, and alert appropriate caregivers 3007 automatically (e.g., by sending a message to a computing device 3040 at a caregivers' station, sending a text message or paging message to the caregivers, triggering an alarm, or initiating an emergency call). In some implementations, in addition to health related information, the data received from the device 100 can include additional information (e.g. location data) that can be used in contextualizing the health information. For example, if the data received from the device 100 indicates that a patient is in a horizontal position at 2:00 AM, the situation may be determined as normal. However, if accompanying location data (provided, for example, by a GPS unit within the device 100) shows that the patient is in a corridor or bathroom, the server computer may determine that a potentially dangerous event (e.g., a fall or loss of consciousness) has occurred. In some implementations, the device 100 itself may make such a determination and forward the information to the server computer 3030 for taking an appropriate action.

In some implementations, the device 100 can be configured to communicate over a network (e.g., a Wi-Fi network) with other devices connected to the network. For example, the device 100 can be configured to communicate with a Wi-Fi enabled thermostat to facilitate control of ambient temperature based on vital signs data collected by the device 100. For example, temperature data collected using the device 100 can be used to determine that the wearer is cold, and the temperature can be increased accordingly. In another example, location data provided by the device 100 (possibly through a server computer) can be used to determine that the wearer is not at home, and the thermostat can be instructed to switch off the heating or cooling system accordingly. Location data can also be used, for example, to determine that the wearer is returning home, and the heating or cooling system can be switched on in advance.

Referring to FIG. 31, the device 100 (e.g., the wearable watch 3200 of FIGS. 32A and 32B) can be configured to wirelessly communicate (e.g., via a Bluetooth connection) with a proximity system 3100 that is configured to identify the location of the watch 3200. One or more proximity sensors 3102 positioned throughout a store can monitor the location of the watch 3200, thus determining the wearer's tendencies in the store. The location of the watch 3200 can be determined based on a strength of a wireless communication signal between the watch 3200 and one or more of the proximity sensors 3102. In some implementations, the proximity sensors 3102 are iBeacons™. The location information can be used to determine particular products and/or advertisements that the wearer expressed interest in. For example, the proximity system 3100 can determine that a wearer of the watch 3200 spent a particular amount of time at a location near a display for a newly-released smartphone 3104, thus making the inference that the wearer was examining and/or interacting with the display and the smartphone 3104. The information measured by the proximity system 3100 can be compared to vital information collected by the watch 32003 during the same time period to determine the wearer's reaction to the display and the smartphone 3104. For example, the wearer may have experienced an increase in heart rate, blood pressure, and respiratory rate while considering the display and the smartphone 3104, thereby indicating that the wearer is interested in and/or excited about the smartphone 3104. In some implementations, the wearer's vital signs may indicate that a particular display, product, and/or advertisement scares the wearer or causes the wearer to feel stress, as indicated by the measured vital signs.

In some implementations, the device can be configured to wirelessly communicate (e.g., via a Bluetooth connection) with other devices. Multiple devices can create a mesh network, with each device representing a node that relays data for the network. In this manner, a wearer who is in a location where other forms of communication are not available may still be able to communicate with the mesh network via the device. For example, a wearer who is in an underground tunnel may not have access to a cellular or Wi-Fi network, but may still be able to communicate with devices of other wearers. Such mesh network communication can be beneficial in certain emergency situations. For example, a wearer of the device who is performing an underground construction project may become lost and/or trapped, and the wearer may not have access to a cellular network to call for help. However, the wearer may be able to manually notify another wearer of the emergency condition via the mesh network of connected devices.

In some implementations, the device can detect and emergency condition based on the vitals of the wearer. For example, the device may detect a sudden increase in blood pressure, heart rate, and/or respiratory rate and infer that the wearer is under distress. Upon such a determination, the device can be configured to automatically establish a wireless Bluetooth connection with any other devices within range in order to notify wearers of the other devices of the emergency condition. The wireless Bluetooth connection may be capable of relaying information to other wearers that can be used to assist the other wearers in locating the distressed wearer. For example, the signal strength of the Bluetooth connection can be monitored to determine whether a potential rescuer is getting closer to the distressed wearer.

Multiple devices 100 can be used to measure environmental characteristics. In some implementations, multiple devices 100 can be configured to communicate with a Wi-Fi enabled thermostat to facilitate control of ambient temperature in public places based on users' vital signs data collected by the devices 100. Temperature data collected by the devices 100 can be used to determine that the wearers are cold, and the temperature in the public place can be increased accordingly. For example, temperature data collected by devices 100 worn by users who are together in a room can be used to determine that at least some of the wearers are cold, and the temperature of the room can be increased accordingly.

Further, location data provided by the GPS transponder of the devices 100 can be used to determine public places that are not occupied by users, and the thermostat can be instructed to switch off the heating or cooling system accordingly. Similarly, location data can also be used, for example, to determine that users are about to be at a particular public place, and the heating or cooling system can be switched on in advance.

In some implementations, location data and temperature data provided by the devices 100 can be used to determine that nobody is in a particular subway car, and the heating or cooling system in the particular subway car can be switched off accordingly. Similarly, location and temperature data provided by the devices 100 can be used to determine that one or more users of the devices 100 are about to occupy a particular subway car, and the heating or cooling system of the particular subway car can be switched on in advance (e.g., to allow the subway car to assume an appropriate temperature in advance of being occupied).

Because the data from the device 100 can be used to identify a wearer, as well as make various inferences about the state of the body (activity, tiredness, stress level, sleep pattern, etc.) and/or mind (mood, alertness, etc.) of the wearer, different types of personalization can be facilitated accordingly, via communications with appropriate devices and systems. Examples of such personalization can include providing mood-based lighting or music and activity-based temperature control. In some implementations, an entertainment device such as a smart TV can be configured to provide personalized suggestions for TV shows, movies, or games based on a state of a user's body and/or mind as determined from data received from the device 100.

In some implementations, data from the device 100 can be used to cause a particular TV show or movie to be dynamically changed. For example, a TV show or a movie can have multiple pre-made endings. The device 100 can consider the wearer's vitals, such as blood pressure, heart rate, and respiratory rate, to make inferences about the physical and/or mental state of the wearer. The device 100 can then cause the particular TV show or movie to be dynamically altered based on the state of the wearer. For example, if the wearer's vitals indicate that the wearer is bored (e.g., as indicated by a reduced heart rate and/or respiratory rate), the device 100 may cause the TV show or movie to dynamically adapt and play a more exciting alternate ending. On the other hand, if the wearer's vitals indicate that the wearer is scared or upset by the content of the TV show or movie (e.g., as indicated by an increase in blood pressure, heart rate, and/or respiratory rate), the device 100 may cause the TV show or movie to dynamically adapt and play a toned-down alternate ending. The device 100 can be used in a similar manner to dynamically alter audio output devices (e.g., stereos or entertainment systems), video games, and other entertainment mediums, as described in more detail below.

Figure 33:
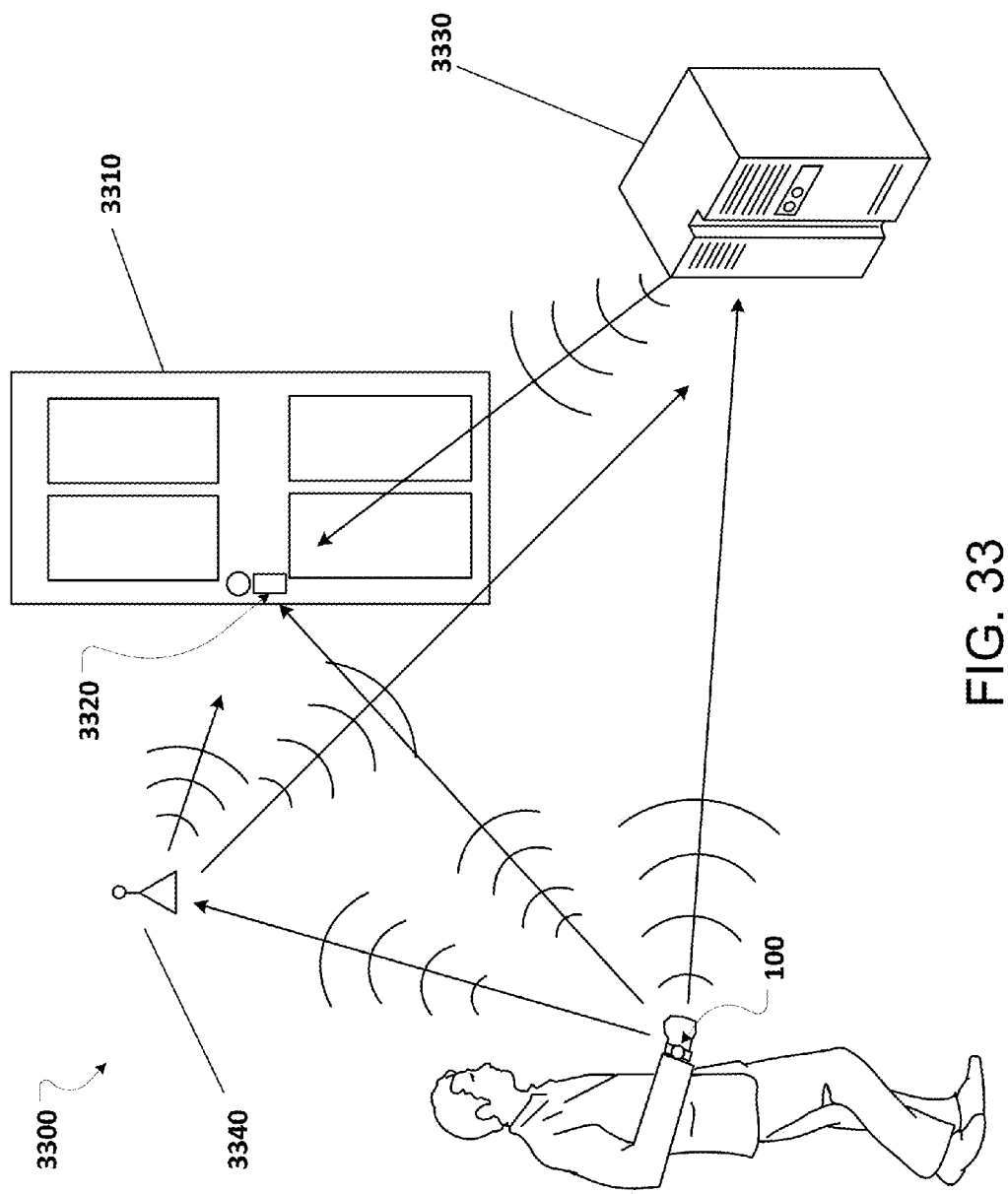
FIG. 33 shows an example of an environment where the technology is used for access control.

In some implementations, the device 100 can be used to facilitate access control. An example of such an environment 3300 is shown in FIG. 33. In the example of FIG. 33, a biometric signature (e.g., one based on cardiac morphology, or a combination of one or more parameters detected, derived using the device 100) of a wearer of the device 100 can be used in conjunction with location data to determine that a wearer is proximate to an access point 3310 such as a door or turnstile. A network-connected lock or another access control mechanism 3320 associated with the access point 3310 can be activated based on determining that the biometric signature corresponds to a wearer authorized to access the corresponding access-controlled premises.

In some implementations, information related to the biometric signature of the user can be provided to the access control mechanism 3320 via a remote server 3330 that communicates with the device 100. For example, the remote server 3330 can determine, based on data received from the device 100, whether a biometric signature of the user corresponds to a user authorized to access the controlled premises. If the server 3330 determines that the user is authorized to access the premises, the server 3330 can then send a signal to the access control mechanism 3320 to unlock the access point 3310. In some implementations, the communications between the server 3330 and the device 100 can be via a local hub 3340 (e.g., a proximity sensor) that communicates with the server 3330 to forward information received from the device 100. In some implementations, the local hub 3340 can be configured to process the information received from the device 100 and directly transmit a signal to the access control mechanism 3320 accordingly. The access control mechanism can also be configured to communicate directly with the device 100. In such cases, information from the device 100 is transmitted to the access control mechanism 3320, which unlocks itself upon determining, based on the received information, that the corresponding user is authorized to access the controlled premises.

Figure 34:
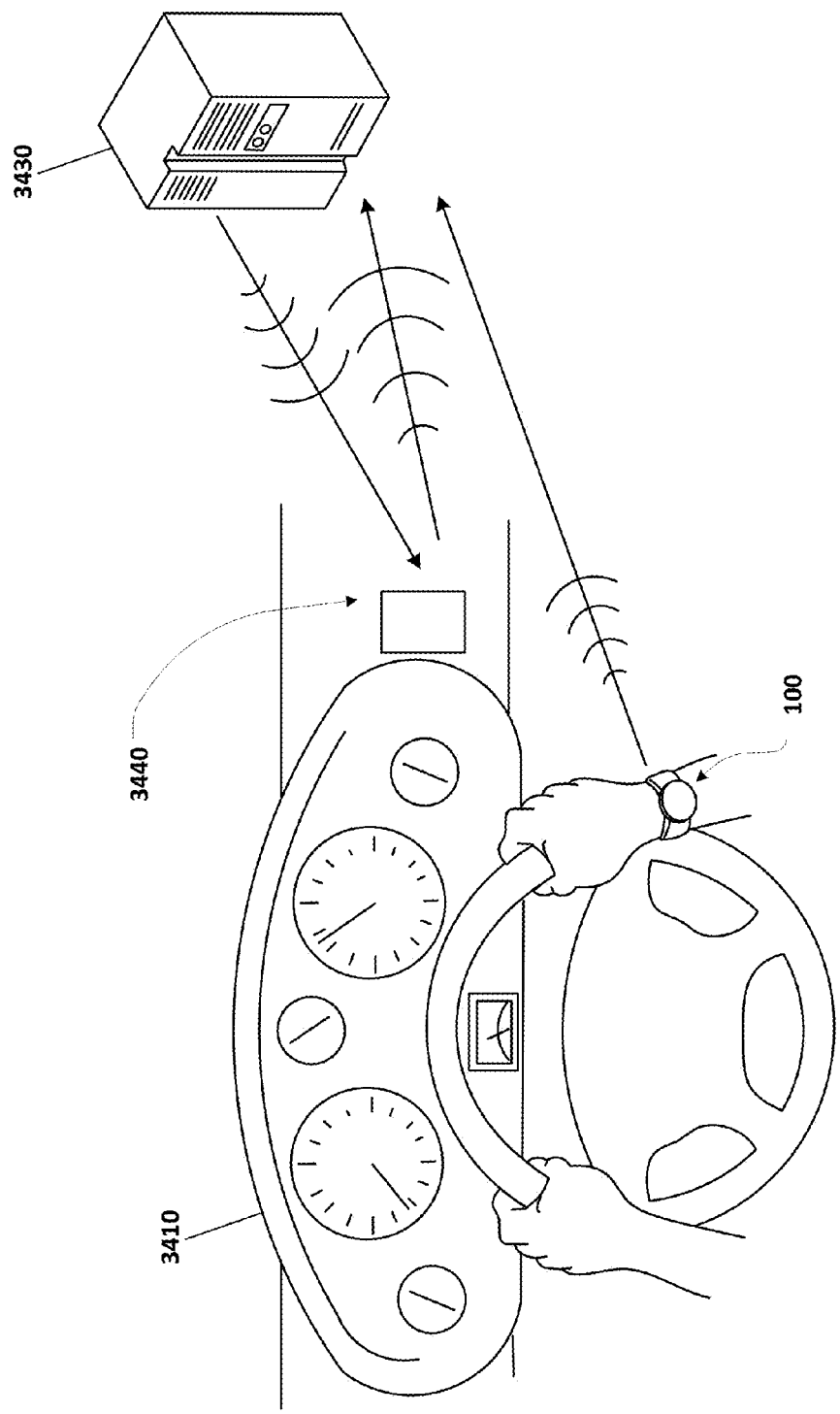
FIG. 34 shows an example where the technology is used for allowing a user to access/operate a vehicle of other machinery.

In some implementations, the biometric signature can be used to allow the wearer to access/operate a vehicle or another access-controlled machine. This is illustrated in the example depicted in FIG. 34. In the example of FIG. 34, data from the device 100 can be used to identify whether an individual is authorized to operate a vehicle or machine 3410, and/or determine whether the physical and/or mental state of the individual is appropriate for handling or operating the vehicle or machine. In some implementations, information about the user can be provided from the device 100 to a remote server 3430 either directly or via a transceiver module 3440 deployed on the vehicle or machine. The remote server 3430 (or the transceiver module 3440) can determine, based on data received from the device 100, whether a biometric signature of the user corresponds to a user authorized to access the controlled premises. The server 3430 (or the transceiver module 3440) can also determine, for example, whether the user possesses sufficient mental/physical capability for operating the vehicle or machine. In one example, data from the device 100 can be used to prevent a pilot from operating an airplane if his/her vital signs indicate an alertness level less than a threshold. In another example, data from the device 100 can be used to prevent a driver from operating a vehicle if his/her stress level is determined to be higher than a threshold level. This can help, for example, reduce occurrences of stress-related traffic issues (e.g., road rage) and accidents. In some implementations, if the server 3430 determines that a user's mental/physical state is not suitable for operating the vehicle or machine, the server 3430 can then send a signal to the transceiver module 3440 to shut down the vehicle or machine, or otherwise alert the user about the situation. In some implementations, the server 3430 (or the transceiver module 3440) can send a signal to the device 100 to alert the user. For example, if the alertness of the user is waning during the operation of the vehicle (e.g., because of the user dozing off on the wheel), a signal can be sent to the device 100 to alert the user to take corrective measures.

In some implementations, the device 100 can be configured to communicate with the transceiver module 3440 of the vehicle. In such cases, the transceiver module 3440 can be configured to provide feedback to other modules in the vehicle based on data received from the device 100 (either directly, or via the server 3430). For example, the transceiver module 3440 of the car can be configured to provide feedback signals to a temperature control system of the vehicle to adjust the temperature based on vital signs data collected by the device 100. In another example, the transceiver module 3440 may use data from the device 100 to provide feedback to a collision avoidance system that, for example, triggers an alarm (and/or slows the vehicle down) upon determining that a driver wearing the device 100 is not adequately alert. In another example, the transceiver module 3440 may use data from the device 100 to turn off an operation switch (e.g., an ignition) of the vehicle. In some implementations, in case of accidents, the data from the device 100 can be transmitted (possibly via the transceiver module 3440) to appropriate authorities for determining a nature of resources to be sent to the accident scene. For example, the data from the device 100 may indicate that a driver wearing the device 100 requires the assistance of a standard paramedic, or the data from the device 100 may indicate that the driver requires the assistance of a trauma unit. The data from the device 100 may also indicate whether the wearer of the device 100 requires immediate attention from rescue workers, or alternatively whether the wearer of the device 100 can be treated at a later time (e.g., in order to first treat others involved in the accident).

Figure 35:
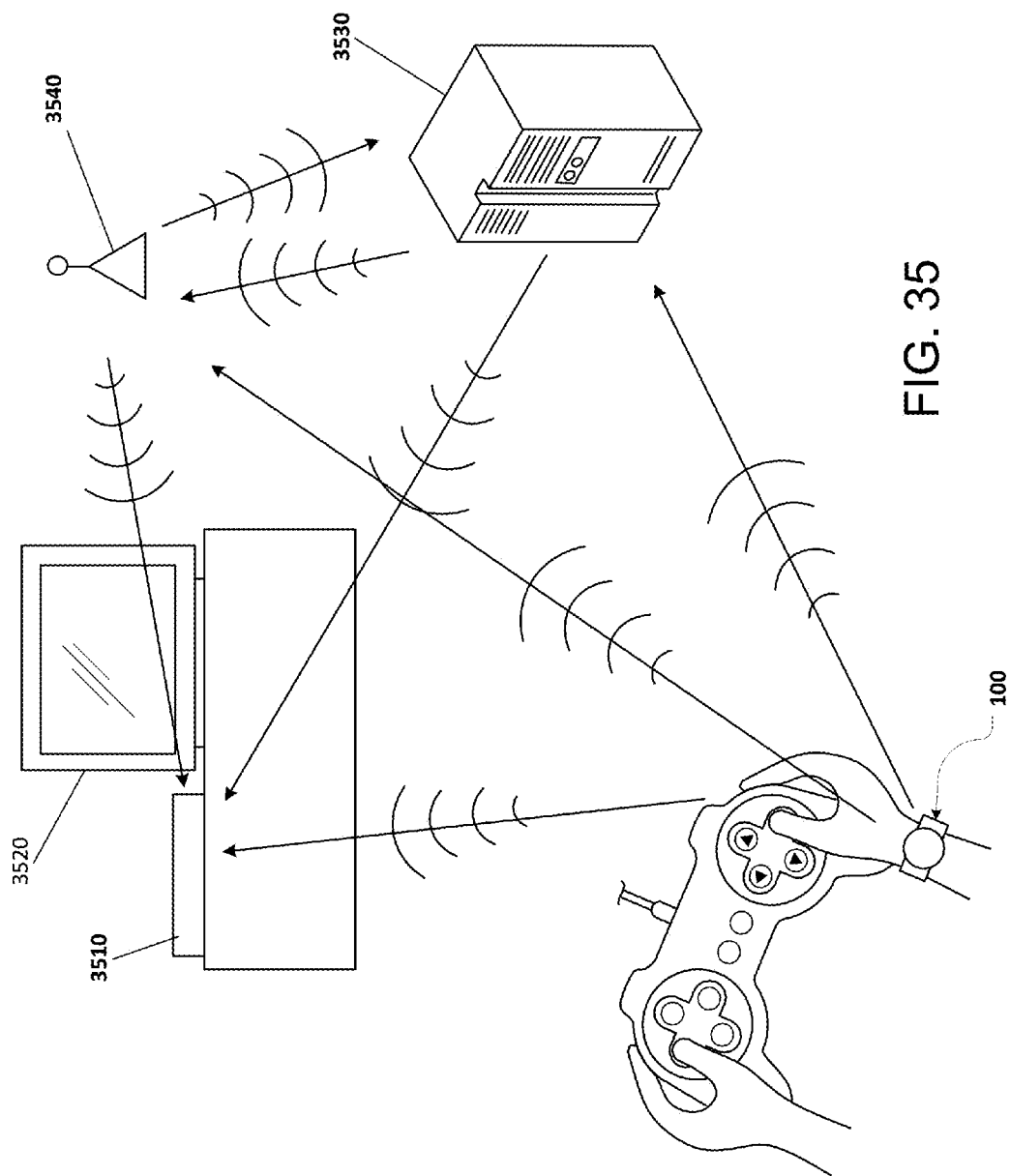
FIG. 35 shows an example where the technology is used for controlling gaming and/or entertainment systems.

In some implementations, the device 100 can be configured to communicate with a gaming device such as a video game console. This is illustrated in the example depicted in FIG. 35. In the example of FIG. 35, data from the device 100 can be used to control a gaming device 3510 based on an identity and/or state of the body of the user. For example, one or more of blood pressure data, respiratory rate, and heart rate obtained using the device 100 can be used to determine an interest level or engagement level of the user. If the user is determined to show more interest in certain game situations as opposed to others, the gaming device can be configured to adaptively provide game situations that the user is interested in. If the data from the device 100 indicates a low level of interest, steps can be taken (e.g. increasing the background sound level, playing a stimulating track, or introducing additional challenges) to increase the interest level of the user. This way, games being played on the gaming device 3510 can be made more appealing to the user. In some implementations, the gaming device 3510 can be configured to be turned off if the user's body state is determined to be in a potentially harmful condition. For example, if the blood pressure or heart rate data from the device 100 indicates that the stress level of the user is above a threshold, the gaming device can be instructed to shut down to prevent the user from continuing to play.

In some implementations, information from the device 100 can be provided to a remote server 3530 either directly, or via a local hub 3540 that communicates with the server 3530. The information from the server 3530 can also be transmitted, for example, either directly or via the local hub 3540 to the gaming device 3510. In some implementations, the gaming device 3510 can be configured to receive data directly from the device 100 (or via the local hub 3540) and change the game situations accordingly.

In some implementations, operations of the entertainment or gaming devices can be linked to data obtained from the device 100. For example, if a user opts to force himself to exercise, he can choose a configuration in which a gaming device 3510 or TV 3520 will be switched on only if he has exercised for a predetermined length of time during a given time period. In some implementations, if data from the device 100 indicates that the user has fallen asleep, the entertainment device (e.g., the TV 3520) may also be switched off based on such data.

Figure 36:
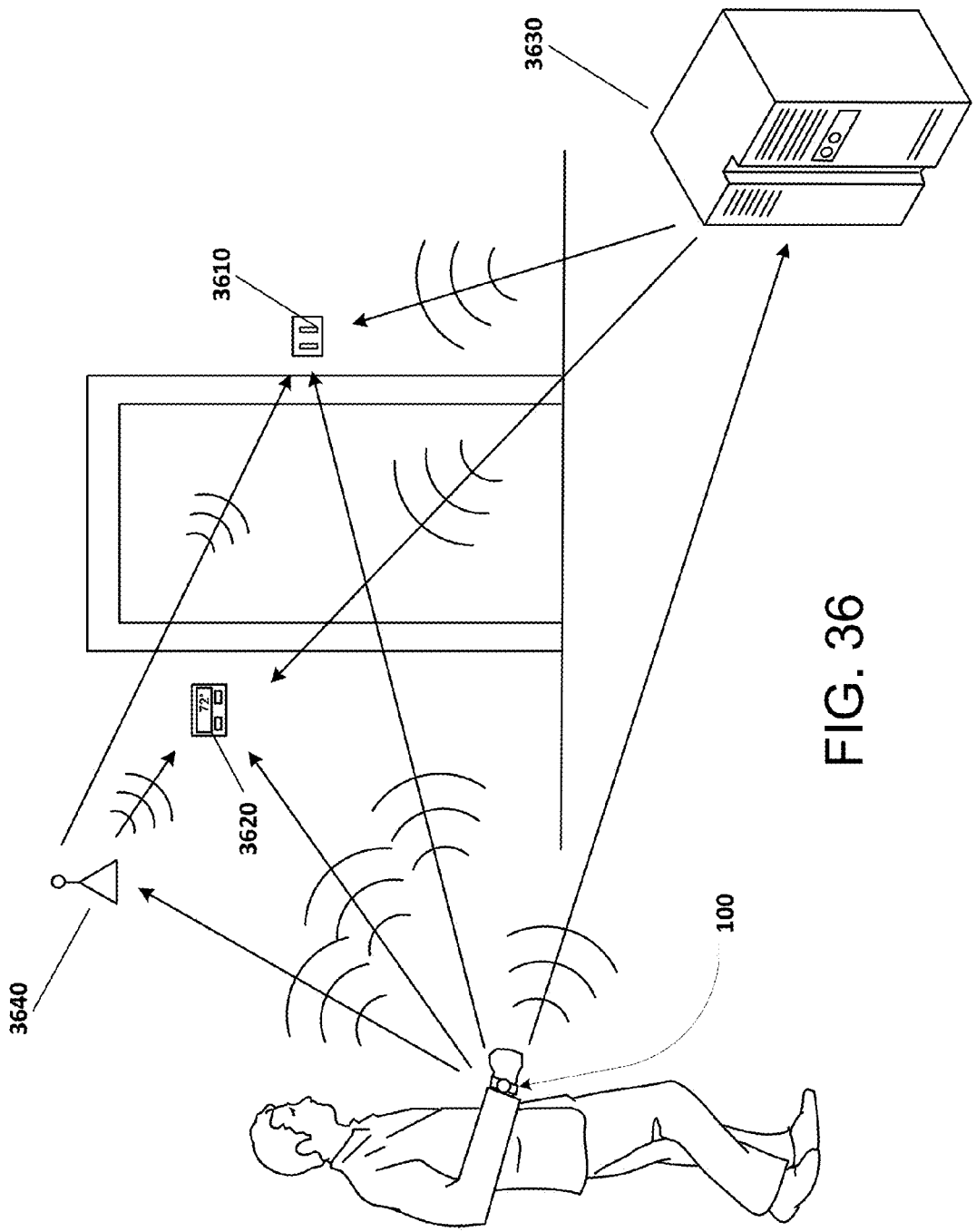
FIG. 36 shows an example where the technology is used for controlling various devices connected to a network.

Further, as shown in the example depicted in FIG. 36, the device 100 can alternatively or additionally be linked to other types of devices, such as lighting units 3610, thermostats 3620, etc., that can be adjusted based on data from the device 100. For example, biometric signature or health data obtained using the device 100 can be used in determining if a user is hot or cold, and the thermostat 3620 can be adjusted accordingly. In another example, data from the device 100 can be used in determining that a user is approaching a room, and the lights in the room can be turned on via communications with the lighting unit 3610. The data about the user can be provided to the lighting unit 3610 or thermostat 3620 via a remote server 3630 that communicates with the device 100. In one example, if the server 3630 determines, based on data received from the device 100, that the user is feeling too cold, the server 3630 can then send a signal to the thermostat 3620 to increase the temperature of the room. In some implementations, the communications between the server 3630 and the device 100 can be via a local hub 3640 (e.g., a proximity sensor) that communicates with the server 3630 to forward information received from the device 100. In some implementations, the local hub 3640 can be configured to process the information received from the device 100 and directly transmit a signal to, for example, the lighting unit 3610 or the thermostat 3620, accordingly. In some implementations, the network connected lighting unit 3610 or thermostat 3620 can be configured to communicate directly with the device 100. In such cases, information from the device 100 can be transmitted to the thermostat 3620, which adjusts the temperature upon determining, based on the received information, that the corresponding user uncomfortable at a current temperature setting. In some implementations, network connected devices such as the lighting unit 3610, thermostat 3620, gaming device 3510, or TV 3520, can be turned off or adjusted upon receiving data indicating that the user has fallen asleep.

The interest level or engagement level determination, as described above with respect to a gaming device, can also be used for other applications. For example, upon authorization from a user, such information may be used by a dating or matchmaking service. For example, by reviewing a user's vital signs while the user is on a date, a determination can be made whether the user is interested in the other person or not. If the interest level is not determined to satisfy a threshold level, the dating or match-making service may refrain from suggesting persons with similar profiles. On the other hand, if the interest level is determined to be high (i.e., the interest level satisfies a threshold condition), the dating or matchmaking service may suggest to the user other persons with similar profiles. The interest level based suggestions can be provided, for example, by a processing device that receives the user's data and retrieves potential matches from a database. In some implementations, the process can be made completely automated to avoid the user's personal data being exposed to human personnel. In some implementations, the user's data can be anonymized such that a particular user cannot be identified by human personnel. In some implementations, some of the data or feedback received from the device 100 can be stored within a profile of the user (based on authorization and permissions from the user) to suggest future matches that the user is more likely to be interested in.

In some implementations, information based on the data collected by the device 100 can be made available to the user, for example, via an application executing on a smartphone device. The application can include one or more user interfaces that allow the user to review the variations over the course of a particular time period (e.g., a day, overnight, a week, or a month) or during a particular event (e.g., a meeting, an exercise session, or a date). Examples of such user interfaces 3900, 3925, and 3950 are shown in FIGS. 39A-39C. A user interface such as the example user-interface 3900 can enable a user to see how various events in his/her life affect stress levels, and possibly take action accordingly. For example, the user interface 3900 can indicate that the user tends to become stressed when attending to work-related e-mails late at night. The user may then make a conscious effort to avoid looking at work-related emails late at night to alleviate stress. If a particular activity is determined to have a beneficial effect on the user, the user can make an effort to increase such activities in his/her daily life. The user interface 3900 can include suggestions for improving stress levels, and show a graphical representation of the stress level variations over a period of time (e.g., a week).

In some implementations, a user interface 3925 can show variations of the vital signs during a certain activity (e.g., listening to music or running) For example, the user interface 3925 can show variation in heart rate for a running session and graphically compare the variation with other baselines such as the user's own variation from a previous time, or a professional athlete's variations for a similar activity. The user can then determine if his/her fitness level is improving or deteriorating. In some implementations, a user interface such as the example user interface 3950 can be configured to display various vital signals (e.g., heart rate, cardiac power, heart rate volume, recovery rate, etc.) related to the cardiac health of the user.

Figure 37:
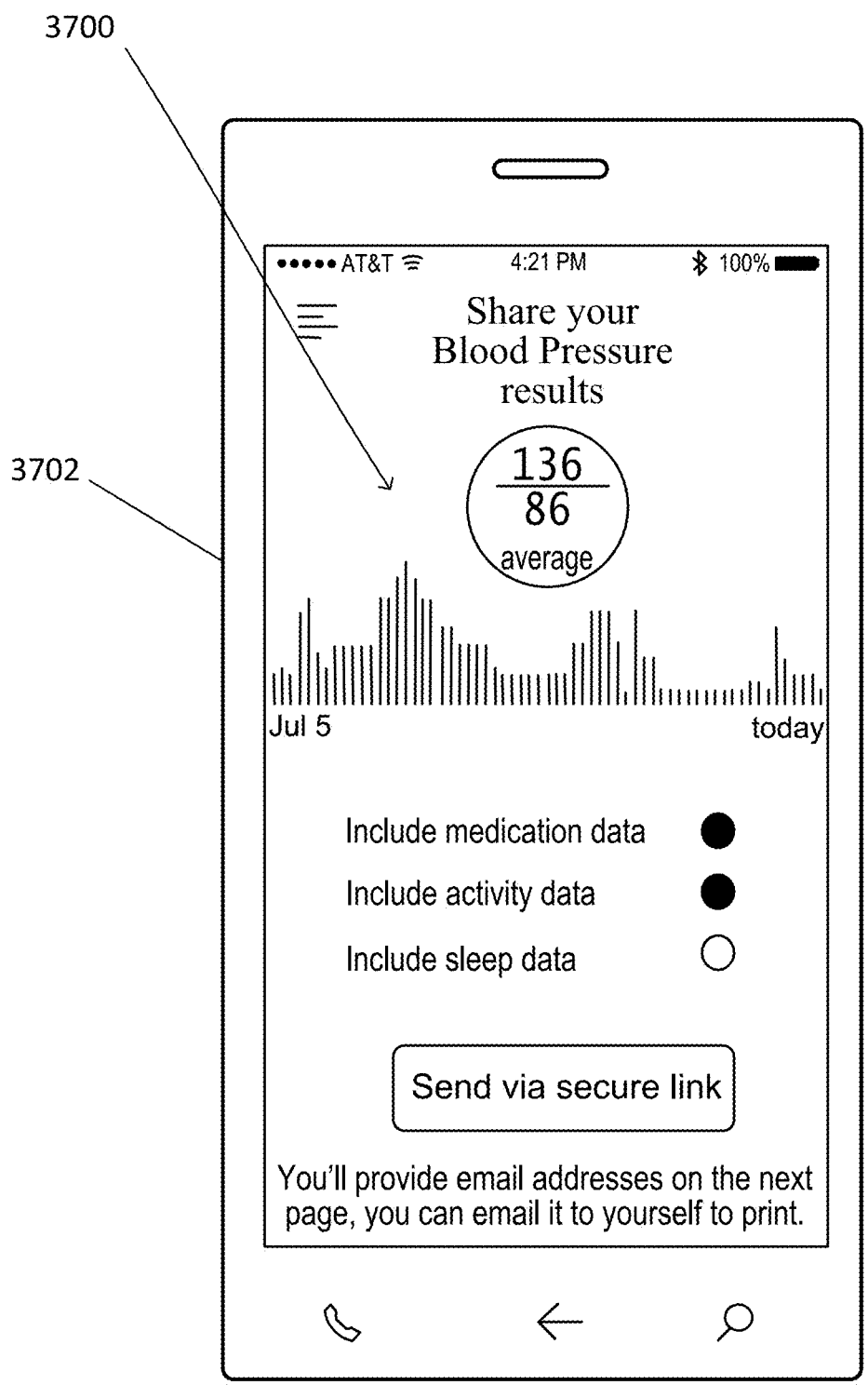
FIG. 37 is an example of a screenshot that displays and allows sharing of blood pressure results.

FIG. 37 shows an example screenshot 3700 on a mobile phone 3702 of a wearer for the wearer to view and share his or her blood pressure results. In this example, the wearer's average blood pressure is 136/86 mmHg. A graph displays the wearer's blood pressure over a number of days. The wearer has the option to share the blood pressure data with other people via a secure link. The wearer can also choose to share other information with other people, such as the wearer's medication data, activity data, and sleep data.

Figure 38:
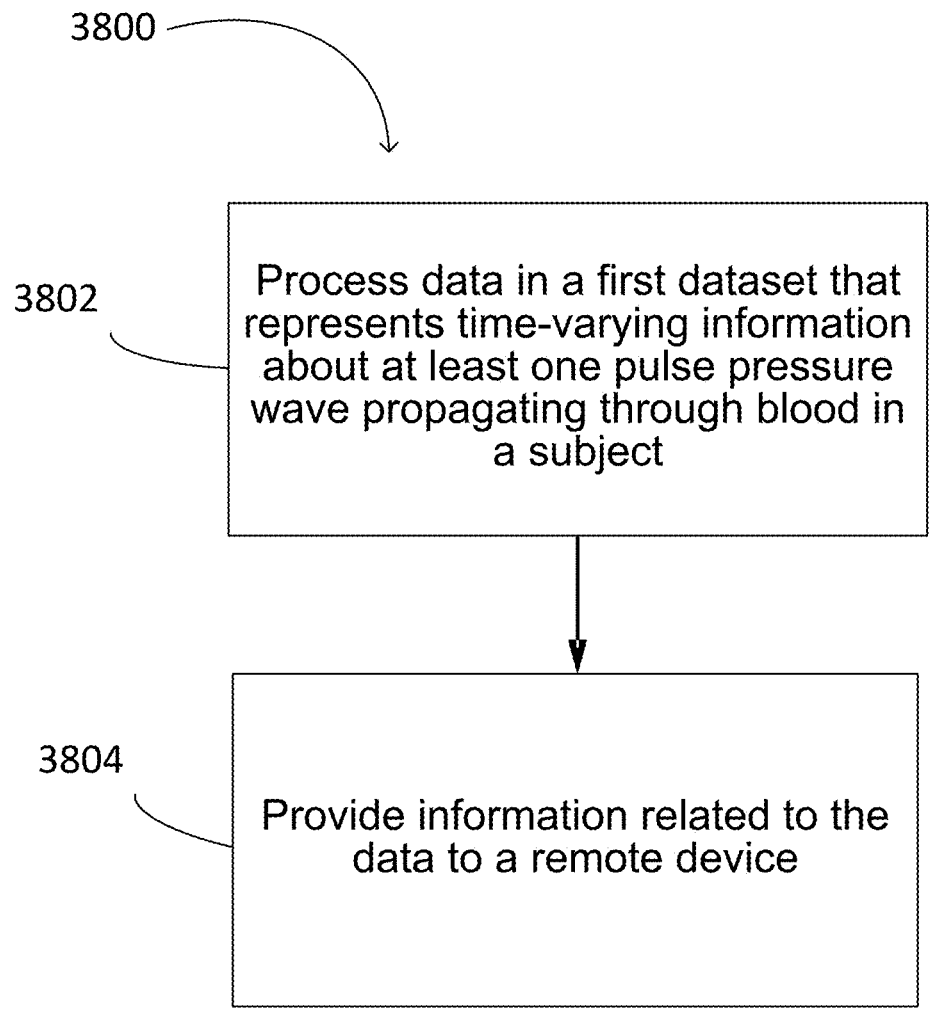
FIG. 38 is a flowchart depicting an example of a process for controlling remote devices using the technology described in this document.

An example process 3800 of providing information related to the processed data to a remote device is shown in FIG. 38. A machine, such as a processor, that receives information from the optical sensors 110 of the device 100 can perform one or more steps of the process 3800. In some implementations, the machine can include the computing device 115 described above with reference to FIG. 1B. In the process 3800, initially, data in a first dataset that represents time-varying information about at least one pulse pressure wave propagating through blood in a subject can be processed (3802). Data in a second dataset that represents time-varying information about motion of the subject can also be processed. The data can be acquired at a location of the subject (e.g., the arm or the wrist of the subject). Information related to the processed data can then be provided to a remote device (3804). The remote device can be a server, a thermostat, a light, an entertainment device, a television, an audio output device, or a gaming device. The remote device can operate based on the processed data.

Computing Device

Figure 40:
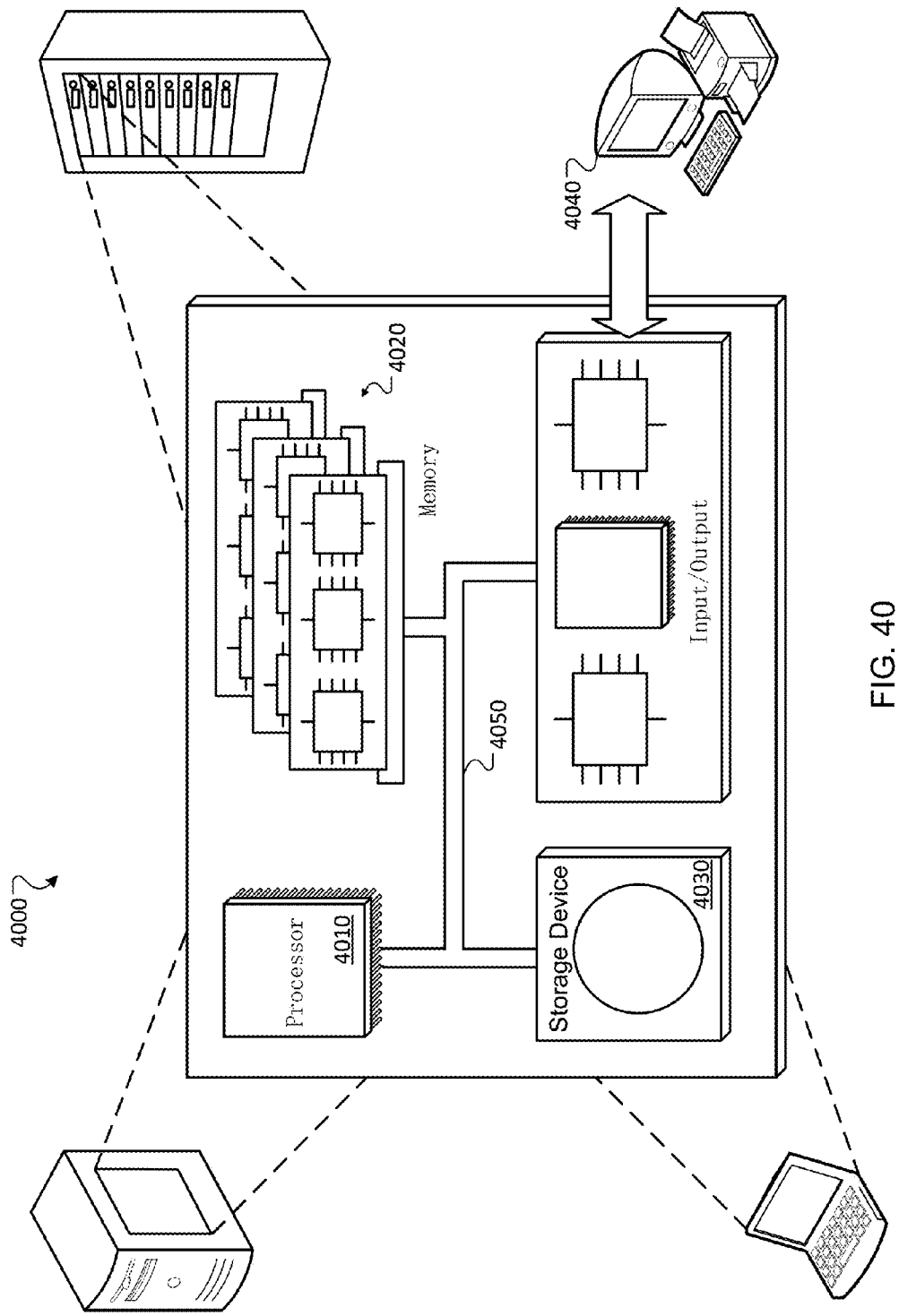
FIG. 40 is an example of a block diagram of a computer system.

FIG. 40 is block diagram of an example computer system 4000 that can be used for performing one or more operations related to the technology described above. In some implementations, the computer system 4000 can be used to implement any portion, module, unit or subunit of the device 100, or computing devices and processors referenced above. The system 4000 includes a processor 4010, a memory 4020, a storage device 4030, and an input/output device 4040. Each of the components 4010, 4020, 4030, and 4040 can be interconnected, for example, using a system bus 4050. The processor 4010 is capable of processing instructions for execution within the system 4000. In one implementation, the processor 4010 is a single-threaded processor. In another implementation, the processor 4010 is a multi-threaded processor. The processor 4010 is capable of processing instructions stored in the memory 4020 or on the storage device 4030.

The memory 4020 stores information within the system 4000. In one implementation, the memory 4020 is a computer-readable storage device that includes a non-transitory computer readable medium. In general, non-transitory computer readable medium is a tangible storage medium for storing computer readable instructions and/or data. In some cases, the storage medium can be configured such that stored instructions or data are erased or replaced by new instructions and/or data. Examples of such non-transitory computer readable medium include a hard disk, solid-state storage device, magnetic memory or an optical disk. In one implementation, the memory 4020 is a volatile memory unit. In another implementation, the memory 4020 is a non-volatile memory unit.

The storage device 4030 is capable of providing mass storage for the system 4000. In one implementation, the storage device 4030 is a computer-readable medium. In various different implementations, the storage device 4030 can include, for example, a hard disk device, an optical disk device, or some other large capacity storage device.

The input/output device 4040 provides input/output operations for the system 4000. In one implementation, the input/output device 4040 can include one or more of a network interface devices, e.g., an Ethernet card, a serial communication device, e.g., an RS-232 port, and/or a wireless interface device, e.g., and 802.11 card. In another implementation, the input/output device can include driver devices configured to receive input data and send output data to other input/output devices, e.g., keyboard, printer and display devices.

Although an example processing system has been described in FIG. 40, implementations of the subject matter and the functional operations described in this specification can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, or a combination of one or more of them.

The term "processing system" encompasses all apparatus, devices, and machines for processing data, including by way of example a programmable processor, a computer, or multiple processors or computers. The processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand-alone program, a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile memory, media and memory devices, including by way of example, semiconductor memory devices, e.g., EPROM, EEPROM, and flash memory devices; magnetic disks, e.g., internal hard disks or removable disks; magneto optical disks;

and CD ROM and DVD ROM disks. The processor and the memory can be supplemented by, or incorporated in, special purpose logic circuitry.

Implementations of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client server relationship to each other.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations of the invention have been described. Nevertheless, it will be understood that various modifications may be made without departing from the spirit and scope of the technology described in this document. Accordingly, other implementations are within the scope of the following claims.

The invention claimed is:

1. A method comprising:
obtaining, using a first sensor, a first dataset that represents time-varying information about at least one pulse wave propagating through blood in a subject, wherein the first dataset is obtained from a particular portion of the body of the subject;
determining, based at least in part on the data in the first dataset, two or more of a blood pressure, a heart rate, and a respiratory rate of the subject;
processing the first dataset to determine a condition of the subject, the condition comprising one or both of a stress level and an interest level; and
transmitting, using a wireless transmission module, a control signal related to the condition of the subject, the control signal configured to cause a parameter of a remote device to be changed based on one or both of the stress level and the interest level of the subject, wherein one or both of the stress level and the interest level is determined based on comparing two or more of the blood pressure, the heart rate, and the respiratory rate of the subject to corresponding baseline values associated with the subject.

2. The method of claim 1, further comprising obtaining, using a second sensor, a second dataset that represents time-varying information about motion of the subject, wherein the second dataset is obtained from the particular portion of the body of the subject.

3. The method of claim 2, wherein the information about at least one pulse wave propagating through blood in the subject comprises photoplethysmographic (PPG) data and the information about motion of the subject comprises one or both of motioncardiogram (MoCG) data and gross motion data.

4. The method of claim 1, further comprising determining, based on the data in the first dataset, a heart rate variability of the subject, wherein the condition of the subject is based on one or more of the blood pressure, the heart rate, the heart rate variability, and the respiratory rate of the subject.

5. The method of claim 1, wherein the condition of the subject is related to whether the subject is experiencing or has experienced one or more of hypertension, a stroke, abnormal heart function, tachycardia, arrhythmia, and a concussion.

6. The method of claim 1, wherein the control signal is transmitted to an intermediate device, and the intermediate device transmits a second signal to the remote device.

7. The method of claim 1, wherein the control signal is transmitted directly to the remote device.

8. The method of claim 1, wherein the first dataset is acquired continuously.

9. The method of claim 1, wherein the first dataset is acquired by a device worn by the subject, and the device does not reduce a mobility of the subject.

10. The method of claim 1, wherein the particular portion of the body of the subject is a wrist of the subject.

11. The method of claim 1, wherein the control signal is configured to generate an alert on the remote device that indicates that the subject is experiencing or has experienced a health-related problem.

12. The method of claim 11, wherein the remote device is a mobile phone.

13. The method of claim 1, further comprising:
identifying a first point in the first dataset, the first point representing an arrival time of the pulse wave at a first body part of the subject;
identifying a second point in a second dataset that represents time-varying information about motion of the subject, the second point representing an earlier time at which the pulse wave traverses a second body part of the subject; and
computing a pulse transit time (PTT) as a difference between the first and second points, the PTT representing a time taken by the pulse wave to travel from the second body part to the first body part of the subject.

14. The method of claim 13, wherein the blood pressure of the subject is determined based on the PTT.

15. The method of claim 13, wherein the first and second datasets are obtained from the first body part, and the second body part is an artery extending from the heart of the subject.

16. The method of claim 1, wherein the control signal is further related to a location of the subject.

17. The method of claim 16, wherein information related to the location of the subject is obtained using a third sensor.

18. The method of claim 16, wherein
the remote device is a light,
the control signal causes the light to adjust a lighting setting at a time that is based on the location of subject, and
the lighting setting is adjusted when the subject is within a predefined distance from a location that is illuminated by the light.

19. The method of claim 1, wherein the control signal is further related to a temperature of the subject.

20. The method of claim 19, wherein information related to the temperature of the subject is obtained using a fourth sensor.

21. The method of claim 19, wherein
the remote device is a thermostat,
the control signal causes the thermostat to adjust a temperature setting in accordance with a location and temperature of the subject,
the time when the thermostat adjusts the temperature setting is based on the location of the subject, and
the temperature setting of the thermostat is adjusted when the subject is within a predefined distance from a location that is temperature-controlled by the thermostat.

22. The method of claim 1, wherein the remote device is an entertainment device.

23. The method of claim 22, wherein the condition of the subject indicates whether the subject has exercised for a predetermined length of time, and the control signal prohibits the entertainment device from being turned on unless the subject has exercised for the predetermined length of time.

24. The method of claim 22, wherein the control signal causes the entertainment device to provide content personalized for the subject based on the condition of the subject.

25. The method of claim 24, wherein the condition of the subject comprises one or both of an interest level in the content and a stress level of the subject while the subject is experiencing the content.

26. The method of claim 25, wherein the stress level of the subject is based on the first dataset and information that is obtained using an impedance sensor.

27. The method of claim 25, wherein the control signal causes the entertainment device to provide content designed to excite the subject if the interest level in the content is below a threshold, or provide content designed to calm the subject if the stress level of the subject while the subject is experiencing the content is above a threshold.

28. A method comprising:
receiving, from a wireless device, a first dataset that represents time-varying information about at least one pulse wave propagating through blood in a subject, wherein the first dataset is obtained from a particular portion of the body of the subject;
determining, based at least in part on the data in the first dataset, two or more of a blood pressure, a heart rate, and a respiratory rate of the subject
processing the first dataset to determine a condition of the subject, the condition comprising one or both of a stress level and an interest level; and
transmitting, to a remote device, a control signal related to the condition of the subject, the control signal configured to cause a parameter of the remote device to be changed based on one or both of the stress level and the interest level of the subject, wherein one or both of the stress level and the interest level is determined based on comparing two or more of the blood pressure, the heart rate, and the respiratory rate of the subject to corresponding baseline values associated with the subject.

29. A system comprising:
a wireless device comprising:
a first sensor configured to obtain a first dataset that represents time-varying information about at least one pulse wave propagating through blood in a subject, wherein the first sensor is configured to obtain the first dataset from a particular portion of the body of the subject;
one or more processing devices configured to
determine, based at least in part on the data in the first dataset, two or more of a blood pressure, a heart rate, and a respiratory rate of the subject, and
process the first dataset to determine a condition of the subject, the condition comprising one or both of a stress level and an interest level; and
a transmission module configured to transmit a control signal related to the condition of the subject, the control signal configured to cause a parameter of a remote device to be changed based on one or both of the stress level and the interest level of the subject, wherein one or both of the stress level and the interest level is determined based on comparing two or more of the blood pressure, the heart rate, and the respiratory rate of the subject to corresponding baseline values associated with the subject.

30. A system comprising:
memory; and
one or more processors configured to:
receive a first dataset that represents time-varying information about at least one pulse wave propagating through blood in a subject, wherein the first dataset is obtained from a particular portion of the body of the subject;
determine, based at least in part on the data in the first dataset, two or more of a blood pressure, a heart rate, and a respiratory rate of the subject
process the first dataset to determine a condition of the subject, the condition comprising one or both of a stress level and an interest level; and
transmit, to a remote device, a control signal related to the condition of the subject, the control signal configured to cause a parameter of the remote device to be changed based on one or both of the stress level and the interest level of the subject, wherein one or both of the stress level and the interest level is determined based on comparing two or more of the blood pressure, the heart rate, and the respiratory rate of the subject to corresponding baseline values associated with the subject.

* * * * *